US009182395B2

(12) United States Patent
Tajima

(10) Patent No.: US 9,182,395 B2
(45) Date of Patent: Nov. 10, 2015

(54) METHOD FOR PRETREATING SPECIMEN AND METHOD FOR ASSAYING BIOLOGICAL SUBSTANCE

(75) Inventor: Hideji Tajima, Chiba (JP)

(73) Assignee: UNIVERSAL BIO RESEARCH CO., LTD., Chiba (JP)

( * ) Notice: Subject to any disclaimer, the term of this patent is extended or adjusted under 35 U.S.C. 154(b) by 19 days.

(21) Appl. No.: 13/132,041

(22) PCT Filed: Dec. 25, 2009

(86) PCT No.: PCT/JP2009/071678
§ 371 (c)(1),
(2), (4) Date: May 31, 2011

(87) PCT Pub. No.: WO2010/074265
PCT Pub. Date: Jul. 1, 2010

(65) Prior Publication Data
US 2011/0262919 A1  Oct. 27, 2011

(30) Foreign Application Priority Data

Dec. 25, 2008 (JP) .................................. 2008-331219
Jul. 28, 2009 (JP) .................................. 2009-175584

(51) Int. Cl.
| C12M 1/00 | (2006.01) |
|---|---|
| C12Q 1/68 | (2006.01) |
| C12M 1/34 | (2006.01) |
| C12M 3/00 | (2006.01) |
| G01N 15/06 | (2006.01) |
| G01N 21/64 | (2006.01) |
| G01N 33/52 | (2006.01) |
| G01N 33/00 | (2006.01) |
| G01N 33/543 | (2006.01) |
| G01N 35/02 | (2006.01) |
| G01N 35/10 | (2006.01) |

(52) U.S. Cl.
CPC ........ *G01N 33/54393* (2013.01); *C12Q 1/6804* (2013.01); *G01N 33/54326* (2013.01); *G01N 35/026* (2013.01); *G01N 35/1009* (2013.01); *Y10T 436/143333* (2015.01); *Y10T 436/25125* (2015.01)

(58) Field of Classification Search
CPC .......... C12Q 1/68; G01N 35/026; C12M 1/34
USPC ......... 435/6.1, 283.1, 287.1, 287.2; 422/68.1, 422/82.08, 430; 436/94, 175, 518
See application file for complete search history.

(56) References Cited

U.S. PATENT DOCUMENTS

| 4,477,346 | A | 10/1984 | Dickinson et al. |
|---|---|---|---|
| 4,680,274 | A | 7/1987 | Sakai et al. |
| 5,523,845 | A | 6/1996 | Honzawa et al. |
| 5,919,706 | A | 7/1999 | Tajima |
| 6,100,079 | A * | 8/2000 | Tajima ........................ 435/239 |
| 6,100,094 | A | 8/2000 | Tajima |
| 6,396,584 | B1 | 5/2002 | Taguchi et al. |
| 6,455,325 | B1 * | 9/2002 | Tajima ........................ 436/526 |
| 6,489,131 | B1 | 12/2002 | Wehner et al. |
| 6,492,192 | B1 * | 12/2002 | O'Toole et al. ................. 438/57 |
| 6,562,209 | B1 * | 5/2003 | Sullivan et al. ........... 204/403.01 |
| 6,632,655 | B1 * | 10/2003 | Mehta et al. ..................... 506/14 |
| 8,133,454 | B2 * | 3/2012 | Tajima ......................... 422/501 |
| 2001/0007770 | A1 | 7/2001 | Tajima |
| 2002/0123156 | A1 | 9/2002 | Tajima |
| 2003/0044323 | A1 | 3/2003 | Diamond et al. |
| 2003/0049857 | A1 * | 3/2003 | Chan ............................. 436/170 |
| 2005/0124076 | A1 | 6/2005 | Tseng et al. |
| 2006/0183217 | A1 | 8/2006 | Yanagida et al. |
| 2006/0194207 | A1 * | 8/2006 | Mitani et al. ....................... 435/6 |
| 2006/0257958 | A1 * | 11/2006 | Bruno .......................... 435/7.93 |
| 2007/0215554 | A1 * | 9/2007 | Kreuwel et al. ............... 210/695 |
| 2007/0248958 | A1 * | 10/2007 | Jovanovich et al. ............... 435/6 |
| 2008/0199930 | A1 * | 8/2008 | Lee et al. .................... 435/173.1 |
| 2008/0221372 | A1 * | 9/2008 | Rothmann et al. ................. 585/1 |
| 2009/0117620 | A1 * | 5/2009 | Fritchie et al. ............... 435/91.1 |
| 2009/0130745 | A1 * | 5/2009 | Williams et al. ........... 435/287.2 |
| 2009/0155123 | A1 * | 6/2009 | Williams et al. ................ 422/65 |
| 2010/0285996 | A1 * | 11/2010 | Tajima ............................ 506/27 |

FOREIGN PATENT DOCUMENTS

| EP | 0 724 156 A1 | 7/1996 |
|---|---|---|
| EP | 0768530 A1 | 4/1997 |
| EP | 0965842 A1 | 12/1999 |
| EP | 1304574 A2 | 4/2003 |
| JP | 60-256057 A | 12/1985 |
| JP | 63-196855 A | 8/1988 |
| JP | 4-221762 A | 8/1992 |
| JP | 5-506930 A | 10/1993 |
| JP | 1995-218423 | 8/1995 |
| JP | H08-62224 | 3/1996 |

(Continued)

OTHER PUBLICATIONS

Extended European Search Report issued in corresponding EP Appl. No. 09835061 on May 18, 2012.
Bjerner et al., "Immunometric Assay Interference: Incidence and Prevention", Clinical Chemistry, 48:4, 2002, pp. 613-621.

(Continued)

*Primary Examiner* — Narayan Bhat
(74) *Attorney, Agent, or Firm* — Birch, Stewart, Kolasch & Birch, LLP

(57) ABSTRACT

This invention relates to an assay device and a method for pretreating a specimen containing a biologically-relevant substance and then assaying the biologically-relevant substance. Biologically-relevant substances used in the assay method include microorganisms, cells, viruses, nucleic acids, polysaccharides, proteins (including antigens, antibodies, chromoproteins, and enzymes), peptides, nucleic acids, and small molecules. This pretreatment method removes contaminants from the biologically-relevant substances using supports such as magnetic particles, gels, resins, membranes, and solid-phased reagents. Therefore, in the assay method the following steps are generally carried out (i) a pretreatment step of treating a specimen using one or more first supports and then one or more second supports, and (ii) the assay step carried out after the pretreatment step. In particular, the pretreatment method reduces false positives and false negatives in the assay.

18 Claims, 48 Drawing Sheets

(56) References Cited

FOREIGN PATENT DOCUMENTS

| JP | 8-262024 A | | 10/1996 |
|---|---|---|---|
| JP | 11-344491 A | | 12/1999 |
| JP | 2004-317363 A | | 11/2004 |
| JP | 2005-502034 A | | 1/2005 |
| JP | 2007-263919 A | | 10/2007 |
| JP | WO2008/026670 | * | 3/2008 |
| JP | 2008-249738 A | | 10/2008 |
| WO | WO 91/17441 A1 | | 11/1991 |
| WO | WO 95/22605 A1 | | 8/1995 |
| WO | WO 96/41198 A1 | | 12/1996 |
| WO | WO 97/44671 A1 | | 11/1997 |
| WO | WO 00/43751 | | 7/2000 |
| WO | WO 2005/008255 A1 | | 1/2005 |

OTHER PUBLICATIONS

Bouillon et al., "Reduced frequency of blood donors with false-positive HIV-1 and -2 antibody EIA reactivity after elution of low-affinity nonspecific natural antibodies", Transfusion, vol. 42, Aug. 2002, pp. 1046-1052.

Covinsky et al., "An IgM λ Antibody to Escherichia coli Produces False-Positive Results in Multiple Immunometric Assays", Clinical Chemistry; 46:8, 2000, pp. 1157-1161.

International Search Report for PCT/JP2009/071678 dated Apr. 6, 2010.

Matsunaga et al., "Fully Automated Immunoassay for Detection of Prostate-specific Antigen Using Nano-Magnetic Beads and Micro-Polystyrene Bead Composites, 'Beads on Beads'", Analytica Chimica Acta, vol. 597, 2007, pp. 331-339.

* cited by examiner

Figure 3

ND OF ASSAYING
BIOLOGICAL SUBSTANCE

METHOD FOR PRETREATING SPECIMEN AND METHOD FOR ASSAYING BIOLOGICAL SUBSTANCE

This application is the National Stage of International Application No. PCT/JP2009/071678, filed in the Japanese Patent Office on Dec. 25, 2009. International Application PCT/JP2009/071678 in turn claims priority under 35 USC §119(a)-(d) of Japanese Application No. 2009-175584, filed in the Japanese Patent Office on Jul. 28, 2009 and of Japanese Application No. 2008-31219, filed in the Japanese Patent Office on Dec. 25, 2008.

TECHNICAL FIELD

The present invention relates to a method for pretreating a specimen containing a biologically-relevant substance before being subjected to an assay and a system for assaying the biologically-relevant substance in the specimen.

BACKGROUND ART

Since the method of preparing a monoclonal antibody was established, as a method for assaying a biologically-relevant substance of interest in a specimen, an immunoassay such as enzyme immunoassay has been employed as the main assay method. When using such an immunoassay, it is possible to perform direct assay because of its high specificity, and assay can be performed with high sensitivity. Further, recently, regarding these assay methods, steps from the step after setting a collected specimen to the step of obtaining assay results have been automated by the assay system. Further, in order to accelerate assay more, reagents in which concentrations of a solid-phased antibody and a conjugate are higher than ever before have been developed. However, when using reagents in more concentrated form, nonspecific reactions, which are conventionally unrelated at the time of assay, are often caused.

It is considered that causes of nonspecific reactions are the variety of target substances, the presence of immune analogs, the variety of antigens and the variety of antibodies. In the immunoassay system, as substances causing various nonspecific reactions, IgA-type, IgM-type and IgG-type heterophilic antibodies (antibodies that react between animals of different species: HAMA, anti-BSA antibody, etc.) and biological components (e.g., rheumatoid factor, cryoglobulin and M protein) are present, and there is a case where they show false positive in immunoassay as a result of a nonspecific reaction (see Non-patent documents 1, 2 and 3). Moreover, since cancer-associated antigens such as sugar chain exist on the surfaces of bacteria, in the case of infection caused by bacteria, false positive is often shown in cancer tests without cancer. Furthermore, there is a case where false positive is shown due to a nonspecific reaction caused, for example, by bacterial infection at the time of surgery for removing an organ from a cancer patient.

Further, a nonspecific reaction often occurs during pregnancy or when being affected with liver disease, kidney disease or the like. Moreover, recombinant antigens are used for many recently-developed reagents. It is known that due to the presence of bacterial components used at the time of preparation of these recombinant antigens, antibodies against these bacteria affect the assay system. In general, when performing immunoassay, inhibitors against these nonspecific reactive substances are added. However, since there is a limitation on the adding amounts for reagents, sufficient inhibitory effects are not necessarily obtained. Therefore, it is difficult for currently-used assay systems to remove nonspecific reaction factors and to sufficiently inhibit nonspecific reactions to perform assay.

PRIOR ART DOCUMENTS

[Non-patent document 1] Marlen Bouillon, et al., Reduced frequency of blood donors with false-positive HIV-1 and -2 antibody EIA reactivity after elusion of low-affinity nonspecific natural antibodies, TRANSFUSION, Volume 42, August 2002, 1046-1052

[Non-patent document 2] Johan Bjerner, et al., Incidence and Prevention, Clinical Chemistry, 48:4 613-621 (2002)

[Non-patent document 3] Michael Covinsky, et al., An IgMλ, Antibody to *Escherichia coli* Produces False-Positive Results in Multiple Immunometric Assays Michael Covinsky, Clinical Chemistry, 46:8 1157-1161 (2000)

DISCLOSURE OF THE INVENTION

Problems to be Solved by the Invention

The present invention was made in consideration of the above-described circumstances. The purpose of the present invention is to provide a pretreatment method in which a contaminant can be removed in advance from a specimen to be subjected to an assay and an assay method using the pretreated specimen.

Means for Solving the Problems

The present inventor diligently made researches in order to solve the above-described problems and found that a biologically-relevant substance can be highly sensitively assayed when the assay is carried out after pretreating a specimen. Thus the present invention was achieved. That is, the present invention relates to a system for assaying a biologically-relevant substance in a specimen, comprising:

a first support to which a substance having affinity to a contaminant contained in the specimen, a substance that inactivates the contaminant, or a substance having affinity to the biologically-relevant substance in the specimen is immobilized; and a second support selected from a support to which a reagent for detecting the biologically-relevant substance is immobilized and a support made of a solid-phased reagent for detecting the biologically-relevant substance.

In the present invention, the biologically-relevant substance may be an antigen or antibody or a nucleic acid.

Further, the contaminant in the specimen may be a nonspecific reaction factor. The nonspecific reaction factor may be at least one selected from the group consisting of an immunoglobulin, an M protein, a heterophilic antibody and a rheumatoid factor.

The first support is, for example, at least one selected from the group consisting of magnetic particles, a gel, a resin and a membrane. Further, the magnetic particles are preferably capable of being held in a dispensing chip attached to a dispensing nozzle. In this case, a treatment such as separation, washing and suspension is preferably carried out in the dispensing chip using the magnetic particles.

Further, the reagent for detecting the biologically-relevant substance preferably comprises a labeled antigen or a labeled antibody against the biologically-relevant substance or a primer and a probe for amplifying the biologically-relevant substance.

In one embodiment of the present invention, solid-phasing of the reagent for detecting is preferably carried out by freeze-drying (lyophilization).

Further, the specimen, the first support and the second support are preferably held in different holding portions such as wells and chips respectively.

Moreover, the system of the present invention is characterized in that a holding portion (well or chip) in which the specimen is held, a holding portion in which the first support is held and a holding portion in which the second support is held are arranged in an approximate straight line.

Further, the system of the present invention is characterized in that the specimen holding portion in which the specimen is held, the holding portion in which the first support is held and the holding portion in which the second support is held are integrated into a cartridge.

In the above-described system, the holding portions are preferably sealable.

Moreover, the cartridge of the present invention is characterized in that it comprises: a holding portion, in which a first support to which a substance having affinity to a contaminant contained in a specimen, a substance that inactivates the contaminant, or a substance having affinity to the biologically-relevant substance in the specimen is immobilized is held in advance; a holding portion, in which a second support selected from a support to which a reagent for detecting the biologically-relevant substance is immobilized and a support made of a solid-phased reagent for detecting the biologically-relevant substance is held; and a specimen holding portion in which the specimen is held.

In the above-described cartridge, the first support is preferably magnetic particles.

Further, in this cartridge, solid-phasing is preferably carried out by freeze-drying.

In this cartridge, the holding portions may be sealable.

Moreover, this cartridge is characterized in that the specimen holding portion in which the specimen is held, the holding portion in which the first support is held and the holding portion in which the second support is held are arranged in an approximate straight line.

The pretreatment method of the present invention is a method for pretreating a specimen before assaying a biologically-relevant substance in the specimen, comprising a step of treating the specimen using a first support to which a substance having affinity to a contaminant contained in the specimen, a substance that inactivates the contaminant, or a substance having affinity to the biologically-relevant substance in the specimen is immobilized.

Moreover, the pretreatment method of the present invention is characterized in that it further comprises a step of preparing a second support selected from a support to which a reagent for detecting the biologically-relevant substance is immobilized and a support made of a solid-phased reagent for detecting the biologically-relevant substance.

In the above-described pretreatment method, the biologically-relevant substance may be an antigen or antibody or a nucleic acid.

Examples of the contaminant include a nonspecific reaction factor.

Further, the nonspecific reaction factor may be at least one selected from the group consisting of an immunoglobulin, an M protein, a heterophilic antibody and a rheumatoid factor.

The first support is, for example, at least one selected from the group consisting of magnetic particles, a gel, a resin and a membrane.

Further, the reagent for detecting the biologically-relevant substance preferably comprises a labeled antigen or a labeled antibody against the biologically-relevant substance or a primer and a probe for amplifying the biologically-relevant substance.

Further, in the pretreatment method, solid-phasing is preferably carried out by freeze-drying.

Moreover, in the present invention, the pretreated specimen may be provided to an assay device to assay the biologically-relevant substance in the specimen.

Further, the assay is preferably an immunoassay or an assay by means of a nucleic acid amplification method.

Examples of the nucleic acid amplification method include a PCR method and an isothermal amplification method. At the time of amplification of a nucleic acid, a mixture of a target nucleic acid-containing solution and an amplification reagent is preferably held in a holding portion such as a well and a chip and sealed with a hydrophobic fluid such as a mineral oil.

In the present invention, the pretreatment of the specimen and the assay of the treated specimen can be carried out successively.

Moreover, the nucleic acid amplification device of the present invention is characterized in that it comprises:
(a) a specimen holding portion in which a specimen is held;
(b) a first holding portion in which trapping particles for trapping a target nucleic acid from the specimen are held;
(c) a second holding portion in which a reagent for detecting the target nucleic acid is held;
(d) a dispensing mechanism for dispensing the specimen into the specimen holding portion, a mechanism for mixing the specimen with the trapping particles to extract the target nucleic acid from the specimen, and a mechanism for mixing the extracted target nucleic acid with the reagent for detecting; and
(e) a mechanism selected from the group consisting of: a mechanism for pouring a hydrophobic fluid, which has a specific gravity smaller than that of a mixed fluid of the target nucleic acid and the reagent for detecting, into the second holding portion; a mechanism for removing or putting lids for covering the respective holding portions; a mechanism for irradiating an irradiating light for letting the target nucleic acid fluoresce; a mechanism for receiving a light from the target nucleic acid irradiated with the irradiating light to detect the target nucleic acid; and a mechanism in which the mechanisms are combined.

Advantageous Effect of the Invention

According to the present invention, a biologically-relevant substance can be assayed with significantly high sensitivity.

In the conventional systems for assaying a specimen, a biologically-relevant substance is assayed with a contaminant being not sufficiently removed from the specimen. According to the present invention, the contaminant can be removed and it is possible to increase sensitivity at the time of assaying the biologically-relevant substance. Further, according to the present invention, the pretreatment of the specimen and the assay of the biologically-relevant substance in the pretreated specimen can be carried out automatically and successively. Moreover, in the conventional systems, it is required to manually add a reagent that deactivates a contaminant to a specimen to be assayed in order to avoid intervention of the contaminant, but according to the present invention, it is no longer necessary to manually add such a reagent. Therefore, assay results can be very conveniently obtained.

BRIEF DESCRIPTION OF THE DRAWINGS

FIG. 3 is an explanatory drawing for schematically showing an embodiment in which a contaminant is decomposed using a substance that decomposes the contaminant.

BEST MODE FOR CARRYING OUT THE INVENTION

1. Summary

The present invention relates to a system for assaying a specimen utilizing a plurality of types of supports having different functions and a method for pretreating the specimen for the purpose of assaying a target substance in the specimen. The assay system of the present invention can be used for a specimen containing a biologically-relevant substance. The specimen is treated with a plurality of supports having different functions and the biologically-relevant substance as a target is assayed with high accuracy. As the plurality of supports having different functions, for example, it is possible to use: a first support to which a substance having affinity to a contaminant contained in the specimen, a substance that inactivates the contaminant, or a substance having affinity to the biologically-relevant substance in the specimen is immobilized; and a second support selected from a support to which a reagent for detecting the biologically-relevant substance is immobilized and a support made of a solid-phased reagent for detecting the biologically-relevant substance. "Having affinity" means that substances (substances A and B) chemically or physically interact with each other to enhance bonding thereof. Further, to "inactivate" means that possessed functions are inhibited. As combinations of the substance A and the substance B having affinity to the substance A, for example, an antigen and an antibody, a ligand and a receptor, a nucleic acid and a complementary strand thereof, etc. are exemplified. Examples of the first support for removing the contaminant include a support having a substance (e.g., magnetic particles, a column, a filtering material, a polymeric material, etc.) to which an antibody against a nonspecific reaction factor is immobilized. Further, examples of the first support for decomposing the contaminant include a support having a reducing agent for decomposing the nonspecific reaction factor. Further, examples of the first support for extracting the biologically-relevant substance include magnetic particles to which a probe having affinity to a nucleic acid as the biologically-relevant substance is immobilized. By utilizing these exemplified first supports, removal of the contaminant from the specimen and extract of the biologically-relevant substance from the specimen can be carried out.

Figure 1:
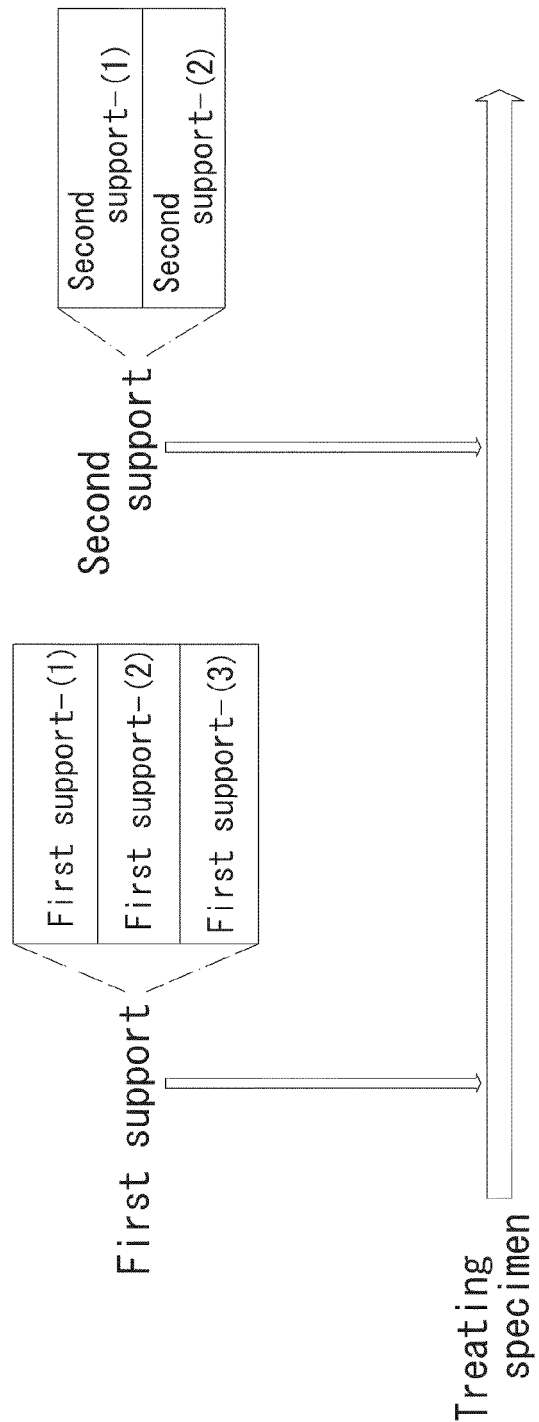
FIG. 1 is an explanatory drawing exemplifying combinations of a first support and a second support.

As shown in FIG. 1, as the first support, the following three types of supports are exemplified: a support to which a substance having affinity to a contaminant contained in a specimen is immobilized; a support to which a substance that inactivates the contaminant is immobilized; and a support to which a substance having affinity to a biologically-relevant substance in the specimen is immobilized. As the second support, the following two types of supports are exemplified: a support to which a reagent for detecting the biologically-relevant substance is immobilized; and a support made of a solid-phased reagent for detecting biologically-relevant substance. Therefore, it is considered that the number of combinations of the first support and the second support is at least 6. By treating the specimen using these combinations, various treatment embodiments can be formed.

Figure 2:
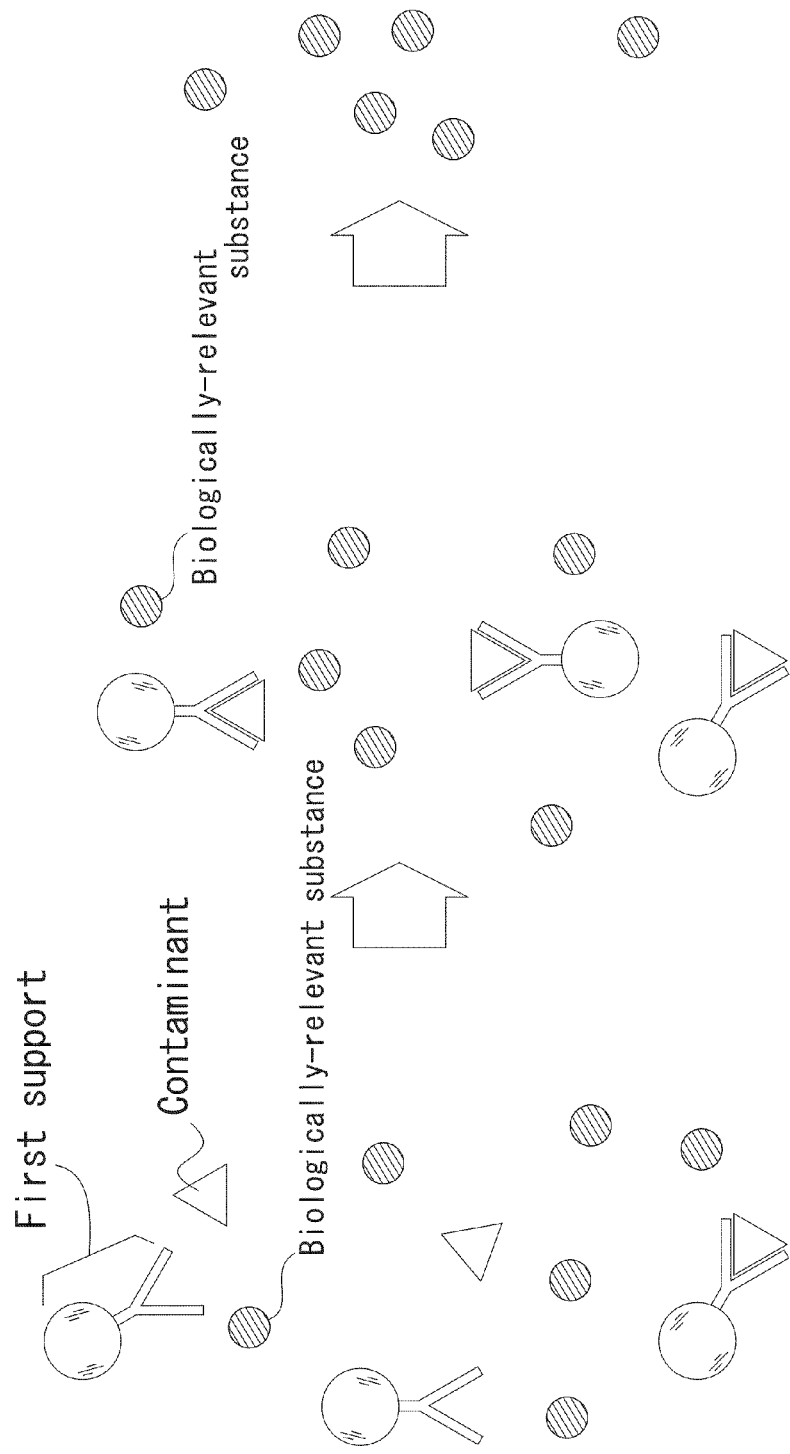
FIG. 2 is an explanatory drawing for schematically explaining an embodiment in which a contaminant is removed using a first support to which a substance having affinity to the contaminant is immobilized.
Figure 3:
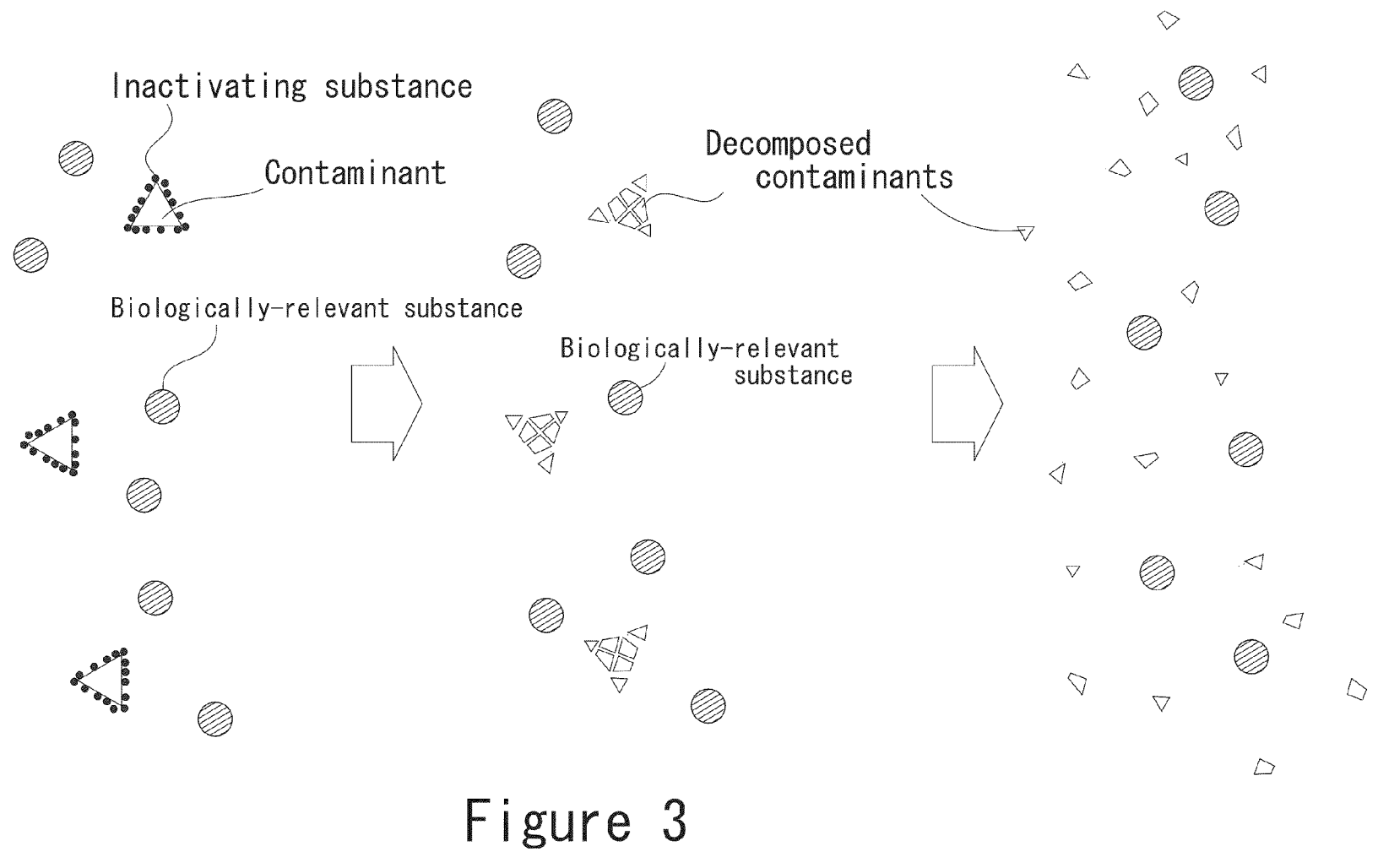
Figure 4:
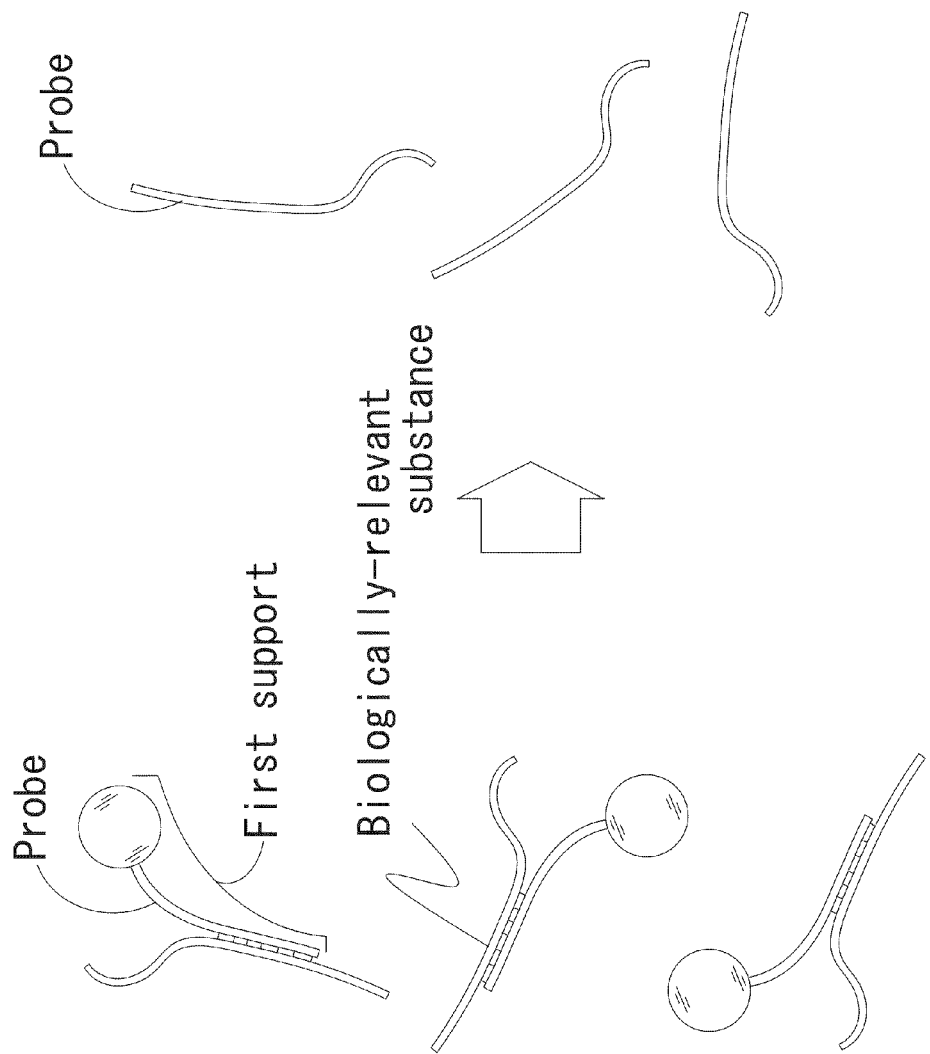
FIG. 4 is an explanatory drawing for schematically explaining an embodiment in which a biologically-relevant substance is extracted using a first support to which a substance having affinity to the biologically-relevant substance is immobilized.

FIGS. 2-5 are explanatory drawings for schematically explaining the principle of the system of the present invention. For example, as shown in FIG. 2, by treating a specimen using a support to which a substance having affinity to a contaminant contained in the specimen is immobilized as a first support, the support traps the contaminant, and by collecting (removing) the support, the contaminant can be removed from the specimen. Further, as shown in FIG. 3, by utilizing a support to which a substance that inactivates a contaminant contained in a specimen (inactivating substance) is immobilized, as a first support, the contaminant in the specimen can be decomposed, and as a result, the contaminant can be removed from the specimen. After obtaining a biologically-relevant substance, by using a support to which a reagent for detecting the biologically-relevant substance is immobilized as a second support, the biologically-relevant substance in the specimen can be detected. Further, as shown in FIG. 4, by using a support to which a substance having affinity to the biologically-relevant substance in the specimen is immobilized as a first support, only the biologically-relevant substance can be extracted from the specimen, and it is possible to prevent inhibition by the contaminant at the time of assay of the biologically-relevant substance, etc.

In the present invention, as shown in FIG. 1, it is also possible to employ combinations of a first support and a second support other than those exemplified above. Depending on respective combinations, different treatments can be applied to the specimen. Further, after using the first support to which the substance having affinity to the contaminant is immobilized, the specimen can be further treated using the first support to which the substance having affinity to the biologically-relevant substance is immobilized.

After obtaining the biologically-relevant substance using the first support, the biologically-relevant substance can be assayed using the second support. The first support is a support for highly purifying or extracting the biologically-relevant substance in the specimen, and is used for the pretreatment of the present invention. The second support is a support to which an assay reagent for detecting the biologically-relevant substance is immobilized, or a support made of the solid-phased reagent. In the present invention, an assay step can be carried out by separately performing a reaction with the reagent without preparing the second support. However, in consideration of total automation using an apparatus, the second support is preferably prepared in advance. Further, by preparing not only the second support but also the first support in advance, more convenient operation with higher efficiency can be realized.

Figure 5:
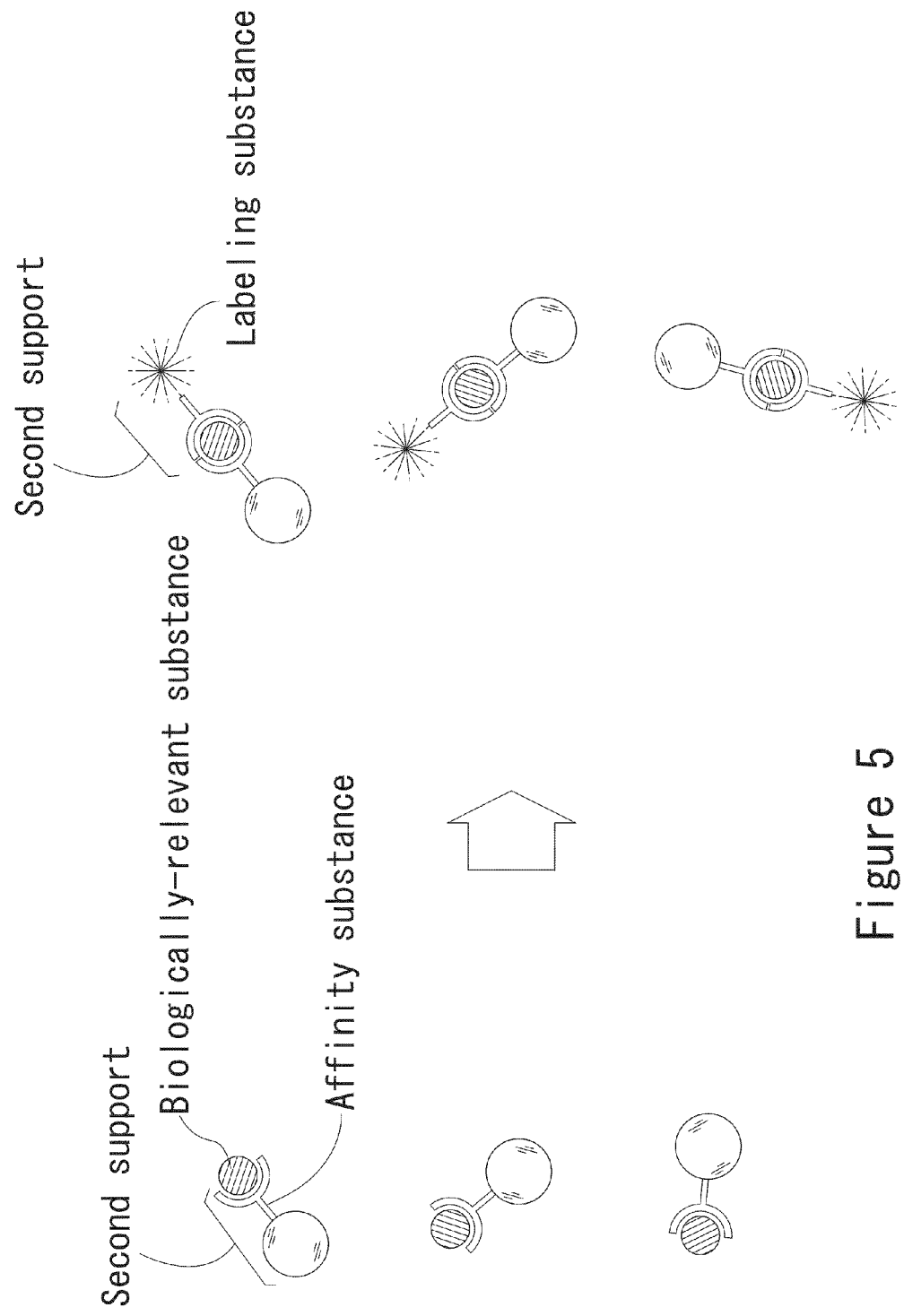
FIG. 5 is an explanatory drawing for schematically explaining an embodiment in which a biologically-relevant substance is extracted and labeled using a second support to which a substance having affinity to the biologically-relevant substance is immobilized.

As shown in FIG. 5, the second support to which the substance having affinity to the biologically-relevant substance (affinity substance) is immobilized is bound to the biologically-relevant substance, and the second support to which a labeling substance is immobilized is bound to the biologically-relevant substance, thereby detecting the biologically-relevant substance. When using the first support having affinity to the biologically-relevant substance, there is a case where use of the second support having affinity to the biologically-relevant substance can be omitted. In this case, for a specimen treated using the first support, the second support to which the labeling substance is immobilized can be used immediately.

Further, the pretreatment method of the present invention is a method for pretreating a specimen before assaying a biologically-relevant substance in the specimen, characterized in that it comprises a step of treating the specimen using a first support to which a substance having affinity to a contaminant contained in the specimen, a substance that inactivates the contaminant, or a substance having affinity to the biologically-relevant substance in the specimen is immobilized. The pretreatment means both removing the contaminant contained in the specimen and extracting or purifying the biologically-relevant substance contained in the specimen.

The pretreatment of the present invention may further comprise a step of preparing a second support to which a substance having affinity to a biologically-relevant substance and/or a substance for labeling the biologically-relevant substance is immobilized. The preparation of the second support can be carried out simultaneously with or before or after the treatment using the first support. When the biologically-relevant substance is an antigen or antibody, preparation for labeling and detecting an antibody or antigen in a subsequent assay step is completed. When the biologically-relevant substance is a nucleic acid, preparation for labeling and detecting a nucleic acid in a subsequent step is completed.

After carrying out the pretreatment described above, the assay step is carried out. When the biologically-relevant substance as an assay target is an antigen or antibody, examples of the first support include holding bodies, such as magnetic particles, a gel and a membrane, to which a substance having affinity to a contaminant in a specimen is immobilized, and examples of the second support include a substance (e.g., magnetic particles and beads) to which an antibody against the antigen is immobilized.

Further, when the biologically-relevant substance is a nucleic acid such as a DNA and RNA, examples of the first support include a support to which a substance having affinity to a DNA/RNA in a specimen is immobilized, and examples of the second support include a support made of a solid-phased reaction reagent (e.g., probe, primer and master mixture) required for amplifying and assaying a specific portion of a nucleotide sequence of a DNA/RNA extracted, separated or purified.

More specifically, for example, when the biologically-relevant substance is a tumor marker (e.g., CA19-9), in order to prevent a false-positive reaction at the time of assay, as a first support, a support (magnetic particles or a nonmagnetic solid) to which a substance that binds to a contaminant for removing a reaction-inhibiting substance such as IgM (e.g., IgM antibody) is immobilized is used. Further, as a second support, a magnetic or nonmagnetic solid to which a tumor marker antibody (e.g., anti-CA19-9 antibody) is immobilized is used. The assay is performed by adding the biologically-relevant substance (CA19-9 in the example above) treated using the first support and a substrate solution to a container containing the second support.

When the biologically-relevant substance as the assay target is a nucleic acid (e.g., influenza virus RNA), as the first support, magnetic particles for extracting, separating or purifying a virus RNA are used, and as the second support, a support comprising a reaction reagent required for amplifying and assaying (e.g., PCR) a specific portion of a nucleotide sequence of the above-described RNA extracted, separated or purified is used. The assay is performed by adding the biologically-relevant substance (influenza virus RNA in the example above) treated using the first support and the reaction reagent for amplification to a container containing the second support.

In one embodiment of the present invention, the treatment for removing the nonspecific reaction factor in the specimen and the treatment for preparing the second support to which a substance having affinity to the biologically-relevant substance and/or labeling the biologically-relevant substance is immobilized are carried out successively in one apparatus. An apparatus realizing this is called an assay system in the present invention.

Figure 6:
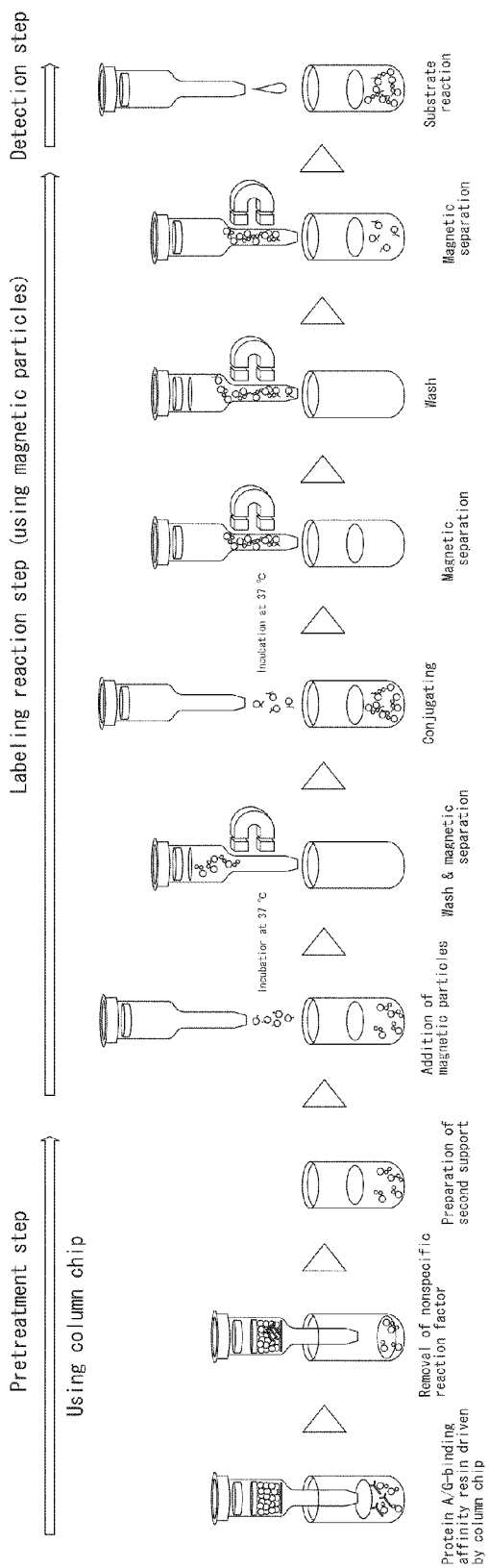
FIG. 6 is an explanatory drawing for schematically showing all the steps from pretreatment using magnetic particles to which an antibody against a nonspecific reaction factor is immobilized to detection of an antigen contained in a specimen.

As shown in FIG. 6, in the assay system, as a pretreatment step, a step of treating a specimen containing a biologically-relevant substance, such as a step of removing a contaminant, and a step of preparing a second support are carried out. A step of detecting the biologically-relevant substance in the specimen has a labeling reaction step for labeling the biologically-relevant substance in the specimen and an assay step for assaying the labeled biologically-relevant substance. Therefore, broadly speaking, in the assay system, the following 3 steps are carried out: (i) a step of treating a specimen using a first support; (ii) a step of preparing a second support: and (iii) an assay step carried out after a pretreatment. Basically, the step (i) is called a pretreatment. But the pretreatment step may be a combination of the step (i) and the step (ii). It is understood that the step (i) is a treatment for creating an environment in a test tube for highly purifying or extracting a biologically-relevant substance as an assay target, and that the step (ii) is for creating an environment in a test tube containing a reagent for detecting the biologically-relevant substance. It means a kind of step for preparing a sample and a reagent for assaying the sample for the purpose of allowing the biologically-relevant substance in the specimen to be assayed. In FIG. 6, preparation of the second support is included in the pretreatment step.

The step of treating the specimen using the first support means a step of removing a contaminant and a step of highly purifying or extracting the biologically-relevant substance. This step can be suitably selected depending on the preparation of the second support. For example, techniques such as: (a) a technique of selectively collecting a desired biologically-relevant substance utilizing magnetic particles; and (b) a technique of simultaneously collecting a plurality of types of biologically-relevant substances desired can be employed. When a biologically-relevant substance as a detection target is a protein such as an antigen and an antibody, mainly the following embodiments can be employed: (1) a technique of trapping and removing a nonspecific reaction factor utilizing magnetic particles to which an antibody against the nonspecific reaction factor is immobilized; (2) a technique of trapping and removing a nonspecific reaction factor utilizing an affinity gel to which an antibody against the nonspecific reaction factor is immobilized; (3) a technique of trapping and removing a nonspecific reaction factor utilizing a filter to which an antibody against the nonspecific reaction factor is immobilized; (4) a technique of trapping and removing a nonspecific reaction factor utilizing a plastic support to which an antibody against the nonspecific reaction factor is immobilized; and (5) a technique of decomposing a nonspecific reaction factor using a gel to which a reducing agent is immobilized. When the biologically-relevant substance is a nucleic acid such as a DNA and RNA, for example, a technique of extracting a target nucleic acid using magnetic particles to which a probe that can bind to the target nucleic acid is immobilized can be employed.

In the assay system of the present invention, the pretreatment step is carried out and then an assay such as an immunoassay and a nucleic acid assay can be carried out successively. The assay system has a nozzle, a pipette chip as a dispensing chip, a holding portion such as a well plate in which a plurality of wells are arranged, a pump mechanism, etc. In the holding portion, a solution of magnetic particles, a washing solution, an enzyme-labeling solution, a substrate solution, etc. can be held. The movement of the pipette chip can be automatically controlled by a motor, a motor controller, etc. The material of the well may be suitably selected in view of the detection method. For example, in the case of performing CLIA or CLEIA, the well may be made of an opaque material which is not affected by mutual luminescence, and in the case of performing EIA (ELISA), the well may be made of a transparent material because a transmitted light is handled. As described hereinbelow, magnetic particles for trapping a nonspecific reaction factor mean, for example, a magnetic substance, which has a surface to which an antibody against the nonspecific reaction factor can be immobilized, and which is for performing B/F separation (separation of a bound body and a free body), etc.

Figure 7:
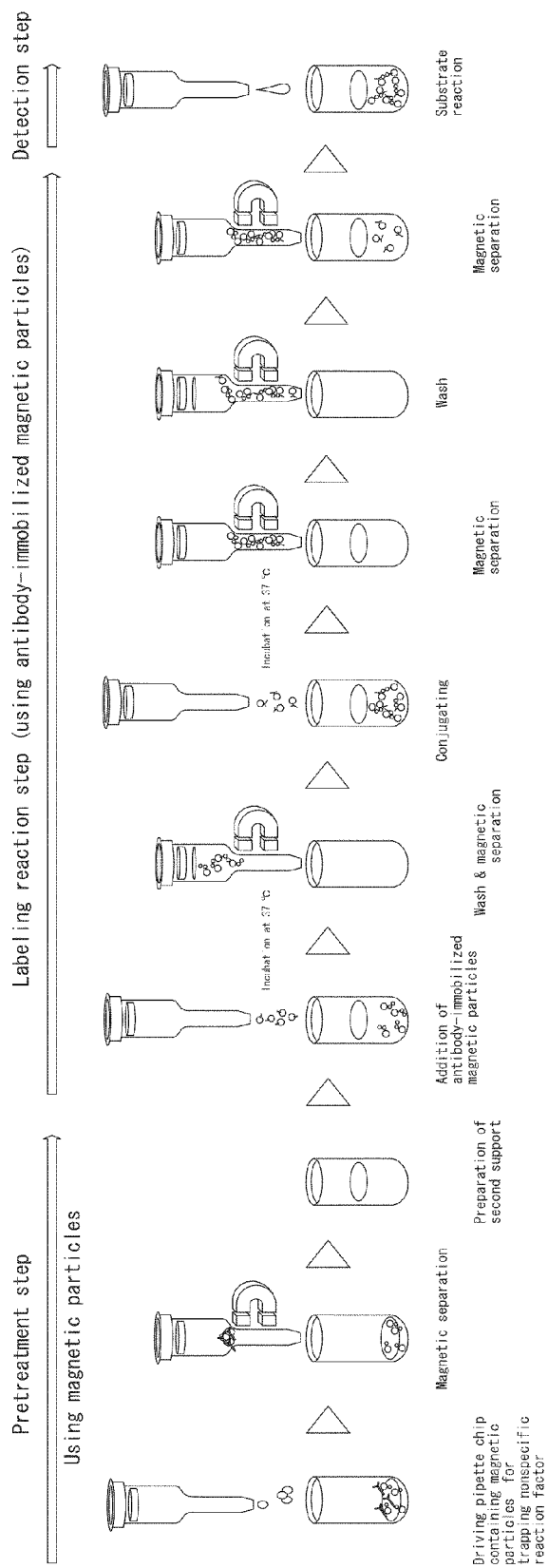
FIG. 7 is an explanatory drawing for schematically showing all the steps from pretreatment using a support to which an antibody against a nonspecific reaction factor is immobilized to detection of an antigen contained in a specimen.

FIG. 6 shows an entire process in which a specimen is treated using a technique of trapping and removing a nonspecific reaction factor utilizing an affinity gel to which an antibody against the nonspecific reaction factor is immobilized, and then a biologically-relevant substance is labeled using a technique of selectively collecting a desired biologically-relevant substance utilizing magnetic particles. Note that timing of the preparation of the second support is not required to be the same as that shown in FIG. 6. The preparation of the second support may be carried out during or before the step of removing a contaminant. FIG. 7 shows a case of carrying out different treatments according to an embodiment different from that shown in FIG. 6. FIG. 7 shows an entire process in which a specimen is pretreated using a technique of trapping and removing a nonspecific reaction factor utilizing magnetic particles to which an antibody against the nonspecific reaction factor is immobilized, and then a biologically-relevant substance is detected using a technique of selectively collecting a desired biologically-relevant substance utilizing magnetic particles. When the biologically-relevant substance as an assay target is a nucleic acid, before a step of assaying a target nucleic acid in a specimen, a step of extracting a nucleic acid using a first support is carried out. Hereinafter, the respective steps such as the pretreatment step and the assay step, etc. will be described in more detail.

2. Biologically-Relevant Substance and Specimen

In the present invention, the "biologically-relevant substance" is a substance which can be a detection target in the assay step, and means every biological substance such as a microorganism, a virus, a cell, a nucleic acid, a polysaccharide, a simple protein, a complex protein and a low-molecular substance.

The microorganism includes a fungus, a *eubacterium* and an *archaebacterium*. Examples of the fungus include microorganisms belonging to the genus *Saccharomyces*, the genus *Aspergillus* and the genus *Candida*. Examples of the *eubacterium* include microorganisms belonging to the genus *Mycobacterium*, the genus *Escherichia*, the genus *Bacillus*, the genus *Listeria*, the genus *Vibrio*, the genus *Salmonella*, the genus *Pseudomonas*, the genus *Staphylococcus*, the genus *Mycoplasma*, the genus *Rickettsia* and the genus *Chlamydia*. Examples of the *archaebacterium* include microorganisms belonging to the genus *Thermoplasma*, the genus *Halobacterium* and the genus *Methanobacterium*. Specific examples thereof include *Saccharomyces cerevisiae*, *Aspergillus nidulans*, *Candida albicans*, *Mycobacterium tuberculosis*, *Mycobacterium avium*, *Mycobacterium intracellulare*, *Mycobacterium kansasii*, *Escherichia coli*, *Bacillus cereus*, *Bacillus anthracis*, *Listeria monocytogenes*, *Vibrio parahaemolyticus*, *Vibrio cholerae*, *Salmonella typhi*, *Pseudomonas aeruginosa*, *Staphylococcus aureus*, *Mycoplasma pneumoniae*, *Rickettsia prowazekii* and *Chlamydia trachomatis*.

Examples of the virus include viruses belonging to Adenoviridae, Bacteriophage and Retroviridae. Specific examples thereof include adenovirus, T7-like virus, hepatitis B virus, hepatitis C virus, human immunodeficiency virus, norovirus, human rota virus and influenza virus. Examples of the cell include an animal cell, a plant cell and an insect cell. Examples of the nucleic acid include a DNA, a RNA and an artificial nucleic acid. Examples of the polysaccharide include starch, glycogen, chitin and carrageenan. Examples of the protein include an antigen, an antibody, an enzyme, a chromoprotein and other polypeptides. Examples of the low-molecular substance include nucleotides such as nucleotide triphosphate and deoxynucleotide triphosphate, saccharides such as glucose and galactose, amino acids such as glutamic acid and lysine, dyes such as fluorescein and ethidium bromide, and hormones such as epinephrine, peptide hormone and steroid. Note that the above-described biologically-relevant substances are just examples and the present invention is not limited to these substances. The specimen is not particularly limited as long as it contains such a biologically-relevant substance. The specimen includes, for example, (i) clinical materials such as sputum, expectorated sputum, saliva, mouthwash, stomach fluid, pleural lavage solution, blood, serum, plasma, feces, urine, spinal fluid and semen, (ii) biological materials such as cell lysate, tissue lysate, cell culture and tissue culture, (iii) effluents such as household effluent and industrial effluent, (iv) environmental water such as seawater, river water, pond water, lake water and groundwater, and (v) drinking water, washing solution for food, etc. and washing solution for tool in which a biologically-relevant substance may be present. The "washing solution for tool in which a biologically-relevant substance may be present" means a washing solution for a tool by which a portion to be confirmed whether or not a biologically-relevant substance is present is wiped, or a washing solution by which a portion to be confirmed whether or not a biologically-relevant substance is present is washed. Examples thereof includes a washing solution for a kitchen knife and a washing solution for a wiping cloth (a cloth for wiping the table) after used for wiping a thing.

In the present invention, various types of nonspecific reaction factors which are removed by the treatment of removing the contaminant are considered depending on the type of the specimen to be treated. When serum is used as the specimen, an immunoglobulin, a heterophilic antibody, a rheumatoid factor (RF) an M protein or the like may be the nonspecific reaction factor. The M protein is synonymous with a monoclonal immunoglobulin and means a protein observed when one type of immunoglobulin is increased. For example, an immunoglobulin protein produced by myeloma is an M protein which appears in serum of a patient suffering from plasma cell dyscrasia typified by multiple myeloma. Depending on the type of myeloma producing M protein, M proteins are classified into 5 types, i.e., IgA, IgM, IgG, IgE and Bence-Jones protein. The heterophilic antibody (HA) is a human anti-animal antibody and is usually present in a healthy human at a rate of several percent. Examples of the heterophilic antibody include a human anti-mouse antibody (HAMA), a human anti-sheep antibody (HASA) and a human anti-goat antibody (HAGA). When such a heterophilic antibody is present in a specimen, false-positive or false-negative nonspecific reaction is observed in immunoassay using a mouse, goat, sheep or goat antibody. When a nucleic acid is to be detected from a specimen, the nucleic acid of interest can be detected using a complementary region of the nucleic acid or a nucleic acid comprising the complementary region instead of an antibody. For nucleic acid amplification used at the time of detection, for example, a PCR method can be applied, but there is no limitation thereon. Another suitable amplification method (an isothermal amplification method such as a LAMP method) may be used according to purpose.

3. Treatment of Specimen Using First Support

When using this treatment, the nonspecific reaction factor that causes a false-positive reaction or false-negative reaction, which cannot be avoided by a conventional method in the field of immunoassay, can be removed in advance. Therefore, the biologically-relevant substance can be detected very specifically with high sensitivity. As the first support, magnetic particles, a gel-like member, a membrane, a resin member, corpus fibrosum or the like can be utilized, and they may be suitably selected according to need. As described hereinbelow, after the treatment of removing the contaminant, the treated specimen is provided to an immunoassay step. Further, by this treatment, in the field of nucleic acid assay, a target nucleic acid can be selectively extracted, and detection sensitivity at the time of assay can be improved. As the first support, it is possible to use magnetic particles or the like to which a probe for trapping a nucleic acid is immobilized.

Figure 8:
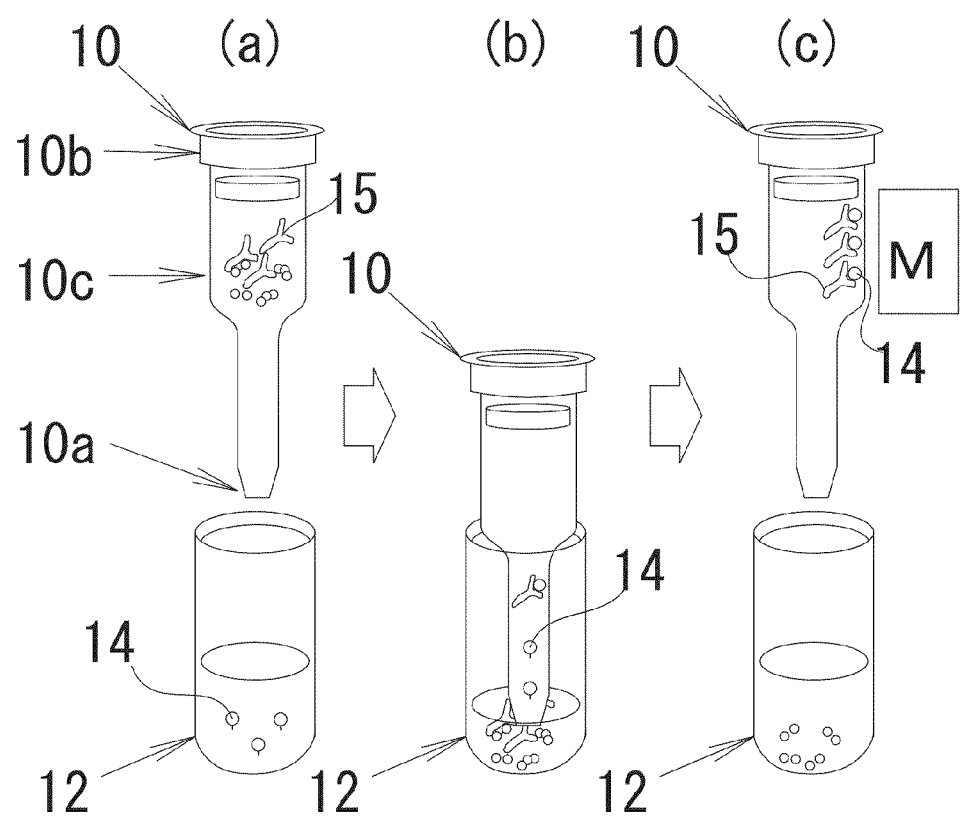
FIG. 8 is an explanatory drawing for explaining a treatment of removing a contaminant using magnetic particles to which an antibody against a nonspecific reaction factor is immobilized.

3-1. Treatment of Removing Contaminant Using Magnetic Particles to which Antibody Against Nonspecific Reaction Factor is Immobilized FIG. 8 shows a treatment of removing a contaminant using magnetic particles to which an antibody against a nonspecific reaction factor is immobilized. As shown in FIG. 8, a pipette chip (dispensing chip) 10 is formed, for example, into an approximate elongated cylindrical shape which is tapered, and is detachably attached to the assay system. The magnetic particles are used, for example, when separation, washing, suspension or the like is carried out in the pipette chip attached to a dispensing nozzle. As shown in FIG. 8(a), the pipette chip 10 has a tip portion 10a which is inserted into a well 12, a mounting portion 10b which is fixed to a nozzle of the assay system (not shown) and a holding portion 10c which is formed between the tip portion 10a and the mounting portion 10b and holds magnetic particles utilizing an external magnetic field. The inner diameter of the tip portion 10a is smallest. The holding portion 10c consists of, for example, a smaller diameter portion and a larger diameter portion. The inner diameter of the smaller diameter portion is larger than the inner diameter of the tip portion, and the inner diameter of the larger diameter portion is smaller than the inner diameter of the mounting portion. Further, the inner diameter of the mounting portion 10b is largest. It is desirable that the volume of the pipette chip be suitably determined depending on the size of the well. For example, when the volume is in the range of several microliters to several hundred microliters, convenience may be improved.

The assay system for performing the treatment of removing the contaminant has a magnet M, which is provided to the outer circumference of the holding portion 10c to be allowed to move toward and away from the outer circumference and constrains magnetic particles by magnetic force, a nozzle to which the mounting portion 10b of the pipette chip 10 is attached, a pump mechanism for allowing the pipette chip 10 attached to the nozzle to suck up or discharge a liquid, etc. In this regard, the magnet M can constrain magnetic particles at the smaller diameter portion of the holding portion 10c (see FIGS. 6 and 7).

As shown in FIG. 8(b), when the pipette chip 10 is inserted into the well 12, for example, a clearance of about 0.2 mm to 0.5 mm is provided between the pipette chip 10 and the well 12. By providing this, the contact area between the specimen and the outside at the time of insertion of the pipette chip can be decreased as much as possible, and risk of contamination is reduced. The shape of the pipette chip 10 may be suitably changed, but the clearance between the well 12 and the pipette chip 10 at the time of insertion of the pipette chip 10 into the well 12 is preferably narrower.

A magnetic particle 14 has magnetic property, and the size thereof is, for example, about 0.1 to 100 μm, and preferably about 0.1 to 10 μm. The size, mass, materials, structure, properties (paramagnetic property, superparamagnetic property, ferromagnetic property, ferrimagnetic property, level of magnetic force), etc. of the magnetic particle 14 may be arbitrarily determined according to the purpose of the treatment. The magnetic particle can be formed using iron hydroxide, iron oxide hydrate, iron oxide, mixed iron oxide, iron, γ-$Fe_2O_3$, $Fe_3O_4$, etc.

Figure 9:
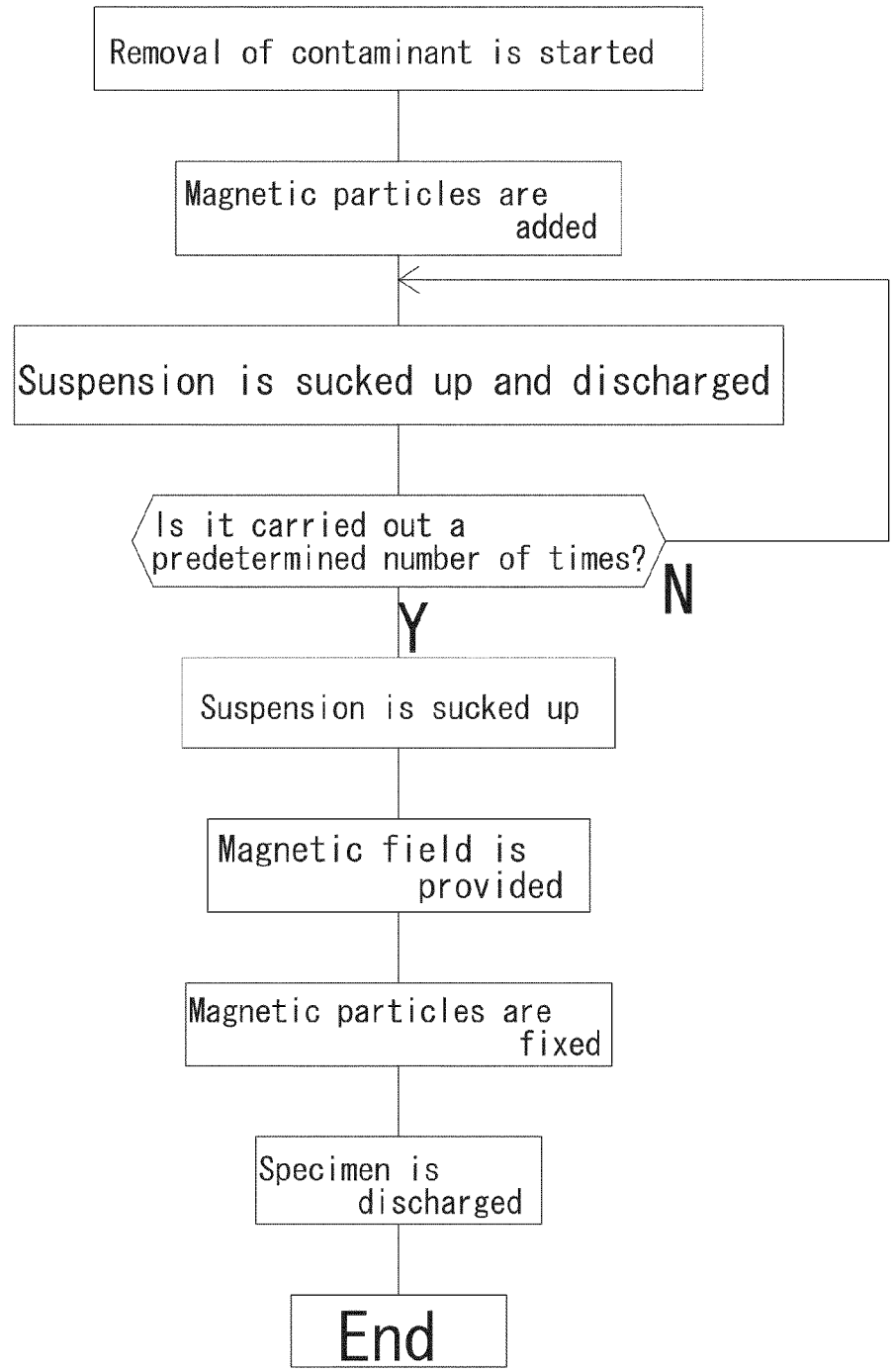
FIG. 9 is a flow chart of a treatment of removing a contaminant using magnetic particles to which an antibody against a nonspecific reaction factor is immobilized.

FIG. 9 is a flow chart of a treatment of removing a contaminant using magnetic particles to which an antibody against a nonspecific reaction factor is immobilized. As shown in FIG. 9, when the assay system performs a pretreatment of a specimen using the above-described well and pipette chip, firstly, a predetermined amount of the specimen held in a well is sucked up by the pipette chip 10. Next, the pipette chip 10 into which the specimen is sucked up is moved to the well 12 in which a solution of magnetic particles for pretreatment is held, and the specimen in the pipette chip 10 is discharged into the well 12 in which the solution of magnetic particles for pretreatment is held. Using the pipette chip 10, the operation of mixing the specimen and the solution of magnetic particles for pretreatment is repeated, and flow stirring is carried out by sucking up and discharging, thereby producing a homogeneous suspension. It is allowed to stand for required time after stirring is completed, and a nonspecific reaction factor in the specimen is allowed to be bound to an antibody against the nonspecific reaction factor immobilized to the magnetic body for pretreatment. After a predetermined time passes, a step of sucking up the suspension allowed to stand into the pipette chip 10 is carried out.

As shown in FIG. 8(c), the suspension sucked up into the pipette chip 10 is held in the holding portion 10c of the pipette chip 10. The magnetic particle 14 for pretreatment suspended in the suspension is remotely fixed to a certain region on the inner wall surface of the holding portion 10c by a magnetic field of the magnet M at the outside of the pipette chip 10.

After the suspension is held in the pipette chip 10, the remaining solution is discharged into the well 12 with the magnetic particle 14 for pretreatment being fixed to one position by the magnetic field of the magnet M. In this way, the magnetic particle 14 for pretreatment to which the nonspecific reaction factor 15 is bound is removed from the specimen, thereby obtaining an assay sample in which the contaminant is removed from the specimen. Thus, by utilizing the magnetic particle 14 to which the antibody against the nonspecific reaction factor 15 is immobilized for removal of the nonspecific reaction factor, the frequency that the magnetic particle to which the antibody against the nonspecific reaction factor is immobilized encounters the nonspecific reaction factor can be increased, and it is possible to efficiently trap and remove the nonspecific reaction factor.

Figure 10:
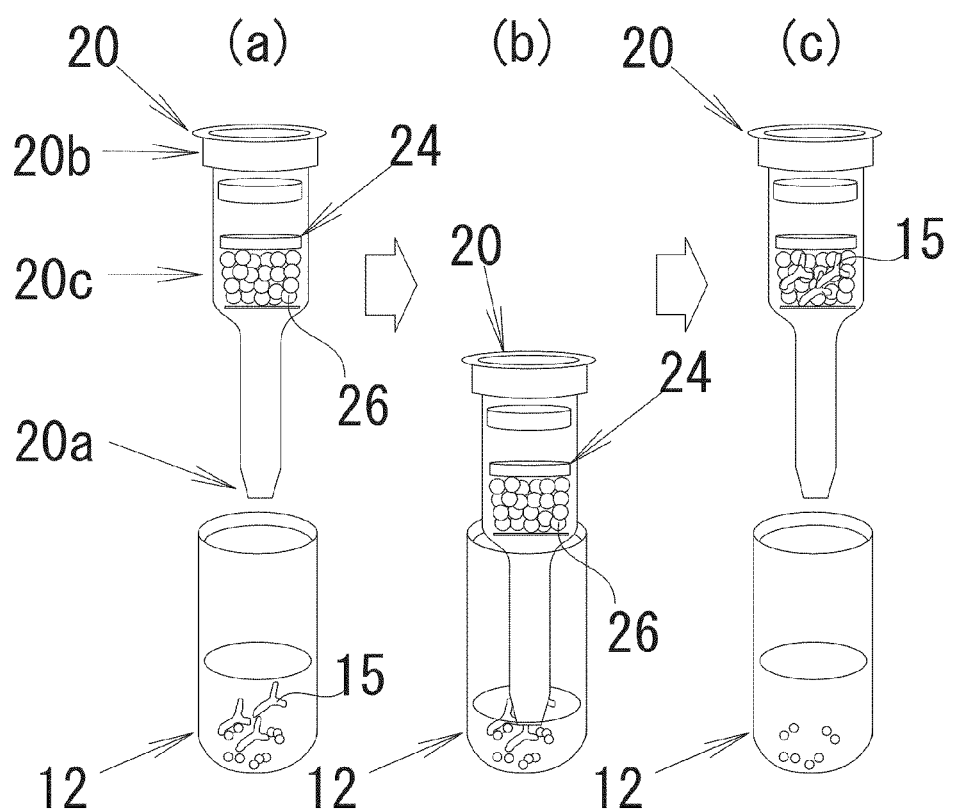
FIG. 10 is an explanatory drawing for explaining a treatment of removing a contaminant using a column to which an antibody against a nonspecific reaction factor is immobilized.
Figure 11:
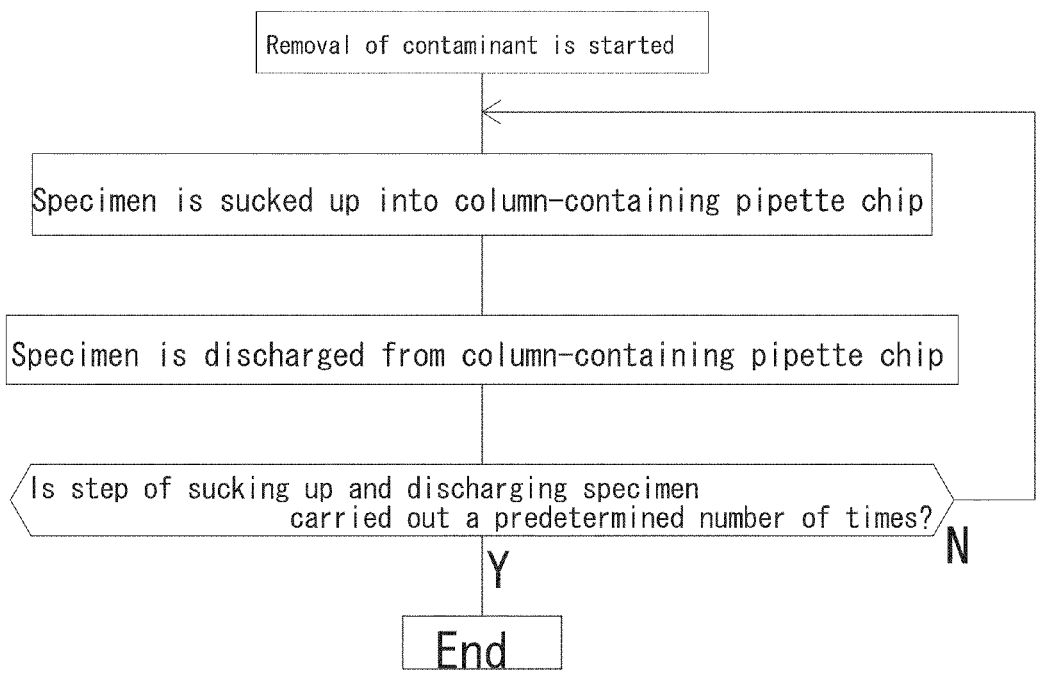
FIG. 11 is a flow chart of a treatment of removing a contaminant using a column to which an antibody against a nonspecific reaction factor is immobilized.

3-2. Treatment of Removing Contaminant Using Affinity Column to which Antibody Against Nonspecific Reaction Factor is Immobilized FIG. 10 shows a treatment of removing a contaminant using a column to which an antibody against a nonspecific reaction factor is immobilized. FIG. 11 is a flow chart of a treatment of removing a contaminant using a column to which an antibody against a nonspecific reaction factor is immobilized. As shown in FIGS. 10 and 11, a column-containing pipette chip 20 has a column 24 for removing a nonspecific reaction factor. As shown in FIG. 10(a), the outer shape, size and material of the column-containing pipette chip 20 are the same as those of the above-described pipette chip 10. The column 24 contains many affinity resins 26 having a pellet-like shape, and to each affinity resin 26, an antibody for trapping the nonspecific reaction factor is bound. As shown in FIG. 10(b), when the specimen held in the well 12 is passed through the column 24, the nonspecific reaction factor in the specimen is bound to the above-described antibody and trapped by the column 24. A step of sucking up the specimen into the column-containing pipette chip 20 and then discharging the specimen from the column-containing pipette chip 20 is repeated a predetermined number of times, thereby trapping more nonspecific reaction factors with the column 24. As shown in FIG. 10(c), by performing discharge into the well 12 after the step of sucking up and discharging the specimen is carried out a predetermined number of times, it is possible to provide an assay sample in which the nonspecific reaction factor has been removed from the specimen.

Figure 12:
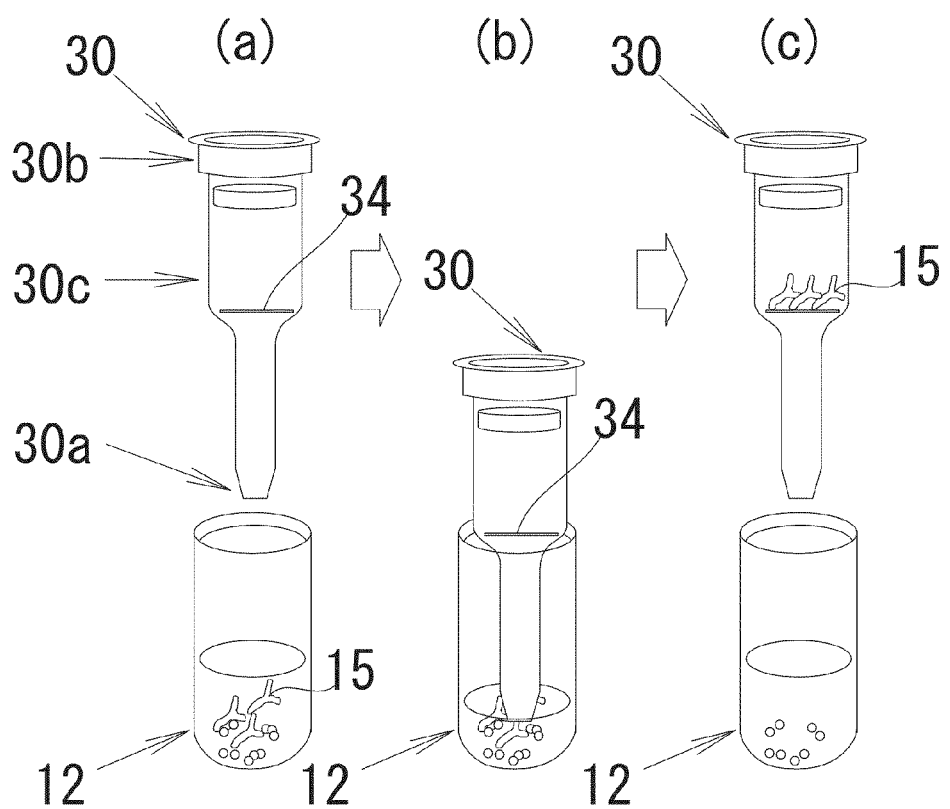
FIG. 12 is an explanatory drawing for explaining a treatment of removing a contaminant using a membrane to which an antibody against a nonspecific reaction factor is immobilized.
Figure 13:
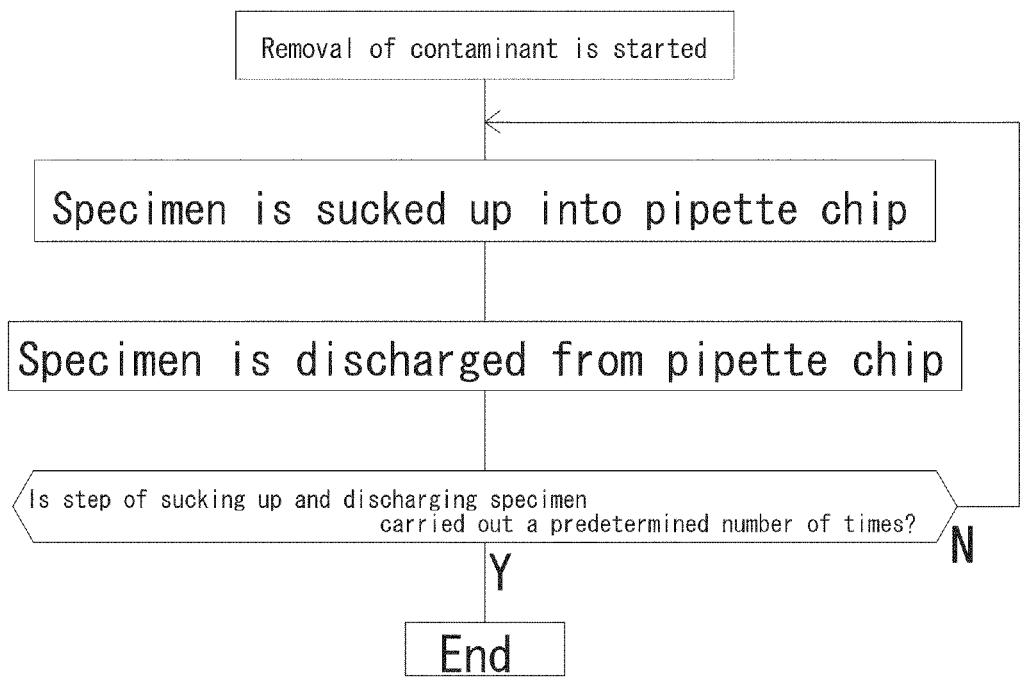
FIG. 13 is a flow chart of a treatment of removing a contaminant using a membrane to which an antibody against a nonspecific reaction factor is immobilized.

3-3. Treatment of Removing Contaminant Using Filtering Material Such as Membrane to which Antibody Against Nonspecific Reaction Factor is Immobilized FIG. 12 shows a treatment of removing a contaminant using a membrane to which an antibody against a nonspecific reaction factor is immobilized. FIG. 13 is a flow chart of a treatment of removing a contaminant using a membrane to which an antibody against a nonspecific reaction factor is immobilized. As shown in FIGS. 12 and 13, a membrane-containing pipette chip 30 has a membrane 34 for removing a nonspecific reaction factor. As shown in FIG. 12(a), the outer shape, size and material of the membrane-containing pipette chip 30 are the same as those of the above-described pipette chip 10. The membrane 34 is formed into a sheet-like shape, and an antibody against the nonspecific reaction factor is immobilized to the membrane 34. As shown in FIG. 12(b), when the specimen is passed through the membrane 34, the nonspecific reaction factor in the specimen is bound to the above-described antibody and trapped by the membrane 34. A step of sucking up the specimen in the well 12 into the membrane-containing pipette chip 30 and then discharging the specimen from the membrane-containing pipette chip 30 is repeated a predetermined number of times, thereby trapping more nonspecific reaction factors with the membrane 34. As shown in FIG. 12(c), by performing discharge into the well 12 after the step of sucking up and discharging the specimen is carried out a predetermined number of times, it is possible to provide an assay sample in which the nonspecific reaction factor has been removed from the specimen.

Figure 14:
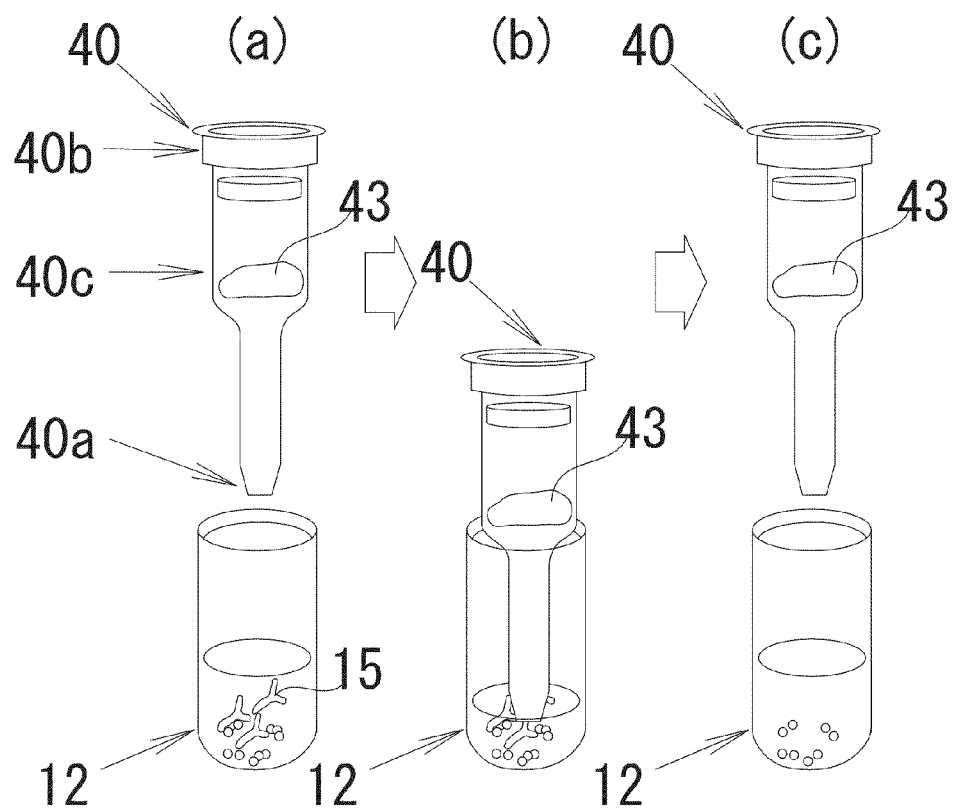
FIG. 14 is an explanatory drawing for explaining a treatment of removing a contaminant using a gel to which a reducing agent is immobilized.
Figure 15:
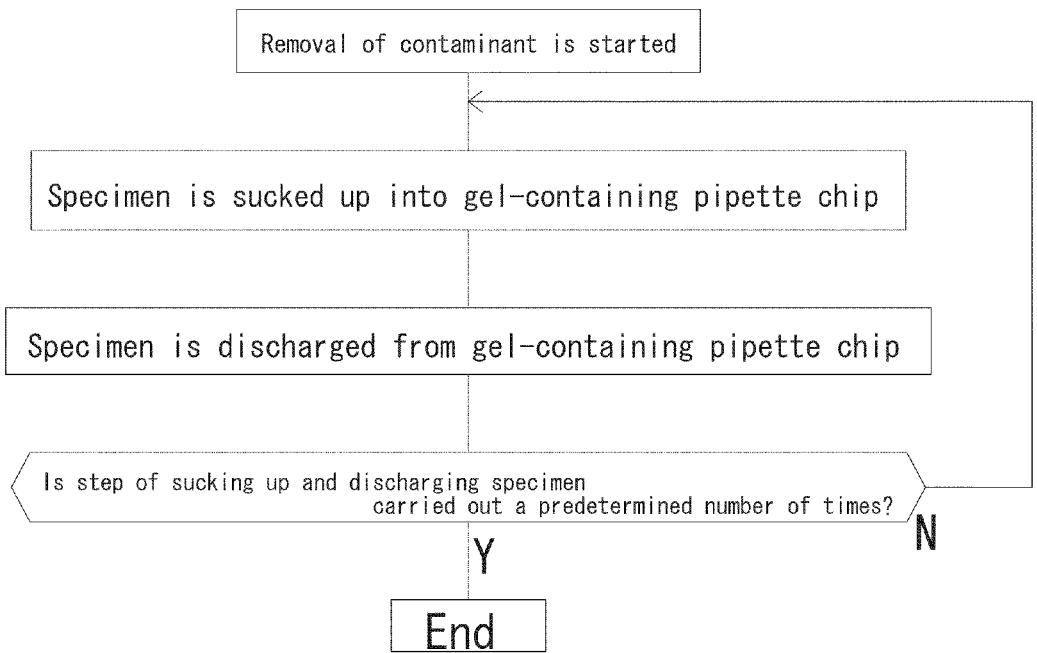
FIG. 15 is a flow chart of a treatment of removing a contaminant using a gel to which a reducing agent is immobilized.

3-4. Treatment of Removing Contaminant Using Gel to which Reducing Agent is Immobilized FIG. 14 shows a treatment of removing a contaminant using a gel to which a reducing agent is immobilized. FIG. 15 is a flow chart of a treatment of removing a contaminant using a gel to which a reducing agent is immobilized. As shown in FIGS. 14 and 15, a gel-containing pipette chip 40 has a gel 43 for decomposing a nonspecific reaction factor. As shown in FIG. 14(a), the outer shape, size and material of the gel-containing pipette chip 40 are the same as those of the above-described pipette chip 10. To this gel 43, a reducing agent for decomposing a nonspecific reaction factor (substance that inactivates a contaminant) is immobilized. As the reducing agent, for example, Tris(2-carboxylethyl)phosphine (TCEP), glutathione or the like can be used. As shown in FIG. 14(b), when the specimen is passed through the gel to which the reducing agent is immobilized, the nonspecific reaction factor in the specimen is decomposed by the reducing agent. A step of sucking up the specimen in the well 12 into the gel-containing pipette chip 40 and then discharging the specimen from the gel-containing pipette chip 40 is repeated a predetermined number of times, thereby decomposing more non-specific reaction factors with the reducing agent. As shown in FIG. 14(c), by performing discharge into the well 12 after the step of sucking up and discharging the specimen is carried out a predetermined number of times, it is possible to provide the specimen from which the nonspecific reaction factor has been removed. The explanation above is about an example in which the nonspecific reaction factor is decomposed by the reducing agent held by the gel, but an antibody against the nonspecific reaction factor may be held by the gel. In this case, using the gel to which the antibody against the nonspecific reaction factor is immobilized, the nonspecific reaction factor can be trapped and removed.

3-5. Other Cases (Treatment Using Plastic Member)

In addition to the above-described embodiments, for example, it is also possible to pretreat the specimen using a product in which the antibody against the nonspecific reaction factor is immobilized to a plastic support. For example, a plurality of concave holes are arranged on a support in a matrix fashion, and the antibody against the nonspecific reaction factor is immobilized in the concave holes in advance. When the nonspecific reaction factor in the specimen is held in the concave holes, the nonspecific reaction factor in the specimen is bound to the antibody against it and immobilized. By immersing the tip portion of the pipette chip in the concave holes to suck up a liquid, it is possible to prepare an assay sample in which the nonspecific reaction factor has been removed from the specimen.

Figure 16:
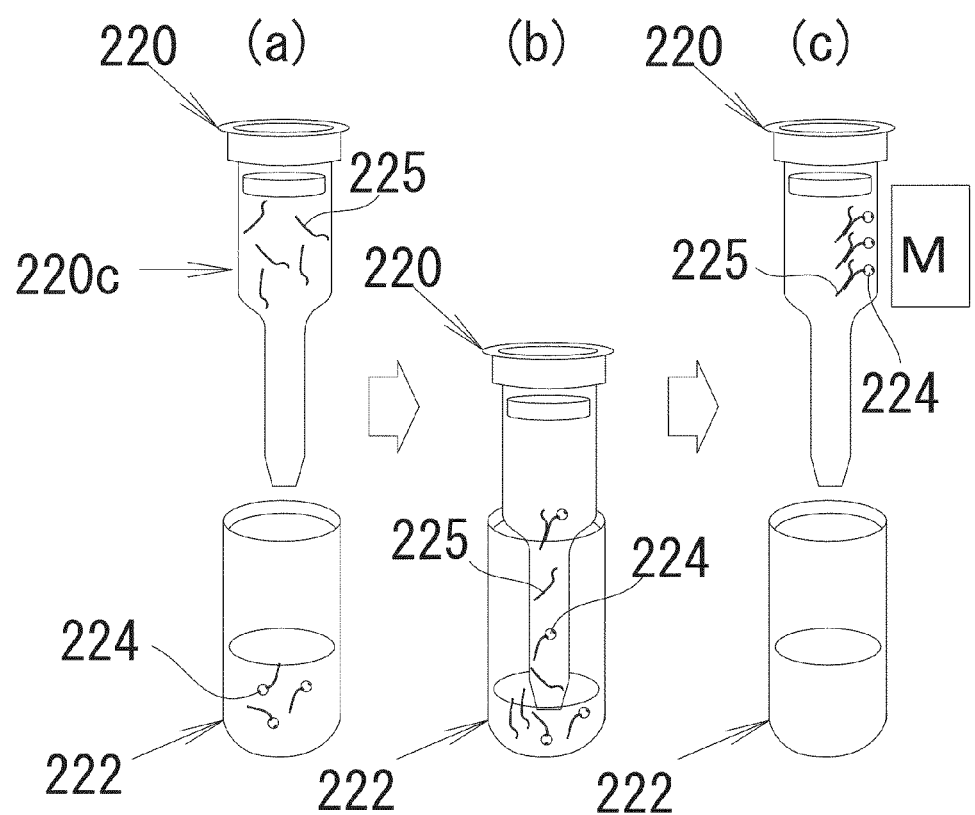
FIG. 16 is an explanatory drawing for explaining an extraction treatment using magnetic particles to which a probe having affinity to nucleic acid is immobilized.
Figure 17:
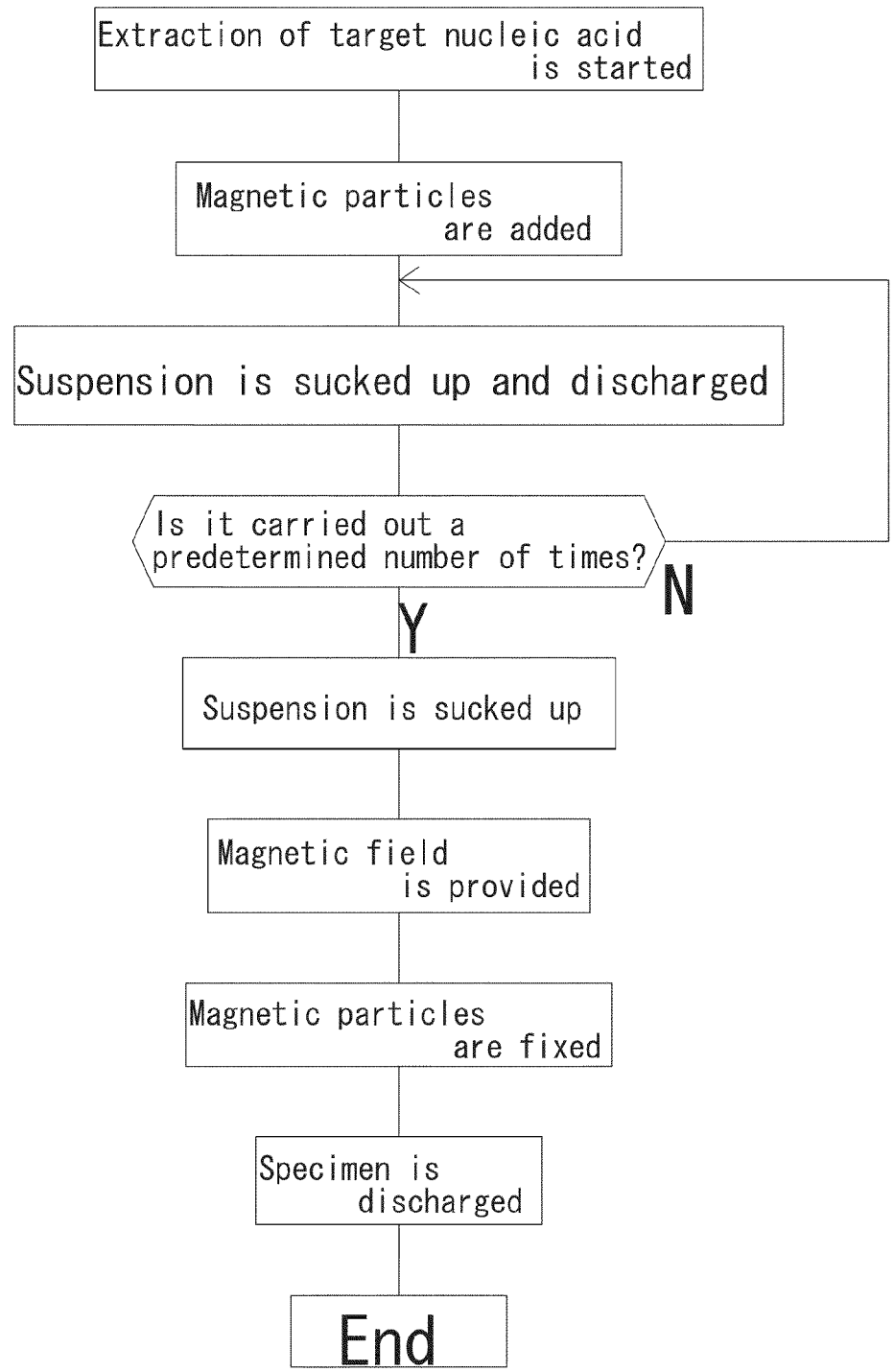
FIG. 17 is a flow chart of a treatment of extracting a nucleic acid using magnetic particles to which a probe having affinity to the nucleic acid is immobilized.

3-6. Treatment of Extracting Target Nucleic Acid Using Magnetic Particles to which Probe for Trapping Nucleic Acid is Immobilized FIG. 16 is an explanatory drawing for schematically explaining a treatment of extracting a target nucleic acid using magnetic particles (first support) to which a probe for trapping the nucleic acid is immobilized. FIG. 17 is a flow chart of a treatment of extracting a target nucleic acid using magnetic particles to which a probe for trapping the nucleic acid is immobilized. As shown in FIG. 16, when the assay system pretreats a specimen using a well and a pipette chip, firstly, a predetermined amount of the specimen held in a well is sucked up into a pipette chip 220. Next, the pipette chip 220 into which the specimen is sucked up is moved to a well 222 in which a solution of magnetic particles for pretreatment is held, and the specimen in the pipette chip 220 is discharged into the well 222 in which the solution of magnetic particles for pretreatment is held. Using the pipette chip 220, the specimen and the solution of magnetic particles for pretreatment are mixed homogeneously by sucking up and discharging, thereby producing a suspension. It is allowed to stand for a predetermined time after stirring is completed, and a target nucleic acid 225 in the specimen is allowed to be bound to a probe to which a magnetic particle 224 for pretreatment is immobilized.

As shown in FIG. 16(c), after the suspension is allowed to stand for a predetermined time, the suspension is sucked up into the pipette chip 220 and held in a holding portion 220c. The magnetic particle 224 for pretreatment contained in the suspension is remotely fixed to a certain region on the inner wall surface of the holding portion 220c by a magnetic field of a magnet M at the outside of the pipette chip 220. After the suspension is held in the pipette chip 220, the remaining solution is discharged into the well 222 with the magnetic particle 224 for pretreatment being fixed to one position by the magnetic field of the magnet M. The magnetic particle 224 to which a target nucleic acid 225 is bound is taken out from the specimen, thereby extracting the target nucleic acid from the specimen. Thus, by using magnetic particles to which a probe which can bind to a target nucleic acid is immobilized for extraction of the target nucleic acid, the target nucleic acid can be trapped and extracted efficiently.

On a well plate, for example, a plurality of wells 12 are arranged in a line or in a matrix fashion. The specimen is held in a specific well 12 in advance, and in another well, a solution containing a required amount of magnetic particles (hereinafter referred to as "magnetic particles for pretreatment") to which an antibody against a nonspecific reaction factor (hereinafter referred to as "antibody for pretreatment") is immobilized (hereinafter referred to as "solution of magnetic particles for pretreatment" is held in advance.

Figure 18:
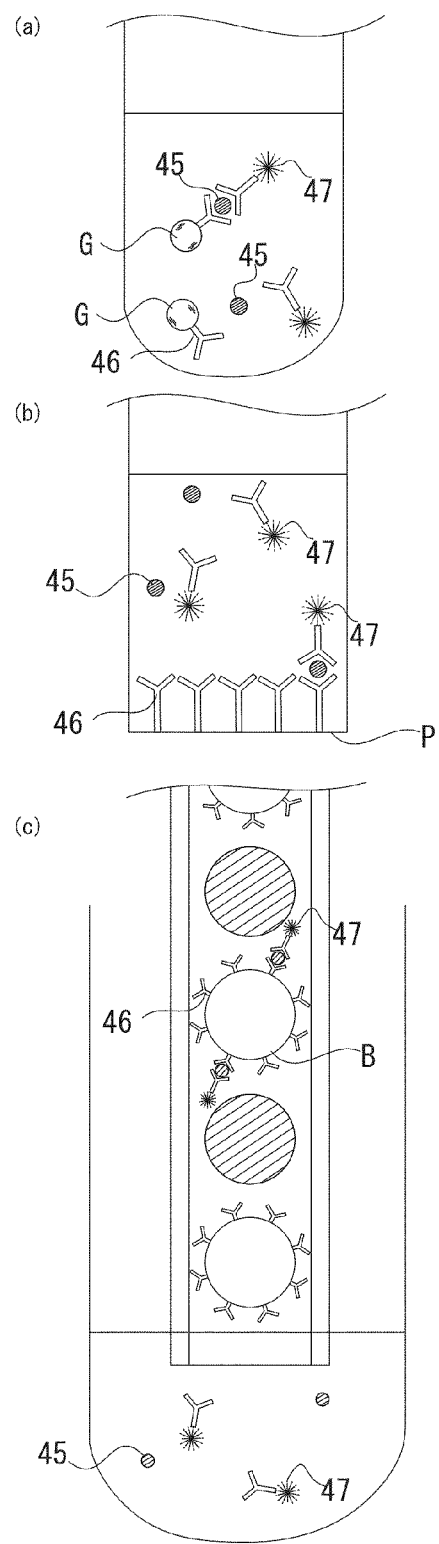
FIG. 18 is an explanatory drawing for schematically explaining a magnetic particle to which an antibody against an antigen is immobilized, a plate to which the antibody against the antigen is immobilized, and a bead to which the antibody against the antigen is immobilized.

In the present invention, before moving to a step of detecting an assay sample, a step of preparing a second support to which a substance having affinity to a biologically-relevant substance is immobilized is carried out. FIG. 18 is an explanatory drawing for schematically explaining a magnetic particle to which an antibody against an antigen is immobilized, a plate to which the antibody against the antigen is immobilized, and a bead to which the antibody against the antigen is immobilized. As the second support to be prepared before moving to a detection step, for example, as shown in FIG. 18, (a) a magnetic particle G to which an antibody 46 against an antigen 45 is immobilized, (b) a plate P to which the antibody 46 against the antigen 45 is immobilized, and (c) a bead B to which the antibody 46 against the antigen 45 is immobilized are exemplified. As shown in FIG. 18(a), a second support can be prepared by immobilizing the antibody 46 against the antigen 45 to the magnetic particle G. Further, as shown in FIG. 18(b), a second support of another embodiment can be prepared by immobilizing the antibody 46 against the antigen 45 to the plate P. Moreover, as shown in FIG. 18(c), a second support of yet another embodiment can be prepared by immobilizing the antibody 46 against the antigen 45 to the bead B. By preparing the second support in advance in this way, it is possible to smoothly carry out a next assay step, and improvement of assay accuracy, etc. can be expected. To the prepared second antibody, the antigen 45 can be specifically bound, and in addition, to the antigen 45, a labeling substance 47 that causes a fluorescence reaction or luminescence reaction can be specifically bound via another antibody against the antigen (secondary antibody).

4. Assay of Biologically-Relevant Substance

The step of assaying a biologically-relevant substance includes a step of labeling the biologically-relevant substance and a step of detecting the labeled biologically-relevant substance. Hereinafter, each step will be described.

4-1. Labeling Reaction Step

Figure 19:
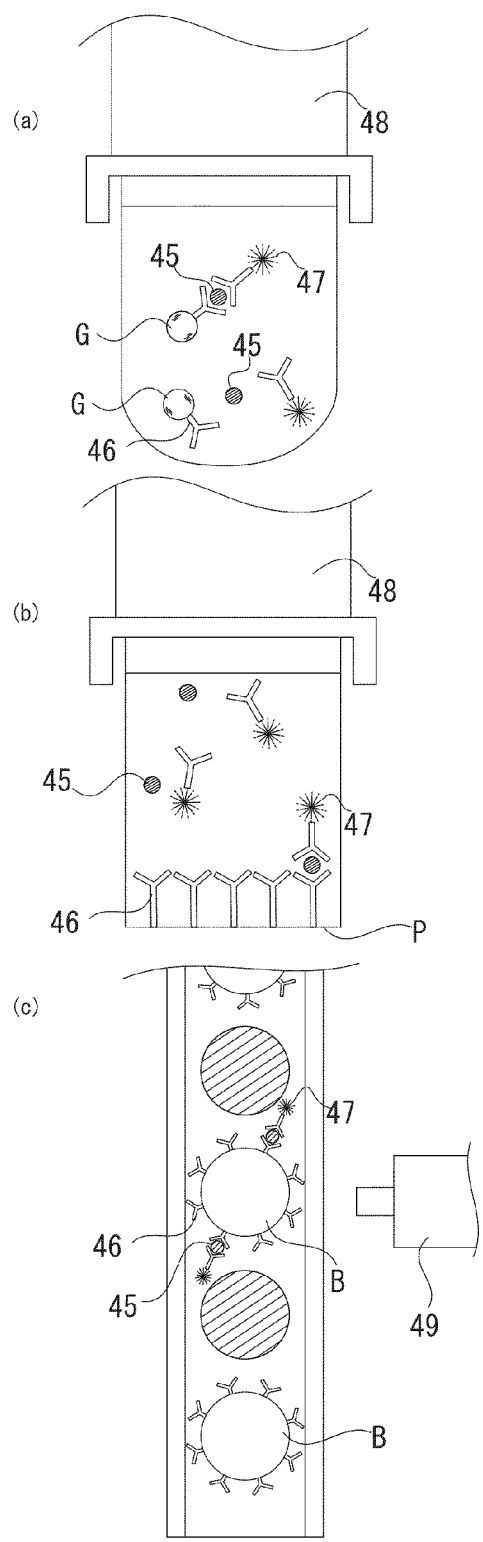
FIG. 19 is an explanatory drawing for schematically explaining an embodiment in which an antigen is detected by trapping and labeling the antigen using a second support.

A labeling reaction step is included in the step of assaying a target biologically-relevant substance and is carried out using the second antibody. FIG. 19 is an explanatory drawing for schematically explaining an embodiment in which an antigen is detected by trapping and labeling the antigen using a second support. As shown in FIG. 19, in the labeling reaction step, a biologically-relevant substance is trapped from an assay sample in which treatments such as removal of a contaminant from a specimen have been performed and the biologically-relevant substance is labeled. For example, when an antigen is to be trapped as the biologically-relevant substance, for labeling the antigen, the antibody 46 that binds to the antigen 45 is used. After the labeling substance 47 is bound to the antigen 45, a detection step described hereinbelow is carried out. As shown in FIGS. 19 (a) and (b), in the case where the magnetic particle G to which the antibody 46 against the antigen 45 is immobilized is used as the second support, and in the case where the plate P to which the antibody 46 against the antigen 45 is immobilized is used as the second support, for example, the labeled antigen can be detected using a photomultiplier tube (PMT) 48. Further, as shown in FIG. 19 (c), in the case where the bead B to which the antibody 46 against the antigen 45 is immobilized is used as the second support, for example, the antigen can be detected using a photon counter utilizing optical fiber. Hereinafter, two typical embodiments in which an antigen is trapped from a specimen and a labeling antibody is provided thereto will be described more specifically.

4-1-1. Labeling of Antigen Using Magnetic Particles to which Antibody Against Antigen is Immobilized Here, an embodiment in which a single antigen is trapped and labeled using magnetic particles to which an antibody against the antigen is immobilized as the second support will be described. After the treatment of highly purifying the specimen, the assay system carries out an immunoassay having the assay step comprising the labeling reaction step. In a first well (first holding portion) on a well plate, a solution containing a required amount of magnetic particles (hereinafter referred to as "magnetic particles for specific reaction") to which an antibody against an antigen targeted for detection (hereinafter referred to as "antibody for specific reaction") is immobilized (hereinafter referred to as "solution of magnetic particles for specific reaction") is held in advance, and in addition, in a second well (second holding portion), a solution containing a labeling antibody against the antigen (hereinafter referred to as "labeling antibody") (hereinafter referred to as "labeling solution") is held in advance. In addition, in a third well, a substrate solution is held.

Figure 20:
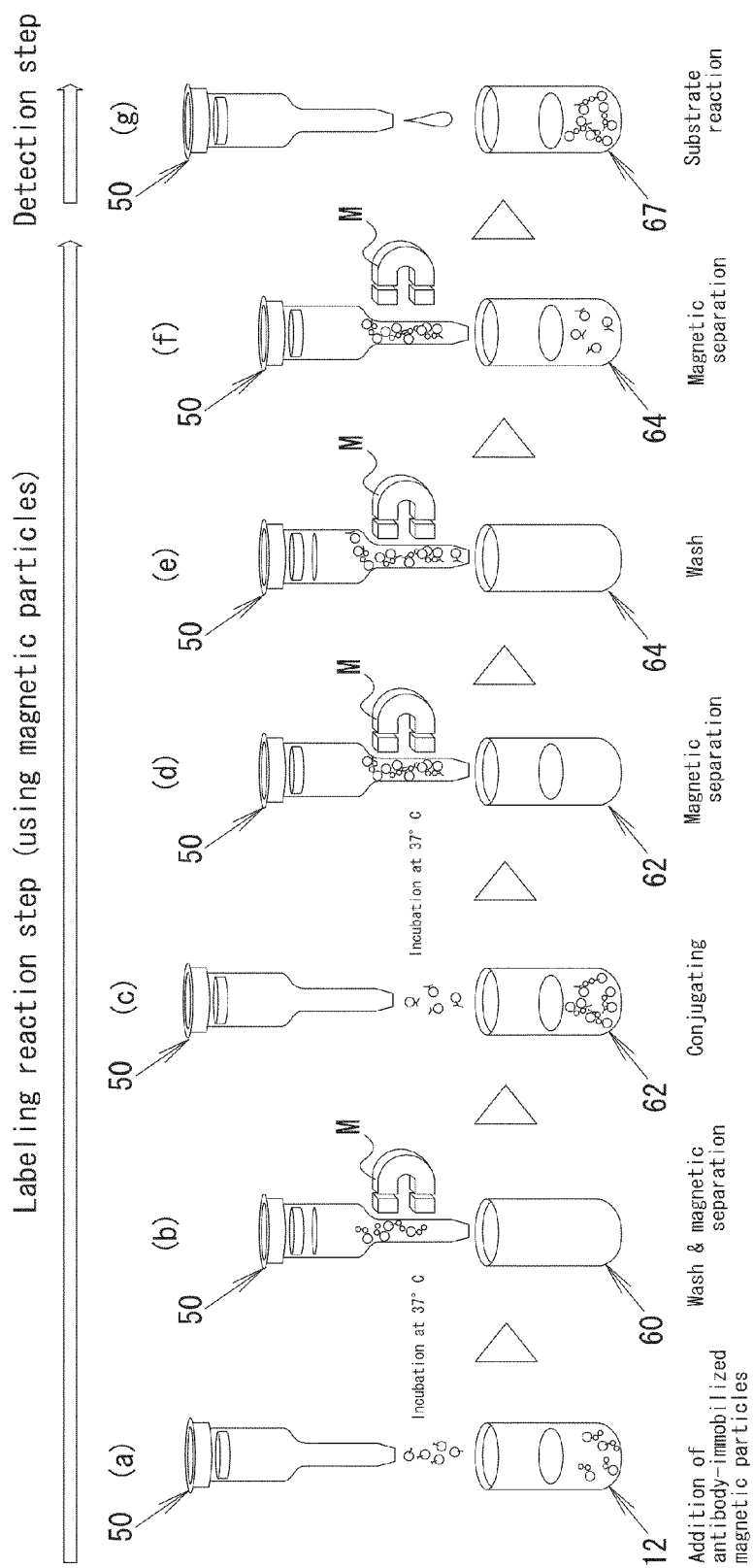
FIG. 20 is an explanatory drawing for explaining an immunoassay using magnetic particles.

FIG. 20 shows an immunoassay using magnetic particles. As shown in FIG. 20, another pipette chip 50, which is the same type of the pipette chip used in the pretreatment such as removal of the contaminant, is newly attached to the nozzle, and the solution of magnetic particles for specific reaction held in another well is sucked up into the pipette chip 50. As shown in FIG. 20(a), the pipette chip 50 holding the solution of magnetic particles for specific reaction inside is controlled to be moved to a well 12 in which an assay sample is held, and the tip portion is immersed in the well 12. The magnet M is gradually moved away from the pipette chip 50 to release the magnetic particles for specific reaction from constraining by the magnetic field, and the solution of magnetic particles for specific reaction is mixed with the assay sample. A mixture of the solution of magnetic particles for specific reaction and the assay sample is sucked up and discharged, thereby forming a suspension in which the magnetic particles for specific reaction are homogeneously suspended. As shown in FIG. 20(a)

and FIG. 20(b), after the suspension is formed, for example, it is allowed to stand (incubated) at 37° C. for a certain period of time, and the antigen in the suspension is specifically reacted with and bound to the antibody for specific reaction immobilized to the magnetic particles for specific reaction. In the explanation above, the solution of magnetic particles for specific reaction is sucked up into the pipette chip 50 and added to the specimen holding portion (well) 12 in which the assay sample is held, but it is also possible to suck up the assay sample into the pipette chip 50 and add the assay sample to a well in which the solution of magnetic particles for specific reaction is held.

As shown in FIG. 20(b), after the suspension is allowed to stand, the suspension is held in the pipette chip 50. After the suspension is held in the pipette chip 50, the magnet M is moved toward the outer circumference of the holding portion of the pipette chip 50, and the magnetic particles for specific reaction to which the antigen is bound (hereinafter referred to as "antigen-bound magnetic particles") are gathered at one position in the holding portion of the pipette chip 50. After the antigen-bound magnetic particles are collected, the remaining solution is discharged into the well 12, and only the antigen-bound magnetic particles are held in the pipette chip 50.

As shown in FIG. 20(b), the pipette chip 50 holding the antigen-bound magnetic particles is controlled to be moved to a well 60 holding a washing solution with the antigen-bound magnetic particles being maintained to be held. The tip portion of the pipette chip 50 is immersed in the washing solution in the well 60, and after that, the magnet M is gradually moved away from the outer circumference of the holding portion of the pipette chip 50, and the antigen-bound magnetic particles in the pipette chip 50 are mixed with the washing solution. The washing solution with which the antigen-bound magnetic particles are mixed is subjected to flow stirring by sucking up and discharging by the pipette chip 50. After stirring, the washing solution with which the antigen-bound magnetic particles are mixed is sucked up into the pipette chip 50. The magnet M is moved toward the outer circumference of the holding portion of the pipette chip 50, and the antigen-bound magnetic particles are gathered at one position. After the antigen-bound magnetic particles are constrained at one position, the remaining solution is discharged into the well 60.

As shown in FIG. 20(c), after the solution is discharged, the pipette chip 50 with the antigen-bound magnetic particles being held is controlled to be moved to a well 62 holding a labeling solution containing a labeling antibody (enzyme-labeling antibody) against an antigen. The tip portion of the pipette chip 50 is immersed in the labeling solution, and then the magnet M is gradually moved away from the outer circumference of the holding portion of pipette chip 50 to release the antigen-bound magnetic particles from constraining. By sucking up and discharging the labeling solution with which the antigen-bound magnetic particles are mixed, the antigen-bound magnetic particles can be mixed with and homogeneously suspended in the labeling solution. After suspending, for example, the obtained suspension is allowed to stand at 37° C. for a certain period of time, thereby allowing the enzyme-labeling antibody to bind to the antigen.

As shown in FIG. 20(d), after the suspension is allowed to stand (incubated) for a certain period of time, the suspension in the well 62 is slowly sucked up into the pipette chip 50. After the suspension is held in the pipette chip 50, the magnet M is moved toward the pipette chip 50, and the magnetic particles suspended in the suspension held are constrained at one position. After constraining the magnetic particles to which the enzyme-labeling antibody is bound (hereinafter referred to as "labeling antibody-bound magnetic particles"), the solution from which the labeling antibody-bound magnetic particles are removed is discharged into the well 62, and only the labeling antibody-bound magnetic particles remain in the pipette chip 50.

After that, as shown in FIG. 20(e), the pipette chip 50 with the labeling antibody-bound magnetic particles being held is controlled to be moved to a well 64 holding a washing solution. The magnet M is gradually moved away from the pipette chip 50, and the washing solution in the well 64 is mixed with the labeling antibody-bound magnetic particles (see FIG. 20(f)). The labeling antibody-bound magnetic particles are washed in a manner similar to that of the already-described washing step, and after that, the pipette chip 50 holding the labeling antibody-bound magnetic particles is controlled to be moved to a well 67 holding a substrate solution, and a detection step described hereinbelow (see FIG. 20(g)) is started.

In the explanation above, the magnetic particles to which the antibody against the antigen is immobilized are mixed with the specimen after the treatment such as removal of the contaminant to allow the antibody to bind to the antigen, and after that, using the labeling solution, the enzyme-labeling antibody is bound to the antigen. However, the order of labeling is not limited thereto. For example, it is possible to use magnetic particles to which the enzyme-labeling antibody and the antibody are immobilized in advance.

Figure 21:
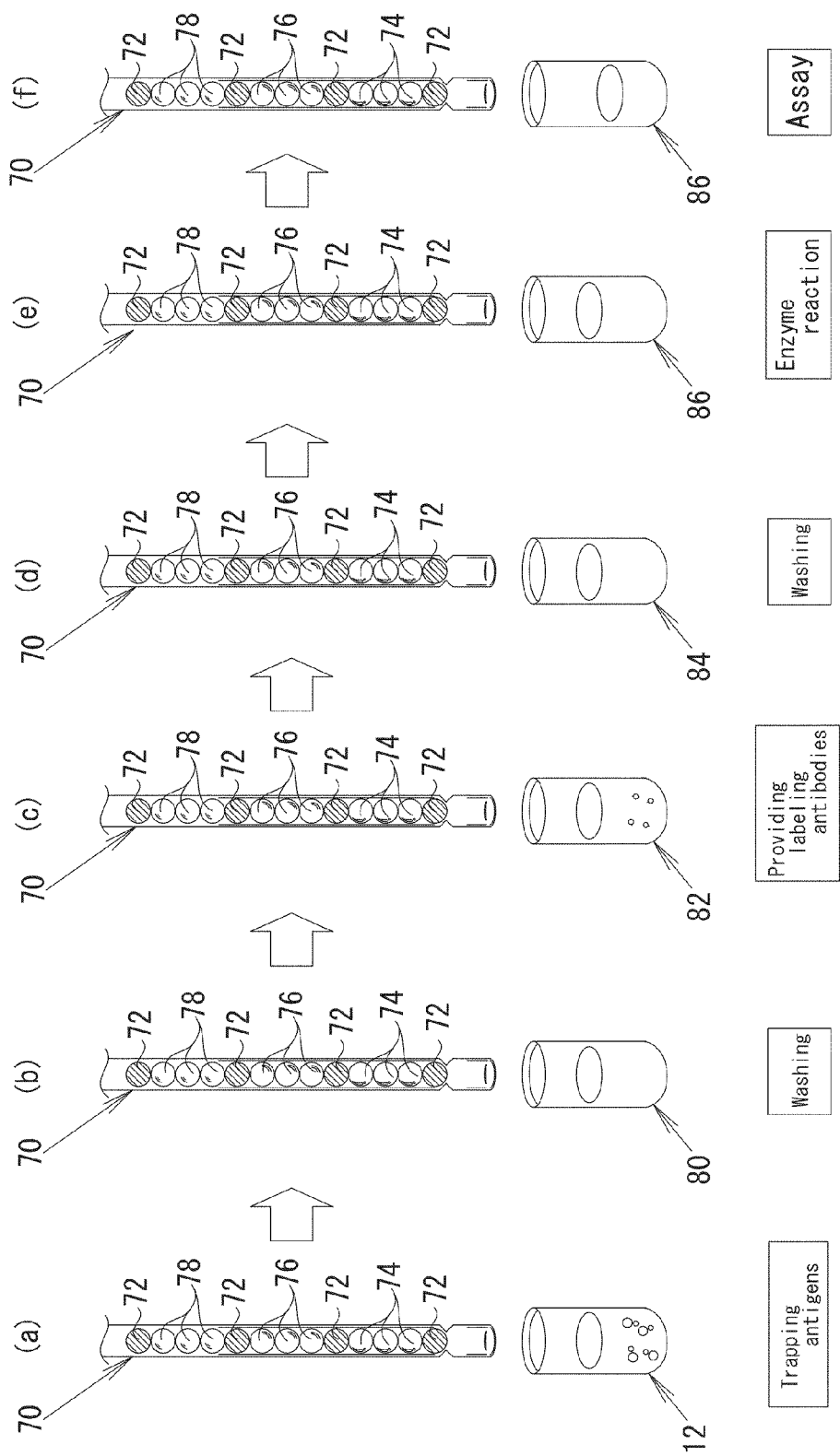
FIG. 21 is an explanatory drawing for explaining an immunoassay using an antigen separation/immobilization tube.

4-1-2. Simultaneous Labeling Reaction Step of a Plurality of Types of Antigens Using a Plurality of Antibody-Immobilized Beads In item [4-1-1] above, a single antigen is trapped and labeled, but in this item, an embodiment in which a plurality of types of antigens are trapped and labeled at a time will be described. FIG. 21 shows an immunoassay using an antigen separation/immobilization tube. As shown in FIG. 21, a transparent antigen separation/immobilization tube 70 formed into a tubular shape holds beads as the second support to which an antibody against an antigen is immobilized in advance (hereinafter referred to as "antibody-immobilized beads") and spacer beads 72 which are positioned so that a certain number of antibody-immobilized beads are separated, and these beads are arranged in a line along the tube. Regarding the antibody-immobilized beads, for example, 3 first antibody-immobilized beads 74 to which a first antibody is immobilized, 3 second antibody-immobilized beads 76 to which a second antibody is immobilized, and 3 third antibody-immobilized beads 78 to which a third antibody is immobilized are respectively positioned continuously, and between the continuously-positioned antibody-immobilized beads 74, 76 and 78, each spacer bead 72 is positioned. The arrangement of the beads may be suitably changed, and in some cases, the spacer beads can be omitted.

To the upper end portion of the antigen separation/immobilization tube 70, a mounting portion (not shown) to be mounted on the nozzle of the assay system is provided, and the lower end is opened so that a liquid can be sucked up and discharged. A pump mechanism is provided to the assay system of the present invention so that a liquid can be sucked up into or discharged from the antigen separation/immobilization tube 70 mounted on the nozzle.

As shown in FIG. 21(a), when the lower end of the antigen separation/immobilization tube 70 is immersed in a well 12 and an assay sample in the well 12, which has been subjected to treatments such as removal of a contaminant, is sucked up into the antigen separation/immobilization tube 70, first to third antigens, which respectively correspond to the first to third antibodies, bind to the antibodies and are trapped by the beads 74, 76 and 78 to which the first to third antibodies are immobilized respectively. By repeating sucking up and discharging of the specimen a predetermined number of times, the antigens are certainly bound to the antibody-immobilized beads 74, 76 and 78.

As shown in FIG. 21(*b*), after repeating sucking up and discharging of the specimen a predetermined number of times, a washing solution in another well 80 is sucked up and the first to third antibodies-immobilized beads 74, 76 and 78 are washed. As shown in FIG. 21(*c*), after washing the first to third antibodies-immobilized beads 74, 76 and 78, the lower end of the antigen separation/immobilization tube 70 is immersed in an enzyme-labeling solution held in another well 84, and the enzyme-labeling solution is sucked up into the antigen separation/immobilization tube 70. In the enzyme-labeling solution, 3 types of enzyme-labeling antibodies, which correspond to the respective antigens that bind to the first to third antibodies, are mixed. When the enzyme-labeling solution is sucked up into the antigen separation/immobilization tube 70, the enzyme-labeling antibodies bind to the respective antigens. As shown in FIG. 21(*d*), after carrying out sucking up and discharging of the enzyme-labeling solution a predetermined number of times, a washing solution held in another well 84 is sucked up and discharged, thereby washing the first to third antibodies-immobilized beads 74, 76 and 78 to which the antigens and the enzyme-labeling antibodies are bound. As shown in FIG. 21(*e*), after washing, the antigen separation/immobilization tube is controlled to be moved to a well 86 holding a substrate solution, and a detection step described hereinbelow is started. In the explanation above, the mixture of the 3 types of the enzyme-labeling antibodies is used, but alternatively, enzyme labeling can be performed by using 3 wells, in which different types of enzyme-labeling antibodies are held respectively, and performing a step consisting of sucking up and discharging of an enzyme-labeling antibody and washing with respect to these 3 wells sequentially.

Thus, by treating the specimen using the antigen separation/immobilization tube 70 in which the beads 74, 76 and 78 to which the different types of antibodies are respectively immobilized are arranged, a plurality of antigens can be trapped at a time, and many items can be detected simultaneously. In addition, it is possible to reduce the time to detect the antigen in the specimen.

In the explanation above, the beads 74, 76 and 78 to which the antibodies against the antigens are immobilized are contacted with the specimen that has been subjected to treatments such as removal of a contaminant to allow the antibodies to bind to the antigens, and then the enzyme-labeling antibodies are bound to the antigens using the labeling solution. However, the order of labeling is not limited thereto. For example, it is possible to perform a step of trapping antigens using beads to which enzyme-labeling antibodies are immobilized in advance.

4-2. Detection Step

The antigens to which the enzyme-labeling antibodies are bound are mixed with the substrate solution to develop the color of the substrate, and detection of absorbance, etc. is carried out. Hereinafter, a detection step in the case where antigens are labeled using the above-described magnetic particles and a detection step in the case where antigens are labeled using the antigen separation/immobilization tube will be described separately.

4-2-1. Detection Utilizing Magnetic Particles and Pipette Chip

The assay system of the present invention has, for example, a light irradiation portion which irradiates the side of a well with a light flux having a specific wavelength, a light receiving portion which receives the light flux irradiated from the light irradiation portion via the well, a signal processing circuit which processes a signal outputted from the light receiving portion to form, for example, absorbance data or emission intensity data, etc.

As shown in FIG. 20(*g*), the pipette chip 50 holding the labeling antibody-bound magnetic particles is controlled to be moved to the well 67 holding the substrate solution. After the tip portion of the pipette chip 50 is immersed in the substrate solution in the well 67, the magnet M is moved away from the outer circumference of the holding portion of the pipette chip 50 to release the labeling antibody-bound magnetic particles from constraining, and the labeling antibody-bound magnetic particles are mixed with the substrate solution. After the labeling antibody-bound magnetic particles are mixed with the substrate solution, sucking up the mixture into the pipette chip 50 and discharging the mixture into the well 67 are carried out a predetermined number of times, thereby forming a suspension in which the labeling antibody-bound magnetic particles are dispersed homogeneously. In this way, the labeling antibody-bound magnetic particles can be homogeneously reacted with the substrate solution.

The labeling antibody-bound magnetic particles are reacted with the substrate solution to develop the color of the substrate, and after that, for example, the side of the well 67 is irradiated with a light flux having a specific wavelength, and absorbance thereof is detected. Note that in the case of a test method in which a luminescent state is maintained for a very short time, such as CLIA, the following method may be employed: a liquid-holding portion is provided; a filter and a water-absorbing pad are provided to the liquid-holding portion; the magnetic particles are discharged together with the washing solution sucked up in the previous step from the pipette chip into the liquid-holding portion and the magnetic particles are collected by the filter; after that, a luminescence-inducing solution such as hydrogen peroxide solution ($H_2O_2$) is supplied from the nozzle to allow the magnetic particles to become luminescent; and luminescence at the time of dispensing is measured using an optical measuring device such as PMT.

4-2-2. Detection Utilizing Antigen Separation/Immobilization Tube

As shown in FIG. 21(*e*), when a plurality of antigens are trapped using the antigen separation/immobilization tube 70 as the second support, the plurality of the antigens can be detected at a time. The assay system of the present invention has a plurality of light irradiation portions which irradiate with a light flux having a specific wavelength, a plurality of light receiving portions which receive the light flux irradiated from each of the light irradiation portions via the antigen separation/immobilization tube 70, a signal processing circuit which forms emission intensity data by, for example, amplifying and digitizing output signals from the light receiving portions, etc. Firstly, the lower end of the antigen separation/immobilization tube 70 is immersed in the well 86 holding the substrate solution, and the substrate solution is sucked up into the antigen separation/immobilization tube 70. Sucking up and discharging the substrate solution is carried out a predetermined number of times to sufficiently perform a luminescent reaction. The light irradiation portions and the light receiving portions are, for example, provided so as to correspond to the antibody-immobilized beads 74, 76 and 78. The light irradiation portions and the light receiving portions are arranged to be opposed to each other via the antibody-immobilized beads 74, 76 and 78. Light fluxes from the light irradiation portions are respectively received by the light receiving portions via the beads 74, 76 and 78 in the antigen separation/immobilization tube 70. Based on the output signals from the light receiving portions, for example, absorbance data or emission intensity data regarding each of the beads 74, 76 and 78 is formed.

Assay System 5-1. Immunoassay System

The present invention provides an assay system comprising a pretreatment means for pretreating a specimen and an immunoassay means for performing an immunoassay of the specimen pretreated by the pretreatment means, and the immunoassay means comprises a labeling reaction means and a detection means. The assay system of the present invention is totally automated from the step of pretreating a specimen to the detection step, and a biologically-relevant substance in the specimen can be detected automatically. As already described above, regarding each of the pretreatment step and the assay step (a labeling reaction may be included), there are a plurality of variations, and the assay system is constituted according to the combination of such variations of the pretreatment step and the assay step.

As described above, as the means for removing a contaminant, which is the feature of the present application, the following 5 main embodiments can be employed: (i) a means for trapping and removing a nonspecific reaction factor utilizing magnetic particles to which an antibody against the nonspecific reaction factor is immobilized; (ii) a means for trapping and removing a nonspecific reaction factor utilizing an affinity gel to which an antibody against the nonspecific reaction factor is immobilized; (iii) a means for trapping and removing a nonspecific reaction factor utilizing a filter to which an antibody against the nonspecific reaction factor is immobilized; (iv) a means for trapping and removing a nonspecific reaction factor utilizing a plastic to which an antibody against the nonspecific reaction factor is immobilized; and (v) a means for decomposing a nonspecific reaction factor using a gel to which a reducing agent is immobilized. As the labeling reaction step, the following 2 main embodiments can be employed: (i) a labeling reaction means utilizing magnetic particles and a pipette chip; and (ii) a labeling reaction means utilizing an antigen separation/immobilization tube.

The detection step is selected depending on the means selected for the labeling reaction means. For example, when (i) a labeling reaction means utilizing magnetic particles and a pipette chip is selected for the labeling reaction means, a detection means utilizing magnetic particles and a pipette chip is preferably selected, and when (ii) a labeling reaction means utilizing an antigen separation/immobilization tube is selected for the labeling reaction means, a detection means utilizing an antigen separation/immobilization tube is preferably selected. Further, it is also possible to produce an assay system which has both (i) a labeling reaction means utilizing magnetic particles and a pipette chip and (ii) a labeling reaction means utilizing an antigen separation/immobilization tube. However, in this case, a mechanism of change between the pipette chip and the antigen separation/immobilization tube to be attached to a nozzle is further provided to the assay system, or both a nozzle for the pipette chip and a nozzle for the antigen separation/immobilization tube are provided to the assay system. Thus, it is possible to design at least 10 types of assay systems depending on the combination of the types of the means for removing the contaminant, the labeling reaction means and the detection means. The assay system may be produced with suitable modification according to the purpose of use, etc. Hereinafter, a particularly preferred embodiment will be described.

Figure 22:
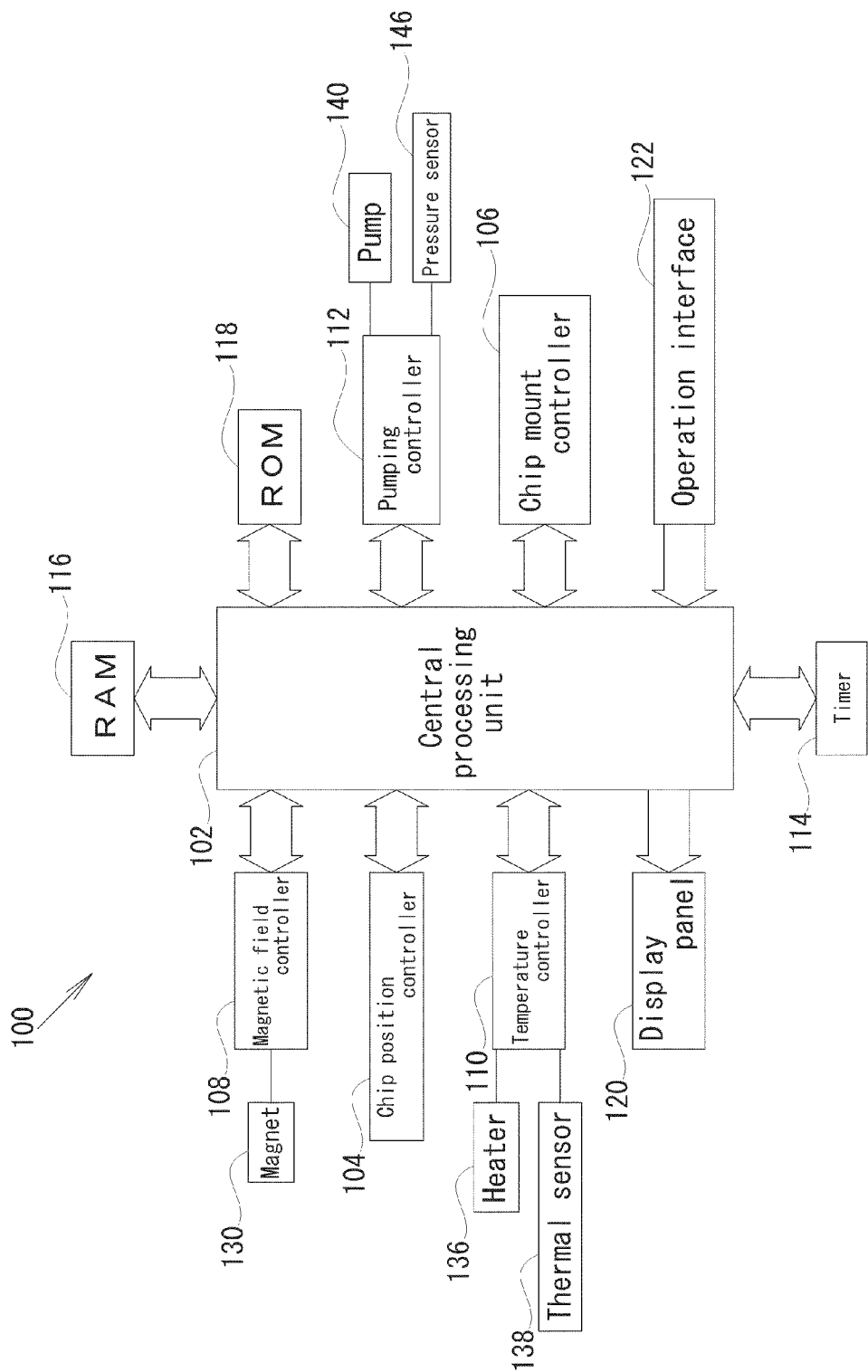
FIG. 22 is a block diagram showing the functions of the assay system.

FIG. 22 is a block diagram of an assay system in which the pretreatment step is carried out and then the assay step is carried out. Hereinafter, the system utilizing magnetic particles will be described. An assay system 100 has a central processing unit 102, a chip position controller 104, a chip mount controller 106, a magnetic field controller 108, a temperature controller 110, a pumping controller 112, a timer 114, a RAM 116, a ROM 118, a display panel 120, an operation interface 122, etc.

The chip position controller 104 has mutually orthogonal axes X, Y and Z, and the position of the nozzle is controlled by a stepping motor or a servomotor. The axes X and Y are approximately parallel to a well plate and mutually orthogonal, and the axis Z is approximately perpendicular to the well plate. At the time of the movement of the nozzle, for example, the nozzle is moved in two steps, i.e., a movement on the axes X and Y that are approximately parallel to the well plate, and a movement on the axis Z that is approximately perpendicular to the well plate.

In the ROM 118, various control programs are stored. According to an operation mode selected by a user via the operation interface 122, a control program is developed from the ROM 118 to RAM 116, and the central processing unit 102 controls each portion of the system 100 based on the control program developed in the RAM 116.

The display panel 120 displays items required to be provided to the user. For example, the display panel 120 can display the number of times of pumping at the time of the treatment of removing the contaminant in the specimen, time to be allowed to stand after suspension of the magnetic particles, the flow rate at the time of pumping, the amount to be sucked up and discharged, the rate of movement of the pipette chip, etc., and the user can confirm these items by the display. When set contents are desired to be changed, they can be changed by operation of the operation interface 122.

The timer 114 carries out timing according to a program read from the ROM 118. Timing is carried out, for example, when incubation or pumping is performed. By timing, each step is carried out accurately.

The magnetic field controller 108 manages the placement of the magnet 130 to control the strength of the magnetic field provided to the pipette chip. The magnetic field controller 108 has mutually orthogonal axes X, Y and Z, and the placement of the magnet 130 is managed by a stepping motor or a servomotor. The axes X and Y are approximately parallel to a well plate and mutually orthogonal, and the axis Z is approximately perpendicular to the well plate. At the time of the movement of the magnet 130, for example, the placement of the magnet 130 can be adjusted in two steps, i.e., a movement on the axes X and Y that are approximately parallel to the well plate, and a movement on the axis Z that is approximately perpendicular to the well plate. Usually, only the movement on the axes X and Y is carried out, but optionally, the movement on the axis Z can be carried out.

The temperature controller 110 has a heater 136, a thermal sensor 138, etc., and manages the temperature of the liquid held in the pipette chip. The heater 136 is allowed to produce heat by electric power supplied by the temperature controller 110. The thermal sensor 138 transmits a temperature signal to the temperature controller 110 depending on the temperature of the liquid held in the pipette chip. The temperature controller 110 detects the temperature based on the temperature signal from the thermal sensor 138 and adjusts the electric power supplied to the heater 136.

The chip mount controller 106 performs attachment of the pipette chip to the nozzle and detachment of the pipette chip from the nozzle. The chip mount controller 106 is placed at a position which is remote from the well plate to some extent, so that contamination is prevented if the liquid is spattered from the pipette chip at the time of exchange of the pipette chip. The chip mount controller 106 has a gripping portion for gripping the pipette chip and a chip preparation portion for preparing another new pipette chip. When the nozzle is moved upward along the axis Z with the pipette chip being gripped by the gripping portion, the pipette chip is detached from the nozzle. Next, the bared nozzle is moved on the axes X and Y to move to a position above a new pipette chip. At the chip preparation portion, the new pipette chip is held with a mount portion side up and a tip portion side down. When the nozzle is moved downward along the axis Z, the mount portion of the new pipette chip is attached to the nozzle. Examples of embodiments of engagement between the nozzle and the pipette chip include an engagement form utilizing a latch and a notch with which the latch is engaged, an engagement form utilizing a boss and a rib, and an engagement form utilizing a male screw and a female screw. Any suitable engagement form may be selected.

The pumping controller 112 has a pump 140 and a pressure sensor 146, and controls sucking up and discharging of the liquid performed via the nozzle and the pipette chip attached to the nozzle. The pump 140 has a housing formed into a cylindrical shape, a piston that is movably fitted into the housing and a motor for driving the piston. The inside of the housing communicates with the opening of the nozzle. The movement of the piston is controlled, for example, by a servomotor, and driving of the servomotor is controlled by a drive control signal from the pumping controller 112. When the piston is activated, it becomes possible to suck up or discharge the liquid through the opening of the nozzle.

In the opening of the nozzle, a pressure sensor 146 for detecting the pressure is provided, and the pressure sensor 146 transmits a pressure signal to the pumping controller 112. The pumping controller 112 monitors the pressure based on the pressure signal from the pressure sensor 146. In this constitution, for example, when the tip portion of the pipette chip is immersed in the specimen in the well, the pressure detected by the pumping controller 112 exceeds a predetermined threshold, and in response to this, the drive control signal is transmitted to the servomotor. Also at the time of sucking up and discharging the specimen, the pressure sensor 146 constantly transmits the pressure signal to the pumping controller 112. Therefore, the pumping controller 112 can control driving of the servomotor with high accuracy, and monitors levels of the pressure of sucking up the specimen and the pressure of discharging the specimen, thereby performing management so as to allow sucking up and discharging to be carried out within a predetermined range. Note that the means for the treatment of removing the contaminant is constituted by the magnetic field controller 108, the pumping controller 112, the magnetic particles to which the antibody against the nonspecific reaction factor is immobilized, etc. The means for stirring is constituted by the pipette chip, the pumping controller 112, the pump 140, the pressure sensor 146, etc. Further, the means for separation is constituted by the magnetic field controller 108, the magnet 130, etc.

The action of the above-described constitutions will be described. When the step of the treatment of removing the contaminant is started, the tip portion of the pipette chip is immersed in the specimen in the well 12, and based on the pressure signal from the pressure sensor 146, the pump 140 is activated. After the specimen is sucked up into the pipette chip, the pipette chip is controlled to be moved to the well 12 in which the solution of magnetic particles for pretreatment is held, and the tip portion of the pipette chip is immersed in the solution of magnetic particles for pretreatment. Based on the pressure signal from the pressure sensor 146, immersion of the tip portion of the pipette chip is detected, and then the piston of the pump 140 is activated to start pumping. When the pumping is started, the magnetic particles to which the antibody against the nonspecific reaction factor is immobilized are dispersed, thereby forming a suspension.

After a predetermined amount of time passes after the formation of the suspension, the pump 140 is activated and the suspension is sucked up into the pipette chip 10. After the suspension is sucked up into the pipette chip 10 and the pump 140 is stopped, the magnet 130 is moved toward the holding portion of the pipette chip and the magnetic particles for pretreatment are fixed to one position on the inner wall surface. The pump 140 is activated with the magnetic particles for pretreatment being fixed to one position by the magnet, thereby discharging the liquid into the well. In this way, the contaminant is removed and the magnetic particles for pretreatment to which the nonspecific reaction factor is bound are separated from the specimen to prepare an assay sample to be assayed.

After obtaining the assay sample in which the contaminant contained in the specimen has been removed, magnetic particles for specific reaction are added to the assay sample to extract the antigen from the specimen. Further, antigen-bound magnetic particles are labeled with the enzyme-labeling antibody to obtain labeling antibody-bound magnetic particles. The obtained labeling antibody-bound magnetic particles are added to the substrate solution to detect absorbance, etc.

Thus, by pumping the specimen mixed with the magnetic particles to which the antibody against the nonspecific reaction factor is immobilized, the specimen is stirred and the magnetic particles move in the specimen. Therefore, the frequency that the magnetic particles to which the antibody against the nonspecific reaction factor is immobilized encounter the nonspecific reaction factor in the specimen is increased, and the nonspecific reaction factor can be bound to the antigen against the nonspecific reaction factor more certainly. Further, by separating the magnetic particles to which the nonspecific reaction factor is bound from the specimen using the magnet, the nonspecific reaction factor can be efficiently removed from the specimen. In addition, the steps from the pretreatment of the specimen to the immunoassay can be carried out collectively and continuously, and a highly convenient system can be provided to users. Moreover, since the pretreatment of the specimen is carried out in accordance with the pumping mechanism, chip and well used in the immunoassay step, the pumping mechanism and the like can be used for two purposes when constructing a system in which the pretreatment step is integrated into the immunoassay step, and therefore, it is possible to prevent the system from becoming too enormous.

Further, as described above, the movement of the piston driven at the time of pumping is controlled by the servomotor based on the pressure signal from the pressure sensor 146. Therefore, the amount of the liquid sucked up at the time of pumping, the amount of the liquid discharged, the pressure of sucking up and the pressure of discharging can be controlled with high accuracy, and the flow of the liquid can be rapidly controlled. Therefore, dispersion of the magnetic particles as described above can be carried out in a short time, and reduction in pretreatment time and the like can be realized. Further, since pumping of the specimen is carried out in a state in which the opening at the tip portion of the pipette chip is immersed in the specimen, bubbling of the specimen can be reduced, and inclusion of atmosphere in contact with the specimen in the specimen can be reduced.

Further, pumping is carried out using a pipette chip and a well, and the sizes of the pipette chip and well may correspond to the sizes of the pipette chip and well used in the labeling reaction step or the assay step. By using the pipette chips of the same size and the wells of the same size, size reduction in the assay system can be expected. In the explanation above, the magnetic particles to which the antibody against the nonspecific reaction factor is immobilized are used, but a micro-sized small sphere to which the nonspecific reaction factor is immobilized may also be used. In this case, by using a filter or the like having a mesh size with which the small sphere cannot be passed through, the small sphere to which the nonspecific reaction factor is immobilized can be separated from the specimen.

The assay system in which the labeling reaction step is carried out using the magnetic particles to which the antibody against the antigen is immobilized basically has the same constitution as that shown in FIG. 22, except that the pattern of movement of the magnet and the like are different.

By using such an apparatus, for example, in the pretreatment step, the specimen is flowed through the support to which the antibody against the nonspecific reaction factor is immobilized or the support to which the reducing agent is immobilized by pumping. Therefore, corresponding to the number of times of pumping the specimen, the number of times of being flowed through the support to which the antibody against the nonspecific reaction factor is immobilized or the support to which the reducing agent is immobilized is increased, and the possibility that the nonspecific reaction factor may encounter the antibody against the nonspecific reaction factor or the reducing agent is increased. Therefore, when using the support to which the antibody against the nonspecific reaction factor is immobilized, the nonspecific reaction factor can be bound to the antibody against the nonspecific reaction factor more certainly to allow the nonspecific reaction factor to be trapped by the support, and when using the support to which the reducing agent is immobilized, the nonspecific reaction factor can be decomposed more certainly. Further, as described above, the movement of the piston driven at the time of pumping is controlled by the servomotor based on the pressure detection signal from the pressure sensor. Therefore, the amount of the liquid sucked up at the time of pumping, the amount of the liquid discharged, the pressure of sucking up and the pressure of discharging can be controlled with high accuracy, and the flow of the liquid can be rapidly controlled. Therefore, trapping of the nonspecific reaction factor or decomposition of the nonspecific reaction factor as described above can be carried out in a short time, and time required for the pretreatment can be more reduced. Further, pumping is carried out using a pipette chip and a well, and the sizes of the pipette chip and well may correspond to the sizes of the pipette chip and well used in the labeling reaction step. By using the pipette chips of the same size and the wells of the same size, the size of the assay system can be more reduced. Note that the system explained above is just an example, which can be suitably changed.

When immunoassay is automatically performed using the assay system in this way, by carrying out sucking up and discharging of the specimen in the pretreatment with the tip portion of the pipette chip being immersed in the well, bubbling and spattering of the specimen can be reduced. Further, all of the step of the treatment of removing the contaminant using the first support, the step of preparing the second support, the labeling reaction step and the assay step are consistently carried out in limited places in the apparatus, for example, in the well and the pipette chip, or in the well, the pipette chip and the antigen separation/immobilization tube. Therefore, the treatment process is simplified, and in addition, there is a high possibility that mixing of bacteria and the like may be reduced and reduction of contamination can be expected.

In the explanation above, the embodiment in which the nonspecific reaction factor is removed from the specimen is exemplified. However, the present invention is not limited thereto, and an antigen of interest may be extracted from the specimen. Magnetic particles to which an antibody which specifically reacts with the antigen of interest is immobilized are added to and suspended in the specimen. After the suspension, the specimen is sucked up into the pipette chip and the magnet is moved toward the pipette chip to constrain the magnetic particles. After constraining the magnetic particles, the liquid in the pipette chip is discharged, and the antigen bound to the magnetic particles is washed, thereby removing the contaminant. Such a pretreatment can also be carried out.

5-2. System for Assaying Nucleic Acid

In the explanation above, the assay system in which the pretreatment step of removing the nonspecific reaction factor from the specimen is carried out before the immunoassay is exemplified, but the present invention can also be used for an assay system for nucleic acids. As the assay system for nucleic acids, for example, in the Stanford type system, on a microarray chip on which probe DNAs are arranged, a target DNA solution is spotted to cause hybridization, and the microarray chip on which the target DNA solution is spotted is detected by a light receiving element or an image sensor to obtain detection data. In order to more clarify a signal of the obtained detection data, it is necessary to more certainly cause hybridization between the probe DNA and the target DNA. For certain hybridization between the probe DNA and the target DNA on the microarray chip, removal of the contaminant in the specimen is one of important problems. The smaller the amount of the contaminant mixed in the target DNA solution spotted on the microarray chip is, the higher the quality of the detection data obtained is. The present invention can be used for this pretreatment of removing the contaminant in the target DNA solution.

For example, for removing the contaminant contained in the target DNA solution, the specimen containing the target DNA is held in a well, and magnetic particles to which a substance having affinity to the contaminant in the specimen is immobilized are added to the specimen in the well using the pipette chip, followed by pumping.

After pumping, the specimen is sucked up into the pipette chip, and the magnet is moved toward the pipette chip to constrain the magnetic particles. By discharging the liquid into the well with the magnetic particles being constrained, the contaminant can be removed from the specimen. By preparing the target DNA solution from the specimen from which the contaminant has been removed, the contaminant contained in the target DNA solution can be reduced. Further, when the steps from the step of preparing the target DNA solution to the step of obtaining the detection data are consistently automated in one system, the treatment process is simplified, and in addition, prevention of contamination and improvement of convenience can be expected. In the explanation above, DNA is exemplified as a target, but this technique can also be used for preparing other nucleic acid targets such as cRNA and mRNA.

EMBODIMENTS

As explained above, by changing the combination of the embodiment of the pretreatment step and the embodiment of the assay step, it is possible to produce assay systems of various embodiments. Some examples of possible combinations of embodiments of the pretreatment step, the labeling reaction step and the assay step will be described below.

Embodiment 1

Figure 23:
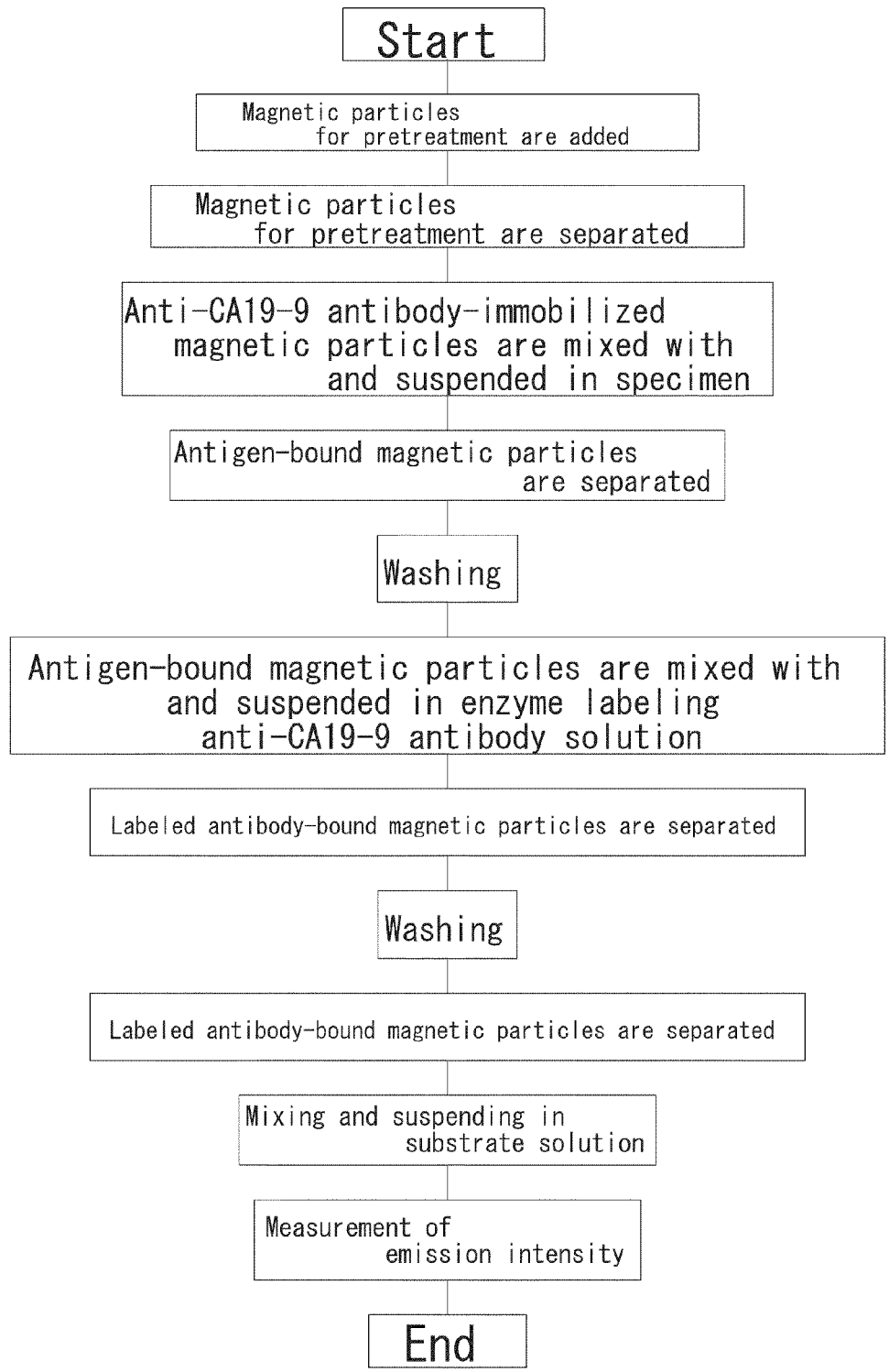
FIG. 23 is a flow chart of a case where a pretreatment is carried out using magnetic particles to which an antibody against a nonspecific reaction factor is immobilized and subsequently an immunoassay is carried out.

An example in which CA19-9 that is utilized at the time of cancer tests for the digestive system is used as an antigen will be described. Naturally, the present invention is not limited to this embodiment. FIG. 23 is a flow chart of a case where a pretreatment is carried out using magnetic particles to which an antibody against a nonspecific reaction factor is immobilized and subsequently an immunoassay is carried out. As shown in FIG. 23, in the pretreatment of a specimen, a serum is used as the specimen, and magnetic particles to which at least one of protein A (antibody against a nonspecific reaction factor) and protein G (antibody against a nonspecific reaction factor) that can bind to globulin (nonspecific reaction factor) contained in the specimen is immobilized (hereinafter referred to as "magnetic particles for pretreatment") are used as the magnetic particles to which the antibody against the nonspecific reaction factor is immobilized.

Firstly, the magnetic particles for pretreatment (first support) are mixed with the serum in a well, and sucking up and discharging the mixture is repeated for suspending. After suspending, the suspension is sucked up into a holding portion of a pipette chip, a magnetic field is provided to the holding portion to constrain the magnetic particles at one position in the holding portion, and the remaining solution is discharged into the well. In this way, the globulin contained in the specimen can be trapped by the protein A or protein G of the magnetic particles for pretreatment and removed. When it is desired that the globulin is removed with higher accuracy, this step of the treatment of removing the contaminant may be suitably repeated. Note that when removing the globulin and the like contained in the specimen with higher accuracy, it is also effective, for example, to use a protein-removing agent such as an enzyme in combination.

Magnetic particles for specific reaction to the surface of which an anti-CA19-9 antibody is immobilized (second support) are mixed with and suspended in the serum obtained by removing the globulin. The CA19-9 antigen in the treated serum binds to the anti-CA19-9 antibody, and therefore the CA19-9 antigen is trapped by the magnetic particles for specific reaction. The suspension is sucked up into the holding portion of the pipette chip, a magnetic field is provided to the holding portion to constrain the antigen-bound magnetic particles at one position in the holding portion, and the remaining solution is discharged into the well. The antigen-bound magnetic particles, which are held in the holding portion, and to which the CA19-9 antigen has been bound, are mixed with a washing solution held in another well and washing is performed. After washing, the magnetic field is provided to the antigen-bound magnetic particles to which the CA19-9 antigen has been bound, and they are separated from the washing solution. The antigen-bound magnetic particles separated from the washing solution are mixed with and suspended in an enzyme labeling anti-CA19-9 antibody solution held in another well. In this way, the CA19-9 antigen can form sandwich binding with the anti-CA19-9 antibody and the enzyme labeling anti-CA19-9 antibody.

The magnetic field is provided to the labeled antibody-bound magnetic particles having the CA19-9 antigen that has been subjected to sandwich binding, and the labeled antibody-bound magnetic particles are separated from the suspension. The labeled antibody-bound magnetic particles separated are mixed with a washing solution in another well and washing is performed. After washing, the magnetic field is provided to the labeled antibody-bound magnetic particles having the CA19-9 antigen that has been subjected to sandwich binding, and the labeled antibody-bound magnetic particles are separated from the washing solution. The labeled antibody-bound magnetic particles are mixed with and suspended in a substrate solution held in another well. After the elapse of the enzyme reaction time, the suspension is subjected to photometry to measure absorbance, emission intensity, etc.

Embodiment 2

Figure 24:
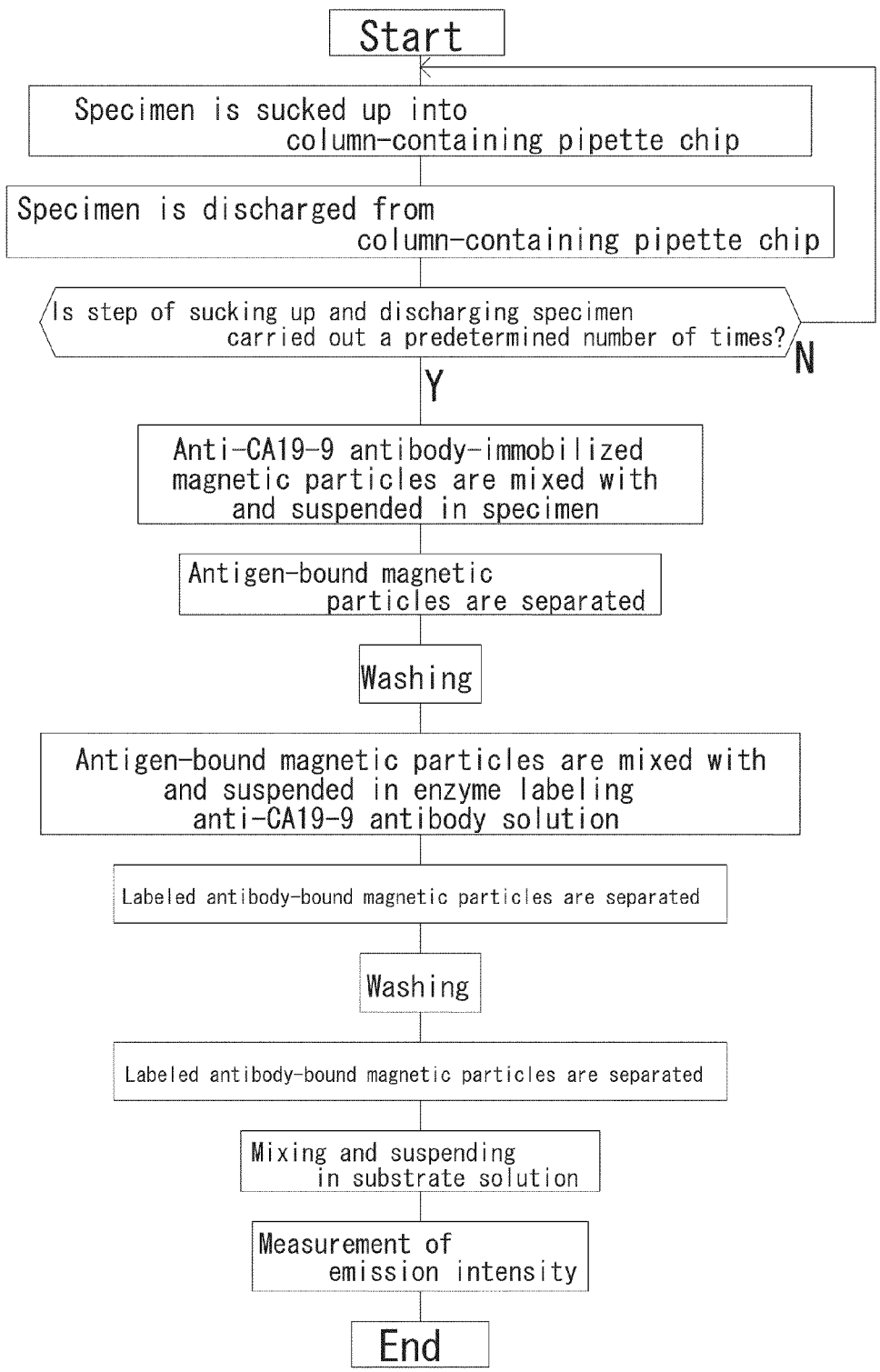
FIG. 24 is a flow chart of a case where a pretreatment is carried out using a column to which an antibody against a nonspecific reaction factor is immobilized and subsequently an immunoassay is carried out.

FIG. 24 is a flow chart of a case where a pretreatment is carried out using a column to which an antibody against a nonspecific reaction factor is immobilized and subsequently an immunoassay is carried out. As shown in FIG. 24, like Embodiment 1, a serum is used as the specimen, and an affinity column (first support) to which at least one of protein A and protein G that can bind to globulin contained in the specimen is immobilized is used to treat the serum. The serum in a well is sucked up into a column-containing pipette chip, and via an affinity column, the serum held in the pipette chip is discharged into the well. When such sucking up and discharging of the serum are carried out a predetermined number of times, the globulin contained in the serum can be bound to the protein A or protein G of the affinity gel and removed. After that, the treated serum discharged into the well can be subjected to a reaction step in a manner similar to that in Embodiment 1.

Embodiment 3

In this embodiment, the pretreatment is carried out by using any one of the methods of the treatment of removing the contaminant already described in FIGS. 8-15, and the assay is carried out using the antigen separation/immobilization tube shown in FIG. 21, wherein a plurality of antigens are simultaneously bound to respective antibody-immobilized beads. After a certain period of time, a washing solution in another well is sucked up to wash the antibody-immobilized beads. After washing the antibody-immobilized beads, an enzyme labeling solution is sucked up into the antigen separation/immobilization tube. After the enzyme labeling solution is sucked up into the tube and an enzyme labeling antibody is bound to each antigen, a washing solution in another well is sucked up to wash the antibody-immobilized beads. After washing, a substrate solution is sucked up into the antigen separation/immobilization tube. After the elapse of sufficient time, absorbance, emission intensity, etc. of each of the antibody-immobilized beads which have been subjected to sandwich binding are measured.

In this way, by treating the specimen using the separation/immobilization tube in which a plurality of types of antibody-immobilized beads are arranged, a plurality of antigens can be trapped at a time. Therefore, the operation can be simplified, and in addition, the time required for detecting the antigens in the specimen can be dramatically reduced.

In the present invention, the pretreatment may be carried out using any one of the methods of the treatment of removing the contaminant exemplified in FIGS. 8-15, and the assay may be carried out by conventional ELISA after the pretreatment. For example, the treatment of removing the contaminant is carried out using any one of the methods of the treatment of removing the contaminant shown in FIGS. 8-15. In another well, the antibody against the antigen is immobilized in advance, and when a serum from which the nonspecific reaction factor has been removed by the treatment of removing the contaminant is added to this well, the antigen in the treated specimen can bind to the antibody in the well. After washing, a labeling solution containing an enzyme labeling antibody is added to this well, and the enzyme labeling antibody can bind to the antibody-bound antigen. After washing, a substrate solution is added to cause color development, and a chromogenic reaction terminating solution is suitably added. The well in which color development has been caused is set in an absorbance measurement device to measure absorbance, etc. An assay system for carrying out such a process can also be realized.

Embodiment 4

Figure 25:
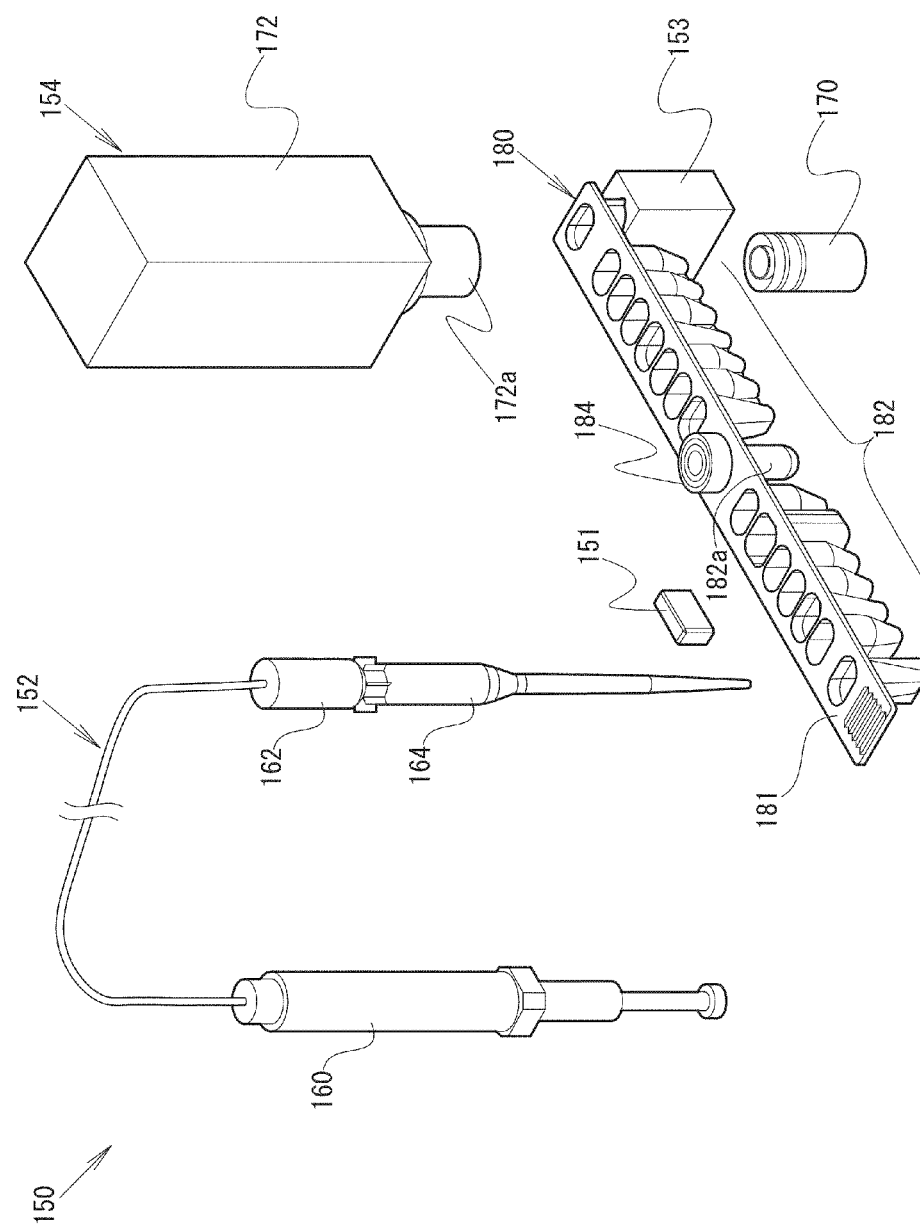
FIG. 25 is a schematic view of an assay system utilizing a cartridge in which magnetic particles for pretreatment and a substrate solution are held in advance.
Figure 26:
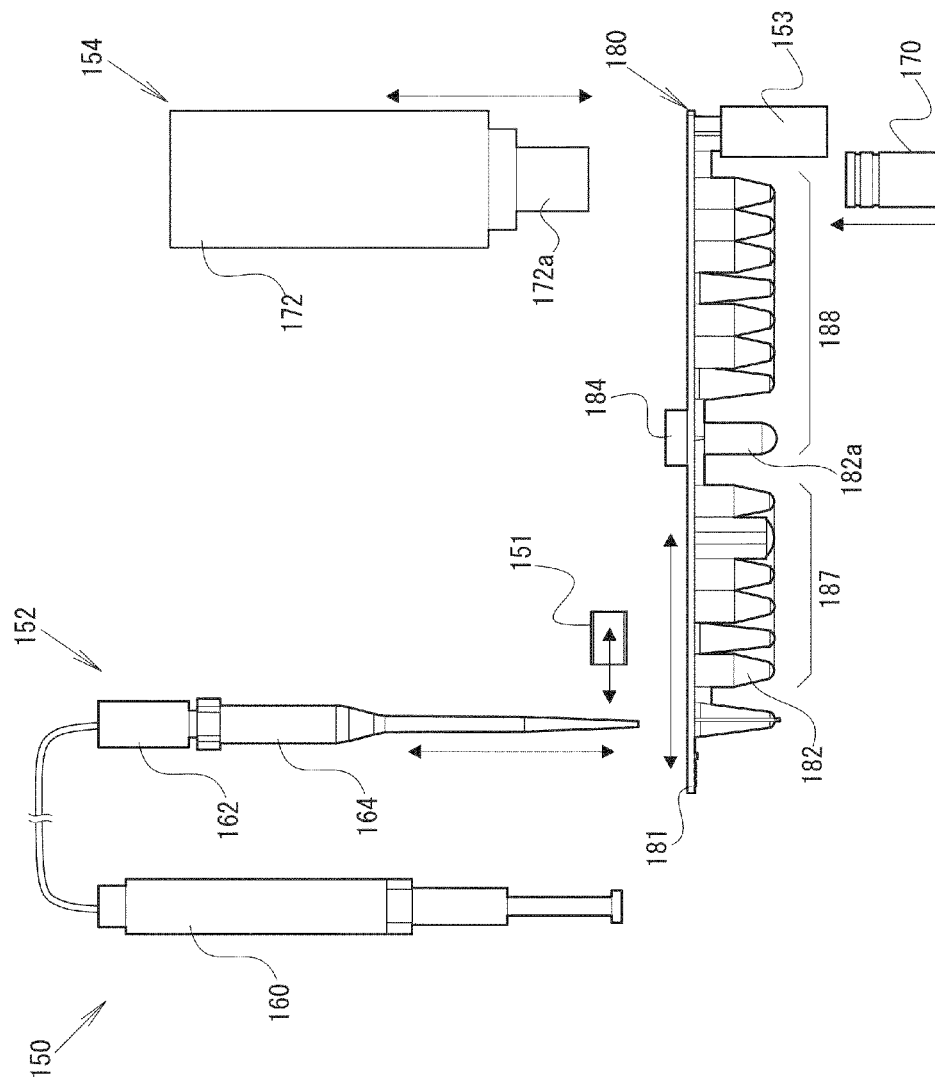
FIG. 26 is an explanatory drawing for schematically explaining a mode of operation of the assay system utilizing the cartridge.

In order to perform the process from the pretreatment of the specimen to the detection of the substance of interest, in the present invention, a series of steps including the pretreatment of the specimen may be carried out using a cartridge into which a holding portion for holding the specimen, a holding portion for holding the magnetic particles for removing the contaminant from the specimen in advance, a holding portion for holding the magnetic particles to which the antibody for labeling the antigen in the specimen is bound in advance, a holding portion for holding the substrate solution in advance, etc. are integrated in advance. Further, it is also possible to allow the assay system for specimen using the cartridge to consistently carry out the step of the treatment of removing the contaminant and the subsequent labeling reaction step or the assay step comprising the labeling reaction step. Such an assay system using the cartridge will be described below. FIG. 25 is a schematic view of an assay system utilizing a cartridge in which magnetic particles for pretreatment and a substrate solution are held in advance. FIG. 26 is an explanatory drawing for schematically explaining a mode of operation of the assay system utilizing the cartridge. As shown in FIGS. 25 and 26, an assay system 150 has a magnet 151, a dispensing apparatus 152, a heat block 153, a detection apparatus 154, an arrangement control apparatus, a central control apparatus, etc.

The dispensing apparatus 152 has a pump 160 and a nozzle 162, and on the nozzle 162, a pipette chip 164 can be detachably mounted. The detection apparatus 154 has a photomultiplier tube (hereinafter referred to as "PMT") 172 and a light source 170. The PMT 172 receives light from the light source 170, and in response to this, a signal is outputted from the PMT 172. As shown in FIG. 26, for example, the nozzle 162, the PMT 172 described below and the light source 170 are controlled by the central control apparatus to move in the vertical direction, and the magnet 151 and the cartridge 180 are controlled by the central control apparatus to move in the horizontal direction.

The cartridge 180 has a base panel 181 that is formed into an elongate shape and a plurality of holding portions 182, and the plurality of holding portions 182 are arranged from one end to the other end of the panel 181 in the longitudinal direction. In the cartridge 180, the base 181 formed on the base panel and the plurality of holding portions 182 are integrally formed. Each holding portion 182 has an opening on the base panel to allow the pipette chip 164 to be received.

As the holding portions 182 provided to the cartridge 180, a holding portion for holding a solution of magnetic particles for pretreatment, a holding portion for holding a specimen, a holding portion for holding a solution of magnetic particles to which an antibody for labeling is bound, a holding portion for holding a washing solution for washing an antigen binding to the magnetic particles for labeling, a holding portion for holding a substrate solution for causing a chromogenic reaction, etc. are provided. The types of the holding portions provided to the cartridge 180 are not limited to the examples described above. For example, holding portions may be provided to the cartridge to allow only the pretreatment to be carried out.

A holding portion 182a for measuring absorbance is provided to the base panel 181 (for example, the central portion thereof), and on the upper side of the holding portion 182a, a mount 184 for the PMT 172 to be mounted is positioned. The base panel 181 and the holding portions 182 are protected from light by an aluminum seal or the like, and the PMT 172 is fitted into the mount 184 in a state where it is shielded from light. The bottom portion of the holding portion 182a for detection can be fitted into the light source 170 in a state where it is shielded from light. Irradiation light from the light source 170 fitted to the bottom portion of the holding portion 182a for detection is received by the PMT, thereby counting the number of photons.

The position of the cartridge 180 relative to the nozzle 162 and the PMT 172 is determined by a cartridge controller (not shown). The cartridge controller controls the cartridge 180 to move in the horizontal direction and determines the position of the cartridge 180 relative to the dispensing apparatus 152 and the detection apparatus 154. By controlling the position of the cartridge 180, for example, the cartridge can be appropriately located relative to the pipette chip, and therefore, pipetting and measurement of absorbance in the step of the treatment of removing the contaminant, the labeling reaction step and the detection step can be smoothly carried out The holding portions 182 of the cartridge 180 has, for example, a first portion 187 for carrying out the treatment of removing the contaminant and a second portion 188 for carrying out the labeling reaction step and the detection step. A holding portion to which a heater 153 can be fitted is provided to the cartridge 180 in order to perform incubation, but this holding portion for the heater may be suitably omitted according to the purpose of the assay system.

Figure 27:
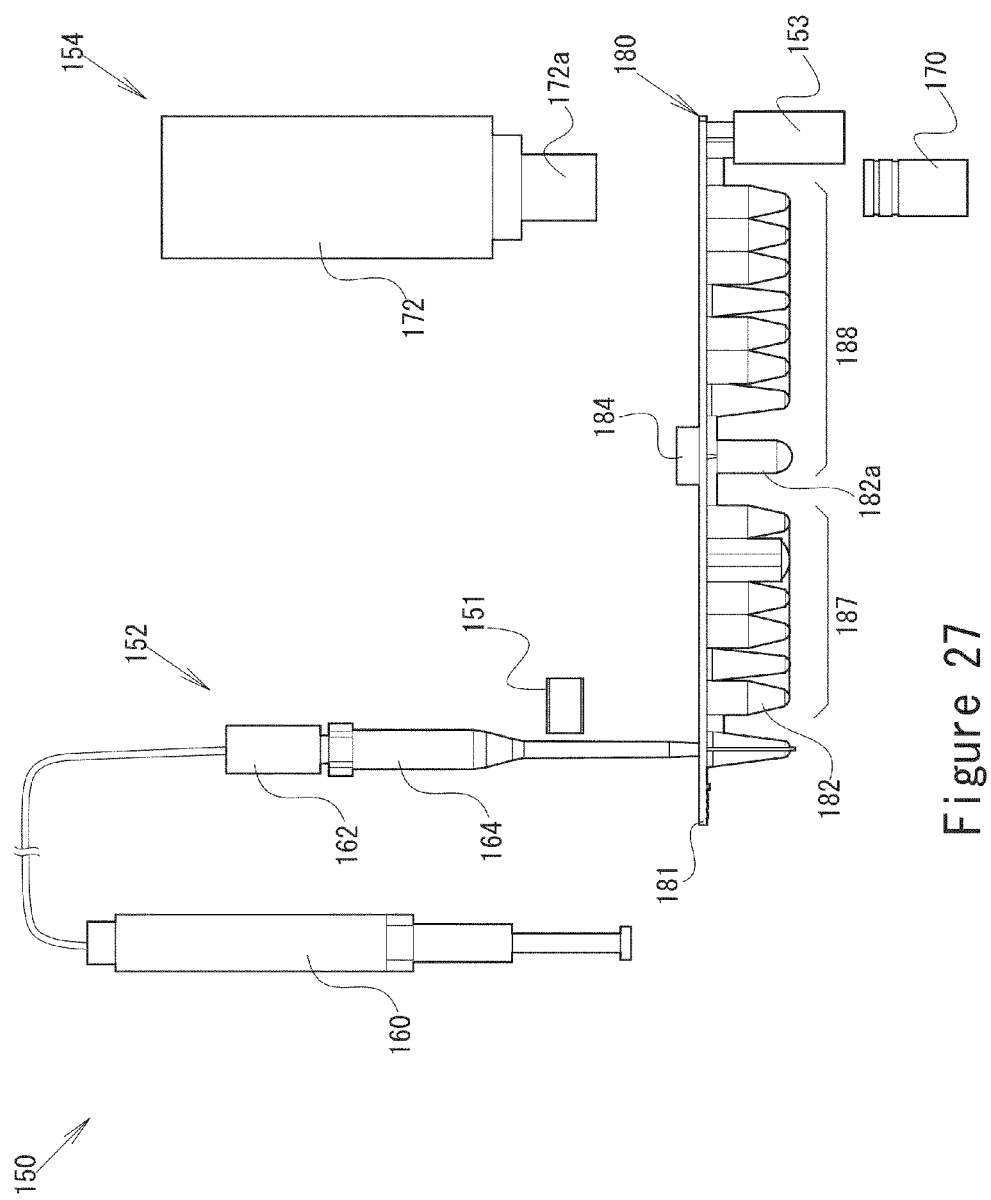
FIG. 27 is an explanatory drawing for showing the pretreatment step in the assay system utilizing the cartridge.

Hereinafter, the action of the assay system 150 utilizing the cartridge 180 will be described. After mounting the cartridge 180, a solution of magnetic particles held in a first holding portion of the cartridge 180 in advance is sucked up into the pipette chip 164 and discharged into a second holding portion, followed by pumping. FIG. 27 shows the pretreatment step in the assay system utilizing the cartridge. As shown in FIG. 27, after pumping, the liquid in the second holding portion is sucked up into the pipette chip 164, the magnetic particles to which the contaminant is bound are separated by the magnet 151, and an assay sample from which the contaminant has been removed is discharged into a third holding portion. In the third holding portion, a mixture of the magnetic particles for labeling and the assay sample is held, and this mixture is pumped and sucked up into the pipette chip. After sucking up the mixture, the antigen-bound magnetic particles are separated by the magnet and put into a fourth holding portion. The antigen binding to the magnetic particles is washed with a washing solution held in the fourth holding portion in advance, and a mixture of the washing solution and the antigen is sucked up into the pipette chip. From the mixture sucked up into the pipette chip, the antigen-bound magnetic particles are separated by the magnet 151, and the antigen is put into a fifth holding portion 182a for detection.

Figure 28:
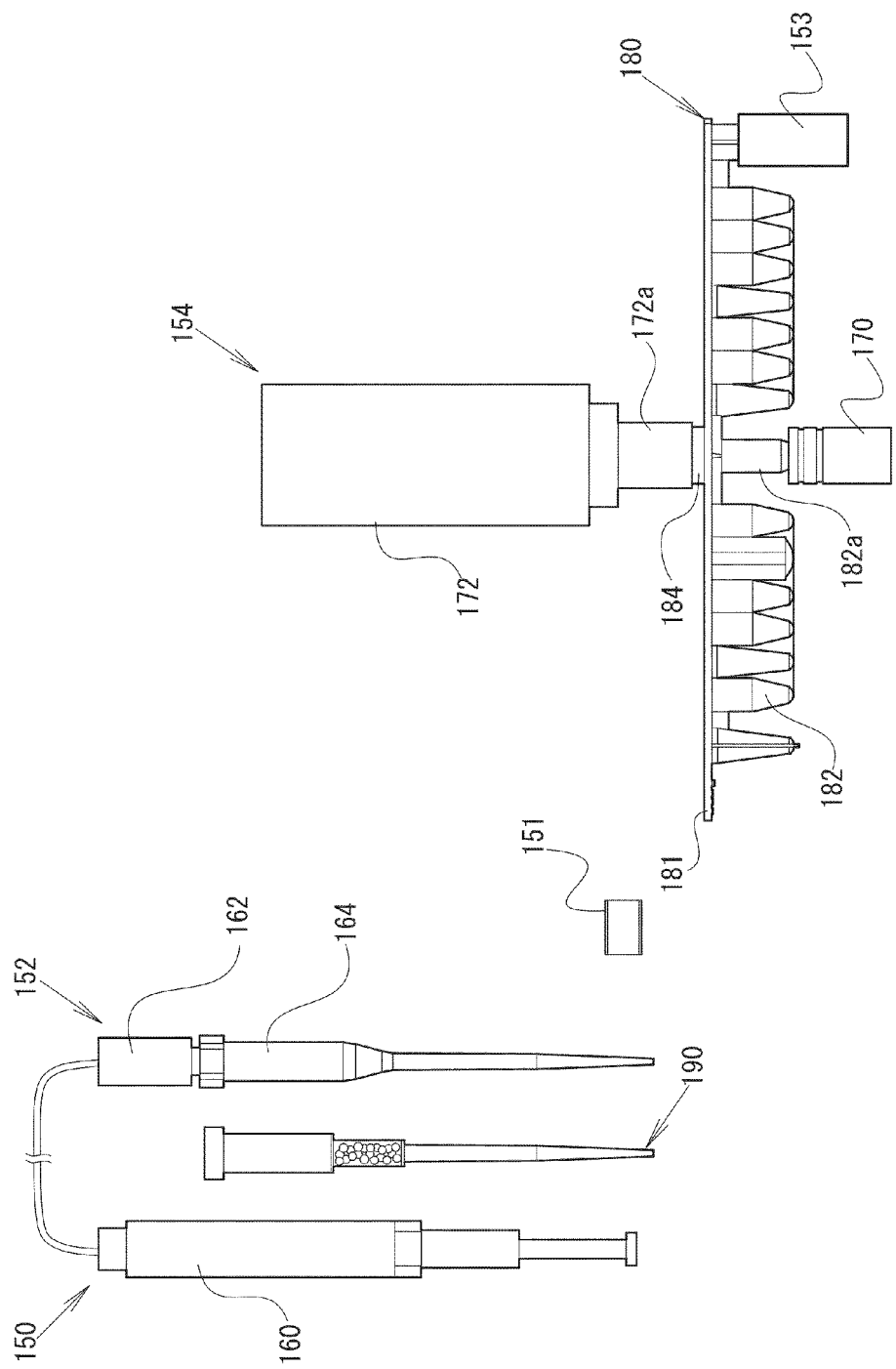
FIG. 28 is an explanatory drawing for showing the assay step utilizing the cartridge.

FIG. 28 shows the assay step in the assay system utilizing the cartridge. As shown in FIG. 28, a substrate solution is held in the fifth holding portion 182a in advance, and the substrate solution is reacted with the antigen to cause color development, thereby detecting absorbance. When removing the contaminant in the specimen, in the case where it is desired to remove the contaminant contained in the specimen using a membrane, affinity column or reducing agent-immobilized gel, a pipette chip having a membrane, a pipette chip containing an affinity column, or a pipette chip containing a reducing agent-immobilized gel is attached to the nozzle 162 to treat the specimen. For example, as shown in FIG. 28, when removing the contaminant contained in the specimen using a pipette chip 190 having a membrane, the pipette chip 190 having the membrane is fitted to the nozzle 162 to treat the specimen. In this way, it is possible to ensure variation of the technique of removing the contaminant in the assay system 150, and convenience of the system can be improved.

Thus, the holding portions that are required in a series of steps including the step of pretreating the specimen are provided to the cartridge 180 in advance, and this cartridge 180 is mounted to the assay system 150 to be used. In this way, users can save effort to prepare a solution of magnetic particles, a washing solution, etc., and convenience of the operation of the assay system 150 can be improved.

In the embodiment above, the pretreatment is carried out by moving the pipette chip in the vertical direction and moving the cartridge in the horizontal direction, but the technique of carrying out the pretreatment is not limited thereto. For example, the pretreatment of the specimen may be carried out by fixing the cartridge and moving the pipette chip in the horizontal direction and vertical direction. By fixing the cartridge, designers can save effort to design the system so that the liquid in the well is not spattered to the outside, and it becomes possible to provide a more convenient assay system.

Figure 29:
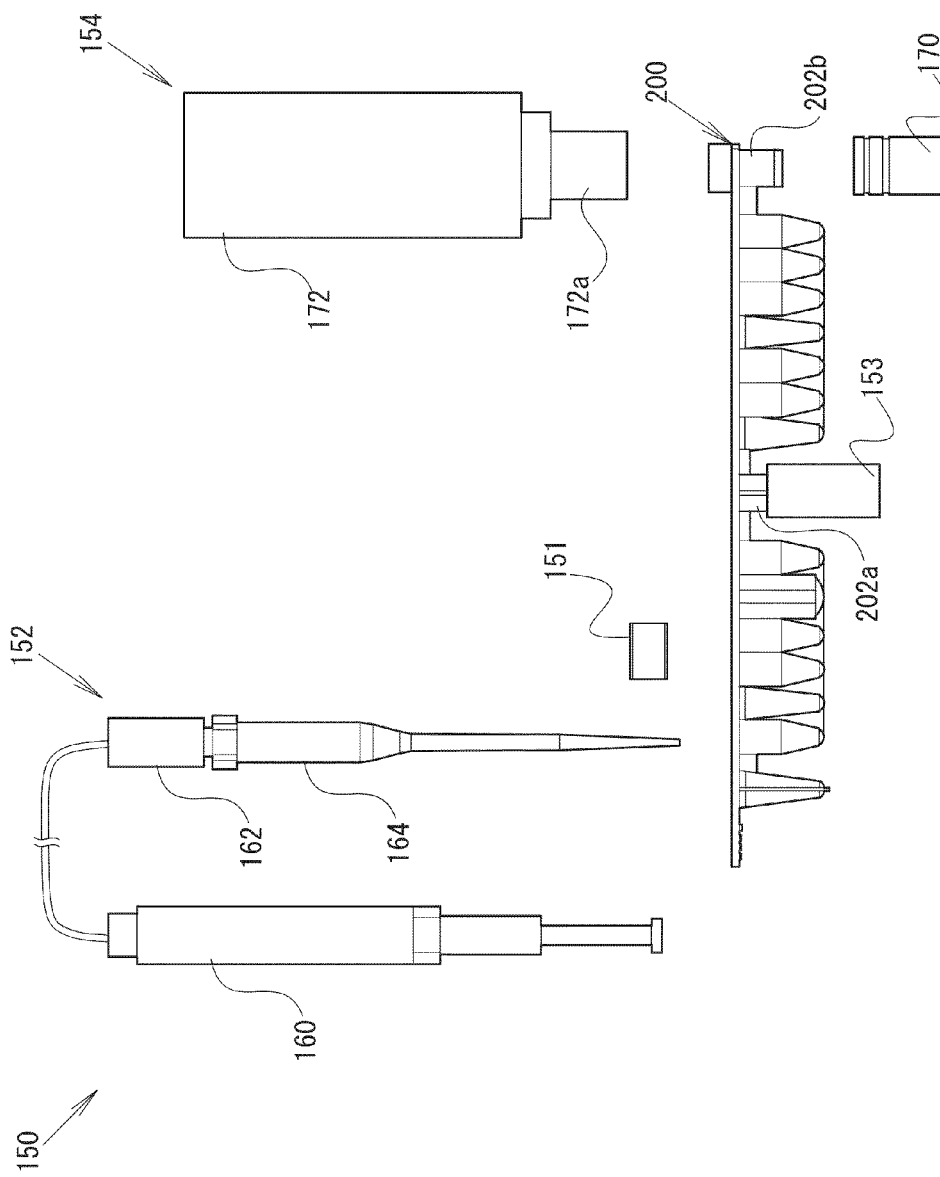
FIG. 29 is an explanatory drawing for schematically explaining a cartridge having another form.

In the embodiment 4 above, the cartridge 180, in which the holding portion 182a in which the substrate solution is held in advance is provided at the central portion and the holding portion to which the heater 153 for culturing can be fitted is provided at the end portion, is exemplified, but the arrangement order of the holding portions in the cartridge is not limited thereto. FIG. 29 is a schematic view of a cartridge having another form. For example, as shown in FIG. 29, the form may be suitably changed depending on the structure of the assay system to which the cartridge is mounted. In the form shown in FIG. 29, a holding portion 202a, to which a heater 153 can be fitted, is provided at the central portion of a cartridge 200, and a holding portion 202b, in which a substrate solution is held in advance, is provided at the end portion. By suitably changing the arrangement order of the holding portions in this way in view of the content of the treatment, the treatment of the specimen can be carried out more efficiently.

Further, in the embodiment described above, the solution of magnetic particles is held in the holding portion 182 in advance, but it is also possible to use a pipette chip in which the solution of magnetic particles is held in advance or to use a pipette chip having a support for adsorbing the contaminant in the specimen in order to carry out the pretreatment to of the specimen. In this case, it is required to suitably change the structure of the holding portions of the cartridge corresponding to such a pipette chip.

Further, in the explanation above, the cartridge 180 in which the first portion 187 and the second portion 180 are integrally formed is exemplified, but the structure may be such that the first portion 187 and the second portion 188 can be freely combined. By providing the structure in which the first portion 187 and the second portion 188 can be freely combined, users can select any of the first portion, the second portion, and the combination of the first portion and the second portion according to individual cases (the case where only the treatment of removing the contaminant from the specimen is desired to be carried out, the case where only the steps from the labeling reaction step to the detection step (excluding the pretreatment step) are desired to be carried out, and the case where all the steps are desired to be carried out), and it is possible to provide a more convenient assay system.

In the embodiment described above, CA19-9 is used as the antigen targeted for detection, but the detection target is not limited thereto, and examples thereof include simple protein such as rheumatoid factor, free thyroxine (F-T4), thyroid-stimulating hormone (TSH), insulin and α-fetal protein (AFP), complex protein, steroid hormone and peptide hormone.

6. Nucleic Acid Assay System

As another example of the present invention, an embodiment in which the present invention is used in the field of nucleic acid detection will be described below. When a nucleic acid is extracted from a specimen and the extracted nucleic acid is amplified to be assayed, as a first support, a support to which a substance having affinity to the target nucleic acid is immobilized can be used to extract the target nucleic acid from the specimen, and as a second support, a support to which a reagent for detecting the target nucleic acid is immobilized can be used to assay the target nucleic acid. In this assay system, before the step of detecting the target nucleic acid in the specimen, the step of extracting the nucleic acid using the first support is carried out. Moreover, the system of the present invention includes a step of preparing the second support to which a substance having affinity to a biologically-relevant substance and/or labeling the biologically-relevant substance is immobilized. In one embodiment of the present invention, the pretreatment including the step of extracting the nucleic acid using the first support and the step of preparing the second support is consistently carried out in one system. Hereinafter, the step of detecting the nucleic acid using the present invention will be described.

Figure 30:
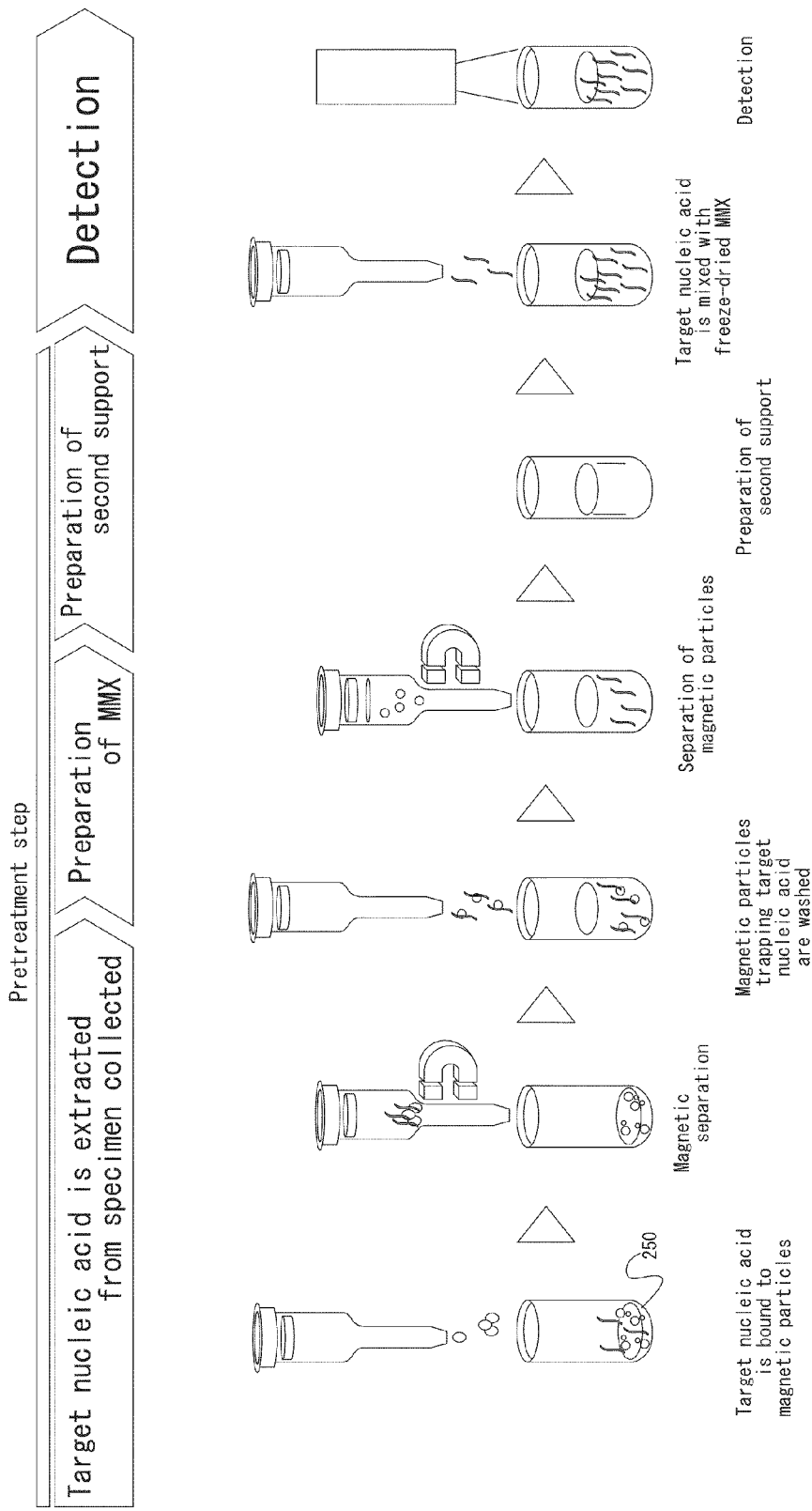
FIG. 30 is an explanatory drawing for schematically showing the pretreatment step from extraction of a nucleic acid from a specimen to preparation of a second support.

FIG. 30 is an explanatory drawing for schematically showing the pretreatment step from extraction of a nucleic acid from a specimen to preparation of a second support and the detection step. As shown in FIG. 30, in the system for assaying a target nucleic acid, (i) a step of extracting the target nucleic acid from the specimen using a support (first support) to which a substance having affinity to the target nucleic acid is immobilized, (ii) a step of preparing a support (second support) which has at least one of the function of having affinity to a biologically-relevant substance and the function of labeling the biologically-relevant substance, and (iii) a step of labeling and detecting the target nucleic acid using the prepared second support are carried out, and preferably the pretreatments (i) to (iii) are consistently carried out. The specimen is held in a well 250 provided to the assay system by a user.

6-1. Step of Extracting Target Nucleic Acid from Specimen

In order to obtain the target nucleic acid, a pipette chip (also referred to as "dispensing chip") having magnetic particles as the first support to which a probe for trapping the nucleic acid is immobilized (hereinafter referred to as "magnetic particles for trapping nucleic acid") is fitted to a nozzle. The specimen held in the well is sucked up into the pipette chip and mixed with the magnetic particles for trapping nucleic acid. After mixing, the target nucleic acid specifically binds to the probe immobilized to the magnetic particles for trapping nucleic acid and is trapped by the magnetic particles for trapping nucleic acid.

A magnet is moved toward the pipette chip with the magnetic particles for trapping nucleic acid to which the target nucleic acid binds being sucked up into the pipette chip, and the magnetic particles for trapping nucleic acid are constrained in the pipette chip. The pipette chip in which the magnetic particles for trapping nucleic acid are constrained by the magnet is moved away from the well and moved to a well holding a washing solution, and the magnet is moved away, thereby releasing the magnetic particles for trapping nucleic acid into the washing solution. The magnetic particles for trapping nucleic acid are washed with the washing solution, and after that, a reagent or the like is added thereto to separate the target nucleic acid from the magnetic particles, thereby obtaining the target nucleic acid.

6-2. Step of Preparing Support for Detecting Target Nucleic Acid Obtained

Meanwhile, in order to detect the extracted target nucleic acid, a support to which a substance having affinity to a biologically-relevant substance and labeling the biologically-relevant substance is immobilized is prepared. In the detection of the target nucleic acid, the target nucleic acid is labeled and amplified. As a labeling method and an amplification method, a publicly-known method such as PCR method, PT-PCR method, real-time PCR method, LAMP method, RT-LAMP method, ICAN method, SDA method, RCA method and NASBA method can be used. There are various techniques for performing the real-time PCR method, and for example, an intercalation method, a hybridization method, a LUX method or the like can be used.

For labeling and amplifying the nucleic acid, a solid-phased master mixture (MMX) containing a probe or primer for labeling and amplifying the nucleic acid can be used. When using the real-time PCR method, it is preferred that a primer or probe for amplifying the nucleic acid is suitably selected depending on the type of the nucleic acid to be amplified. As a probe or primer, for example, various products such as a TaqMan (registered trademark) probe, a FRET probe and a LUX primer can be used. The probe has a label for labeling the target nucleic acid. This probe having the label is allowed to hybridize to the target nucleic acid, thereby labeling the target nucleic acid. The primer and probe can be suitably designed depending on the type of the nucleic acid targeted for the detection. For example, when the hybridization method is used as the real-time PCR method, the target nucleic acid is subjected to thermal denaturation, annealing and elongation reaction to label the target nucleic acid.

In the present invention, before carrying out the detection of the target nucleic acid, a reagent to be used for amplification of the nucleic acid is prepared in advance, and the reagent is solid-phased and held in a well. In this way, a well (second support) to which a reagent that has been solid-phased (hereinafter referred to as "solid-phased reagent") is immobilized is prepared. At the time of amplification of the nucleic acid, a buffer solution, the nucleic acid, etc. are provided to the solid-phased reagent, and then labeling and amplification of the target nucleic acid is started. By using a large volume of master mixture, at the time of the assay step, it is possible to dispense it into wells for holding an assay sample, and work efficiency can be improved. The method for solid-phasing the reagent is not particularly limited, but when the reagent is freeze-dried, convenience is improved, and improvement of work efficiency can be expected.

When the reagent of the master mixture is freeze-dried, for example, the primer and probe for amplifying the target nucleic acid, and a protecting/stabilizing agent such as saccharide and polyvinylpyrrolidone for protecting and stabilizing the primer and probe are mixed together, and the mixture is cooled at a predetermined temperature and the pressure is reduced. The pressure at the time of preparation, cooling temperature and cooling time may be suitably changed depending on the property of the master mixture of interest. Further, in the present invention, it is preferred that sucrose, lactose, trehalose or the like is mixed so that a freeze-dried product is immobilized to the inside of a container as a solid phase (as the second support) when freeze-dried. In this way, for example, a freeze-dried reagent can be immobilized to the inside wall of a container, providing a film-like layer.

6-3. Step of Detecting Target Nucleic Acid

The detection of the target nucleic acid is carried out by putting the target nucleic acid into a well having the solid-phased reagent. After putting the target nucleic acid into the well, the target nucleic acid hybridizes to the probe contained in the solid-phased reagent, and then the detection becomes possible. For example, by measuring luminescence, fluorescence or the like, the target nucleic acid can be detected. The image data of the target nucleic acid can be obtained by using, for example, a fluorescence laser microscope having an image sensor as a detection device. Fluorescence intensity, etc. can be calculated by suitably analyzing the image data. By calculating the fluorescence intensity in this way, the target nucleic acid can be detected.

Next, a system for automatically carrying out each of the above-described steps will be described. An assay system for automatically carrying out the above-described procedure has an assay sample-obtaining apparatus for holding a specimen and obtaining a target nucleic acid and a detection apparatus for amplifying and detecting the obtained assay sample using the PCR method or the like.

The assay sample-obtaining apparatus has, for example, a well for holding a specimen and a well for holding a reagent. In the well for holding a specimen, a specimen obtained by a user such as a tissue, a cell and a body fluid is held. When the specimen is a tissue or a cell fragment, it is preferably minced in advance.

The well for holding a reagent has: a plurality of wells; a pipette chip; a reagent for dissolving the specimen; magnetic particles, which are put into the dissolved specimen, and to which a probe specifically binding to a target nucleic acid is immobilized; a magnet for constraining the magnetic particles in the pipette chip; an eluting reagent for separating and eluting the target nucleic acid from the magnetic particles which specifically bind to the nucleic acid via the probe; etc. The target nucleic acid such as a DNA and an RNA is extracted from the specimen held in the well for holding a specimen.

The well for holding a reagent further has a well for holding a solid-phased reagent for labeling and amplifying the target nucleic acid extracted from the specimen. In the well, for example, a buffer, a primer, a probe, nucleic acid polymerase, a distilled water, a washing solution and the like are solid-phased and held. The solid-phased reagent can be prepared, for example, by mixing respective reagents together and freeze-drying the mixture (freeze-dried master mixture).

The target nucleic acid can be extracted as follows: the specimen is dissolved, and the obtained solution is mixed with the magnetic particles to which the probe specifically binding to the target nucleic acid is immobilized; after mixing, the magnet is used to constrain and separate the target nucleic acid-bound magnetic particles in the pipette chip; and the separated magnetic particles are washed, followed by eluting the target nucleic acid.

The detection apparatus carries out the action of amplifying and detecting the target nucleic acid extracted from the specimen. As the technique of amplifying the nucleic acid, a real-time PCR method is exemplified. Amplification of the target nucleic acid can be carried out using the freeze-dried master mixture held in the well for holding a reagent according to the real-time PCR method. The detection apparatus has a reaction container for nucleic acid amplification, a temperature adjustment portion for adjusting the temperature of the reaction container, etc., and respective steps of thermal denaturation, annealing and elongation reaction of the nucleic acid can be repeatedly carried out. After amplification of the target nucleic acid, the labeled target nucleic acid is irradiated, for example, with an electromagnetic wave for excitation, or a substrate solution for fluorescence reaction is added and then the target nucleic acid is scanned by a scanner or the like, thereby detecting the target nucleic acid.

Figure 31:
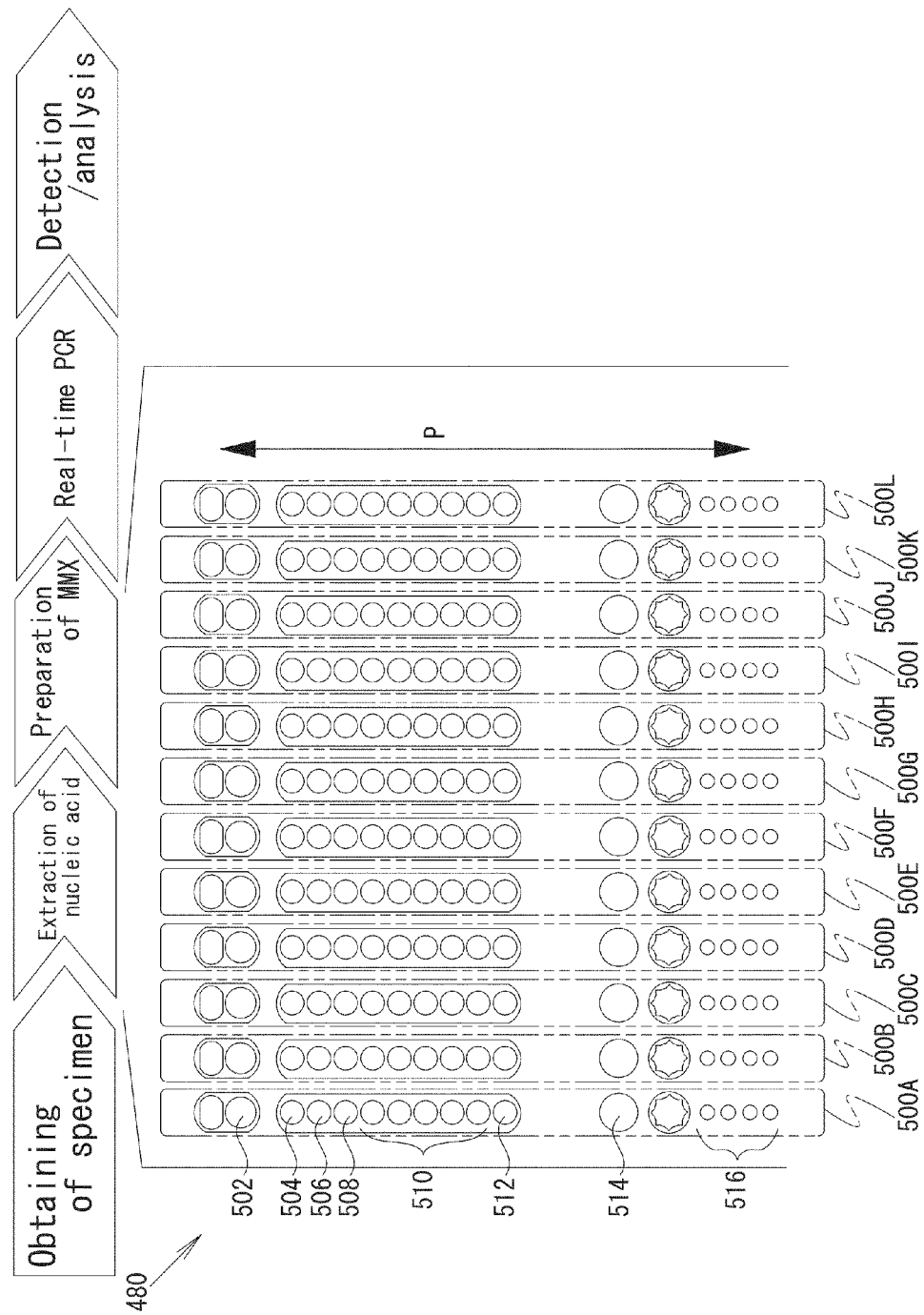
FIG. 31 is an explanatory drawing for schematically explaining a treatment portion in which 12 lines of a plurality of wells are arranged in lines.

Hereinafter, a more specific example of the above-described system will be described. FIG. 31 is a top view of wells for carrying out from extraction to detection of the target nucleic acid. As shown in FIG. 31, the assay system 480 for the target nucleic acid has treatment lines. FIG. 31 exemplifies 12 treatment lines from a first treatment line 500A to a twelfth treatment line 500L. In the respective treatment lines 500A to 500L, for example, a well 502 for holding a specimen; a well 504 for holding a dissolving solution; a well 506 for holding a buffer solution; a well 508 for holding magnetic particles; wells 510 for holding a washing solution for washing the nucleic acid extracted from the specimen and a washing solution for washing a pipette chip; a well 512 for holding an eluting solution for separating the target nucleic acid from the magnetic particles; a well 514 for temporarily holding an assay sample in which the nucleic acid has been extracted from the specimen; and wells 516 for holding a solid-phased master mixture for labeling the assay sample and detecting the target nucleic acid are arranged.

Above the first to twelfth treatment lines 500A to 500L, 12 nozzles corresponding to the respective treatment lines 500A to 500L are movably provided in the line direction P (not shown), and to each nozzle, a pipette chip is suitably fitted. The assay system 480 has, for example, a shielding door for isolating a well-arranged space from the outside, and the wells provided to the first to twelfth treatment lines can be shielded from the outside by this shielding door. In the explanation above, the apparatus having the 12 treatment lines is exemplified, but the number of treatment lines is not limited thereto. For example, the number of treatment lines may be 1 or 2, or 20 or 30 in order to increase processing ability.

Figure 32:
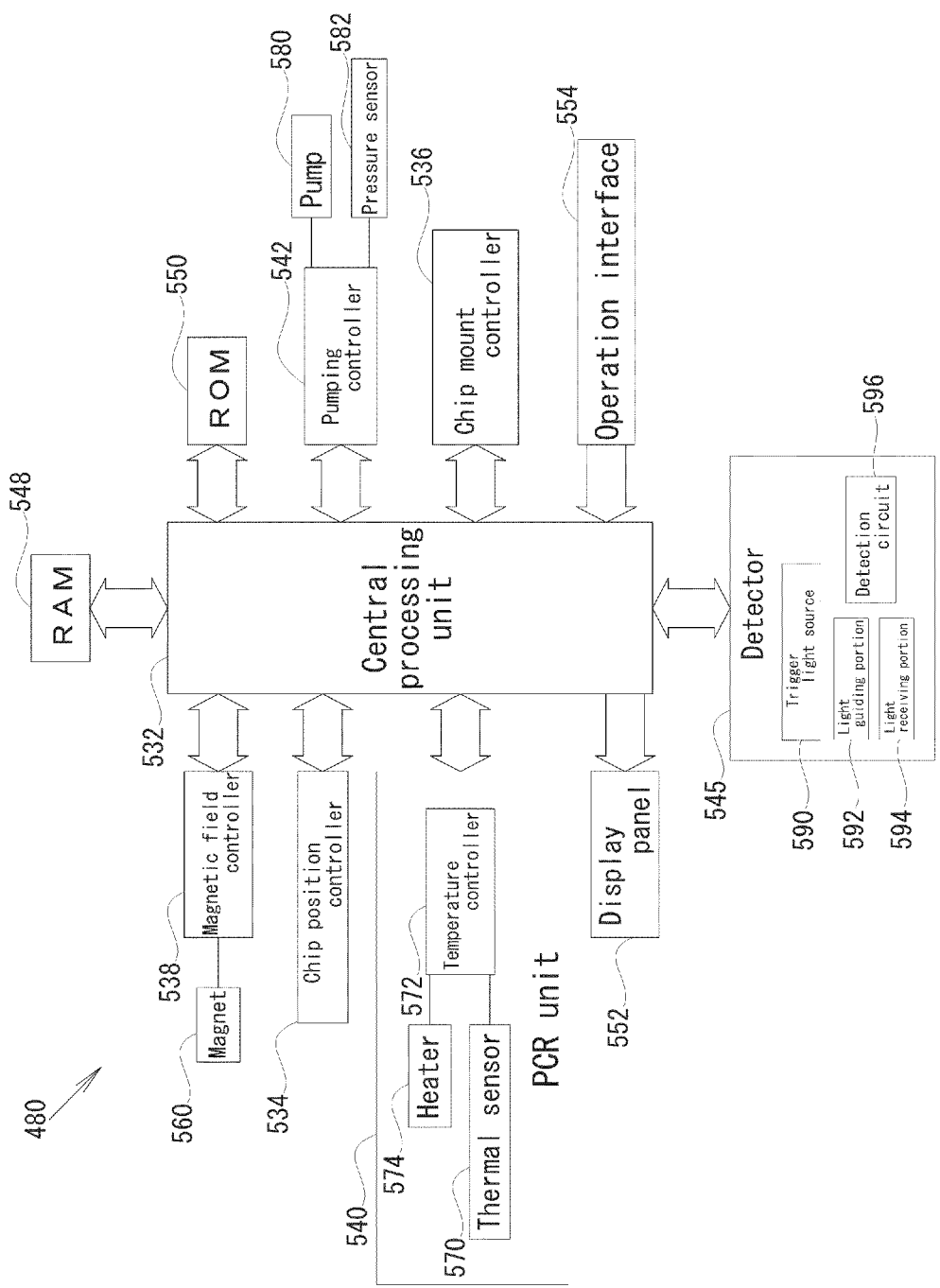
FIG. 32 is a block diagram showing the functions of the assay system.

As shown in FIG. 32, the assay system 480 has a central processing unit 532, a chip position controller 534, a chip mount controller 536, a magnetic field controller 538, a PCR unit 540, a pumping controller 542, a detector 545, a RAM 548, a ROM 550, a display panel 552, an operation interface 554, a timer, etc.

The chip position controller 534 has mutually orthogonal axes X, Y and Z, and the position of the nozzle is controlled by a stepping motor or a servomotor. Regarding the axes X, Y and Z, for example, the axis X is approximately parallel to the well arrangement direction of the treatment lines, the axis Y is approximately perpendicular to the axis X and approximately parallel to the direction of traversing the lines, and the axis Z is approximately perpendicular to a plane made by the axis X and the axis Y. When the treatment of the specimen is started and each nozzle is moved, for example, the nozzle is driven in two steps, i.e., a movement on the axis X and a movement on the axis Z, thereby carrying out the treatments along the respective treatment lines 500A to 500L.

The chip mount controller 536 performs attachment of the pipette chip to the nozzle and detachment of the pipette chip from the nozzle. The chip mount controller 536 has a gripping portion for gripping the pipette chip and a chip preparation portion for preparing another new pipette chip. When the nozzle is moved upward along the axis Z with the pipette chip being gripped by the gripping portion, the pipette chip is detached from the nozzle. Next, the bared nozzle is moved on the axes X and Y to move to a position above a new pipette chip. At the chip preparation portion, the new pipette chip is held with a mount portion side up and a tip portion side down. When the nozzle is moved downward along the axis Z, the mount portion of the new pipette chip is attached to the nozzle.

The pumping controller 542 has a pump 580 and a pressure sensor 582, and controls sucking up and discharging of the liquid performed via the nozzle and the pipette chip attached to the nozzle. The pump 580 has a housing formed into a cylindrical shape, a piston that is movably fitted into the housing and a motor for driving the piston. The inside of the housing communicates with the opening of the nozzle. The movement of the piston is controlled, for example, by a servomotor, and driving of the servomotor is controlled by a drive control signal from the pumping controller 542. When the piston is activated, it becomes possible to suck up or discharge the liquid through the opening of the nozzle.

In the opening of the nozzle, a pressure sensor 582 for detecting the pressure is provided, and the pressure sensor 582 transmits a pressure signal to the pumping controller 542. The pumping controller 542 monitors the pressure based on the pressure signal from the pressure sensor 582. In this constitution, for example, when the tip portion of the pipette chip is immersed in the specimen in the well, the pressure detected by the pumping controller 542 exceeds a predetermined threshold, and in response to this, the drive control signal is transmitted to the servomotor. Also at the time of sucking up and discharging a fluid, the pressure sensor 582 constantly transmits the pressure signal to the pumping controller 542. Therefore, the pumping controller 542 can control driving of the servomotor with high accuracy. In this constitution, the nozzle to which the pipette chip is attached can carry out sucking up and discharging the fluid, and the fluid can be stirred thereby.

In the ROM 550, various control programs are stored. According to a mode selected by a user via the operation interface 554, a control program read from the ROM 550 is developed to the RAM 548, and the central processing unit 532 controls each portion of the assay system 480 based on the control program developed in the RAM 548.

Examples of treatment programs to be stored in the ROM 550 include: (1) a first program for extracting an RNA from a cell or virus and detecting a PCR product after a PCR reaction; (2) a second program for extracting a DNA from a biological sample such as blood and detecting a PCR product after a PCR reaction; and (3) a third program for extracting a plasmid DNA from a bacterium such as *E. coli*.

The display panel 552 displays items required to be provided to the user. For example, the display panel 552 can display the number of times of pumping at the time of extraction of nucleic acid, time to be allowed to stand after suspension of the magnetic particles, the flow rate at the time of pumping, the amount to be sucked up and discharged, the rate of movement of the pipette chip, etc., and the user can confirm these items by the display. When set contents are desired to be changed, they can be changed by operation of the operation interface 554.

The timer carries out timing according to a program read from the ROM 550. Timing is carried out, for example, when pumping or thermal denaturation, annealing and elongation reaction in a PCR reaction are performed. By timing, a period of carrying out each step is accurately managed.

The magnetic field controller 538 manages the placement of the magnet 560 to control the strength of the magnetic field provided to the pipette chip. The magnetic field controller 538 has mutually orthogonal axes X, Y and Z, and the placement of the magnet 560 is determined by a stepping motor or a servomotor. The axes X and Y are approximately parallel to a plane in which wells are arranged and mutually orthogonal, and the axis Z is approximately perpendicular to the plane. At the time of the movement of the magnet 560, for example, the placement of the magnet 560 can be determined in two steps, i.e., a movement on the axes X and Y and a movement on the axis Z.

The PCR unit 540 has a thermal sensor 570, a temperature controller 572 and a heater 574. The temperature controller 572 detects a temperature based on a temperature signal from the thermal sensor 570. The thermal sensor 570 is located, for example, adjacent to a well 516 holding a master mixture, and transmits the temperature signal to the temperature controller depending on the temperature of the fluid in the well. The heater 574 is located adjacent to the well 516, and energization of the heater 574 is controlled by the temperature controller 572. The temperature controller 572 controls energization of the heater 574 based on the temperature signal from the thermal sensor 570, thereby controlling the temperature of the fluid in the well 516. In this way, a PCR reaction, which requires appropriate temperature control, can be rapidly carried out. The cycle of PCR reaction is basically constituted by repeat of a thermal denaturation step, an annealing step and an elongation reaction step, and the temperature controller 572 controls the temperature of the fluid using the heater 574 so that the temperature becomes optimum in each step. The data regarding the optimum temperature, reaction time and the number of cycles of reaction in PCR reaction are stored in ROM in advance and read and carried out in response to a treatment mode selected by the user.

The detector 545 has: a trigger light source 590; a light guiding portion 592 for sending a trigger light from the trigger light source to the liquid in the well; a light receiving portion 594 for receiving light from the nucleic acid fluorescing due to light sent from the light guiding portion 592; a detection circuit 596; etc. The light guiding portion 592 can be constituted, for example, by using optical fibers, and can guide the trigger light from the trigger light source in the optical fibers to send the trigger light to the liquid in the well. For the light receiving portion 594, for example, image sensors such as CCD and MOS can be used, and the light receiving portion 594 receives light from the fluorescing nucleic acid to output a light receiving signal to the detection circuit 596. The detection circuit 596 detects the nucleic acid based on the light receiving signal from the light receiving portion 594.

Figure 33:
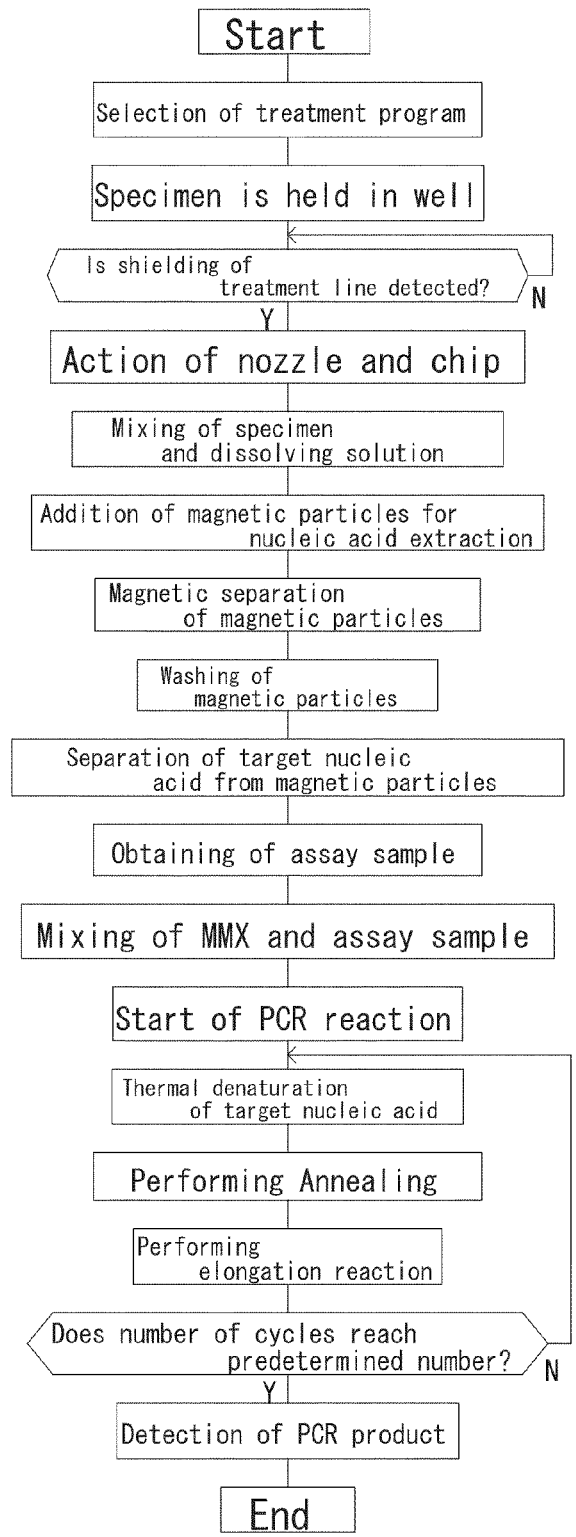
FIG. 33 is a flow chart showing the treatment process carried out by the assay system.

The action of the nucleic acid detection system of the present invention will be described using a flow chart of FIG. 33. The treatment program selected by the user is read from the ROM 550, and based on the read treatment program, the action of each portion of the assay system 480 is started. By the user, the obtained specimen is manually put into the well 502 of each treatment line (the first to twelfth treatment lines 500A to 500L in FIG. 31), and by the shielding door, the first to twelfth treatment lines 500A to 500L are shielded from the outside. After shielding of the first to twelfth treatment lines 500A to 500L is detected, the treatment of the specimen is started, and the 12 nozzles and pipette chips provided corresponding to the first to twelfth treatment lines 500A to 500L are driven, thereby mixing the specimen with the dissolving solution. After stirring of the mixture, the magnetic particles are added to the mixture, followed by stirring.

After the mixture to which the magnetic particles have been added is sufficiently stirred, using the magnet, the magnetic particles are constrained in the pipette chip to discharge unnecessary liquid to the outside of the pipette, thereby obtaining the magnetic particles to which the target nucleic acid has bound. The obtained magnetic particles are discharged into the well holding the washing solution and washed. After washing, the magnetic particles are mixed with a separating solution for breaking the bond with the target nucleic acid and the mixture is stirred. After the separating solution to which the magnetic particles have been added is sufficiently stirred, the magnetic particles are constrained in the pipette chip to separate the target nucleic acid. The obtained fluid containing the target nucleic acid, as the assay sample to be provided to the assay step, is held in the well 514. The assay sample held in the well 514 is dispensed into the well 516 in which the master mixture is held in advance to perform PCR reaction. In the PCR reaction step, the thermal denaturation step, the annealing step and the elongation reaction step are repeated a predetermined number of times to produce the PCR product based on the target nucleic acid. After carried out a predetermined number of times, the PCR product is detected by the detector 545.

Thus, by providing the 12 treatment lines typified by the first to twelfth treatment lines 500A to 500L, 12 specimens can be can be simultaneously treated, and therefore the efficiency of the treatment of specimen can be improved. Further, by arranging the well 502 for holding the specimen, the well holding the magnetic particles for target nucleic acid extraction, the well for washing and the well holding the master mixture in a line, the nozzle and the pipette chip can be driven without loss, and treatment time can be further shortened. Moreover, since the nozzle and the pipette chip are driven in a linear fashion, mixing of the specimen of another line can be prevented, and contamination can be reduced.

In the explanation above, the assay system having the 12 treatment lines is exemplified, but the number of treatment lines is not limited thereto, and the number may be more or less than that. Further, in the embodiment above, the assay system having the 12 treatment lines is exemplified, but other than the treatment in a linear fashion, for example, a block for holding the specimen, a block for reacting the specimen with the magnetic particles, a block for holding the washing solution for washing the magnetic particles, etc., a block for holding the prepared assay sample, a block for PCR reaction, a block for assaying the amplified target nucleic acid and the like may be arranged in a circular pattern or in a cross shape.

Figure 34:
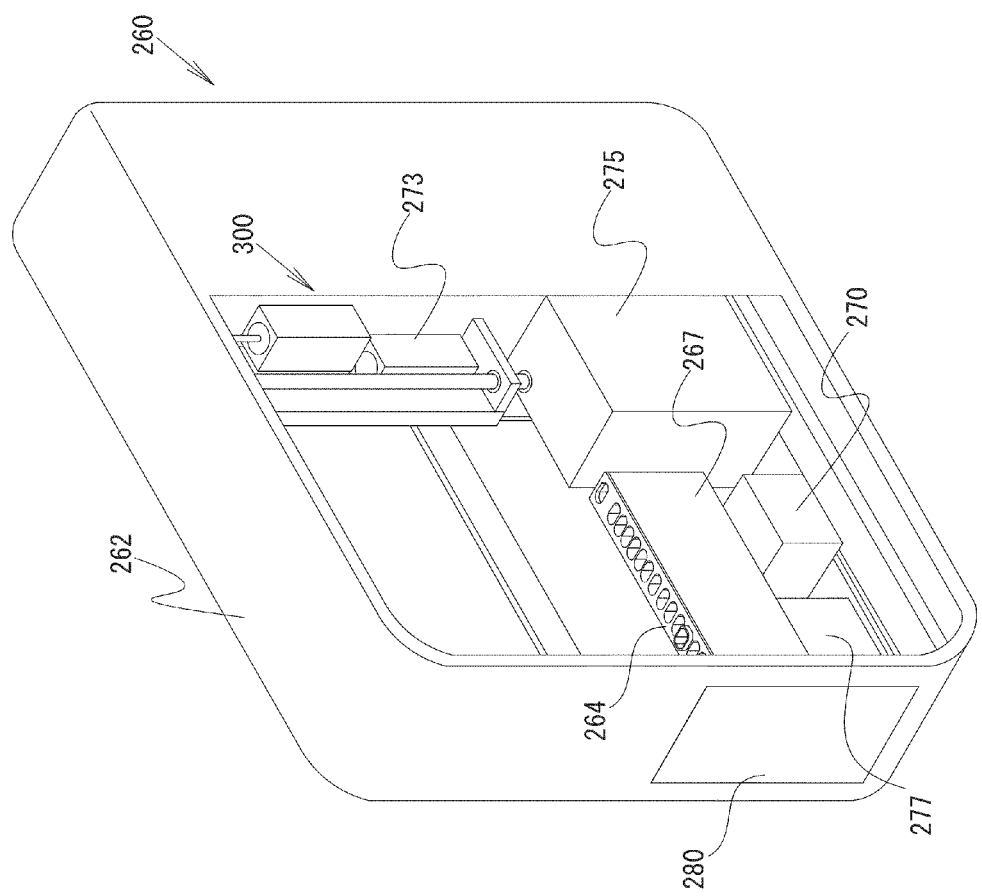
FIG. 34 is a schematic view of an assay system in which a nucleic acid can be pretreated utilizing a cartridge.

Further, the embodiment of the system is not limited to that described above and can be suitably changed. FIG. 34 is a schematic view of an assay system in which a nucleic acid can be pretreated utilizing a cartridge. For example, as shown in FIG. 34, a target nucleic acid can be detected using a cartridge in which a specimen holding portion and a reagent holding portion are integrated. Hereinafter, the system for treating the specimen using the cartridge in which the specimen holding portion and the reagent holding portion are integrated will be described.

An assay system 260 has a system body 262 and a cartridge 264 to be loaded on the system body 262. The system body 262 has: a rack 267 for holding the cartridge 264; a movement control mechanism 270 for controlling the movement of the rack 267 between the drawn position at which the rack is drawn out from the system body 262 and the housed position at which the rack is housed in the system body; a pipette chip having the magnetic particles for obtaining the nucleic acid; a placement control mechanism 273 for controlling the placement of the pipette chip relative to the cartridge 264; a chip attachment/detachment controller 275 for attaching or detaching the pipette chip; a scanner 277 for scanning and detecting the amplified nucleic acid; etc. The rack 267 has a lid 280 for shielding the cartridge 264 positioned at the housed position from the outside, and this reduces the risk of adherence of bacteria to the cartridge 264 positioned at the housed position, etc.

Figure 35:
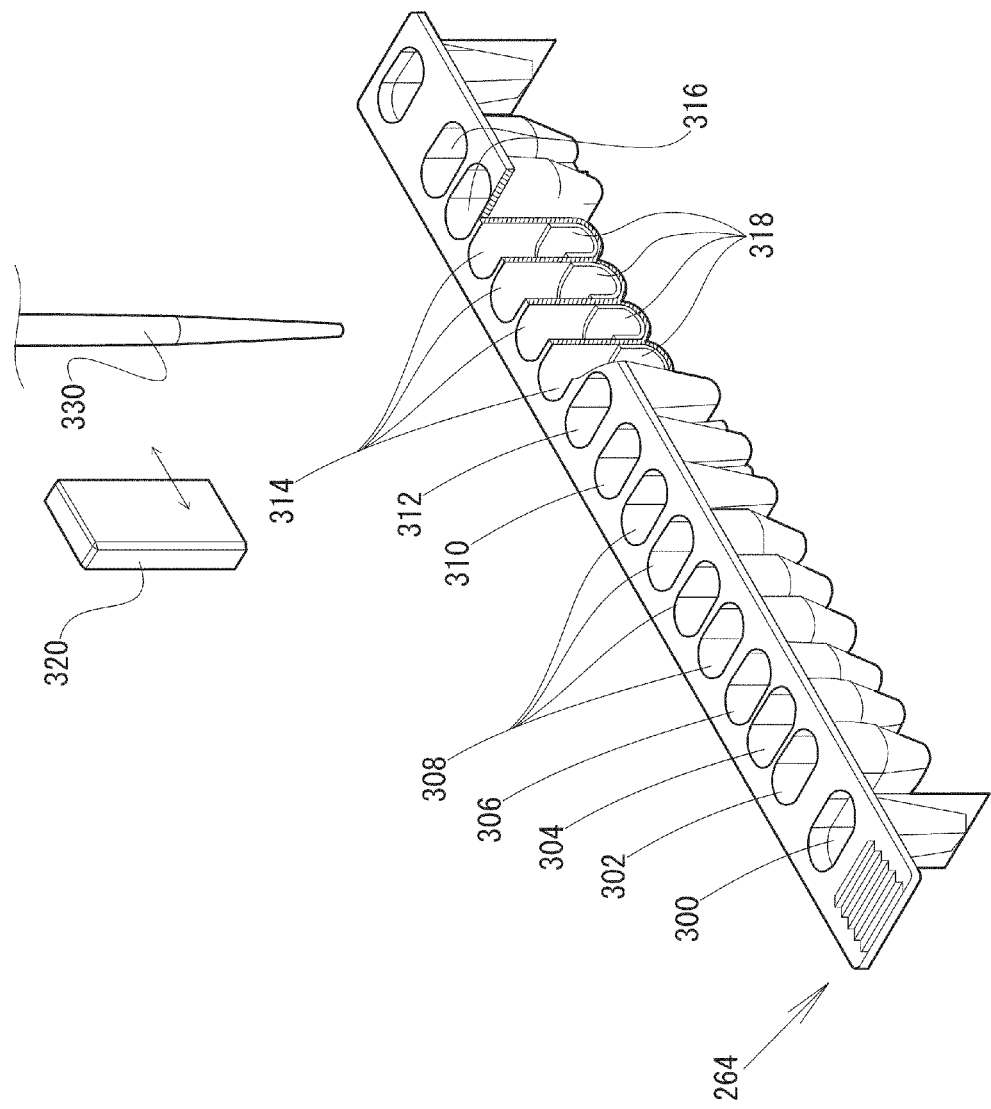
FIG. 35 is a perspective cross portional view of a cartridge in which wells holding a master mixture are partially taken along the longitudinal direction of the cartridge.

Regarding the arrangement form of wells of the cartridge 264, the number, order, size, etc. of wells vary depending on whether a DNA or a RNA is extracted for amplification. FIG. 35 shows a cartridge to be used in the above-described assay system, and is a perspective cross sectional view of wells holding the master mixture, a portion of which is taken along the longitudinal direction of the cartridge. For example, in the case where a DNA is extracted and amplified using the PCR method, as shown in FIG. 35, into the cartridge 264, a well 300 for holding the specimen; a well 302 in which an extraction reagent for extracting DNA from the specimen is held in advance; a well 304 for holding a buffer; wells 306 and 308 for holding a washing solution for washing the extracted DNA; an eluting solution 310 for separating the DNA from the magnetic particles for target nucleic acid extraction to obtain the DNA; a well 312 for holding a washing solution for washing a pipette chip 330; wells 314 for holding a freeze-dried master mixture; wells 316 for holding a substrate solution used when allowing the labeled DNA to fluoresce to be detected; etc. are integrated. The opening of each well is sealed with an aluminum seal (not shown) so that bacteria do not invade the inside of each well prior to use. In the wells 314, a freeze-dried master mixture 318 is provided to the inside wall of the container, providing a film-like layer. As a technique of providing the freeze-dried master mixture 318 in the film-like form in the wells 314, for example, a master mixture before freeze-dried is held in the wells 314, and after that, freeze-drying is carried out under predetermined freeze-drying conditions, thereby providing the film-like freeze-dried master mixture 318 in the wells 314.

After the cartridge 264 is loaded on the rack 267 and automatic detection of nucleic acid is started, the rack 267 is housed in the system body 262, and the cartridge 264 is isolated from the outside. After the cartridge 264 is positioned at the housed position by the rack 267, the aluminum seal is detached, and extraction of DNA from the specimen is carried out. To the cartridge 264, the wells 314 having the freeze-dried master mixture are provided in advance, and therefore, after the extraction of DNA, the pretreatment can be rapidly finished, and it is possible to shift to the next assay step.

Thus, since it is possible to automatically and consistently carry out the pretreatment using the cartridge 264, in the present invention, a simple and convenient system can be provided. Further, by extracting the target nucleic acid from the specimen using the magnetic particles, the amount of unnecessary substances is reduced before amplification of the nucleic acid, thereby carrying out more reliable DNA detection.

Figure 36:
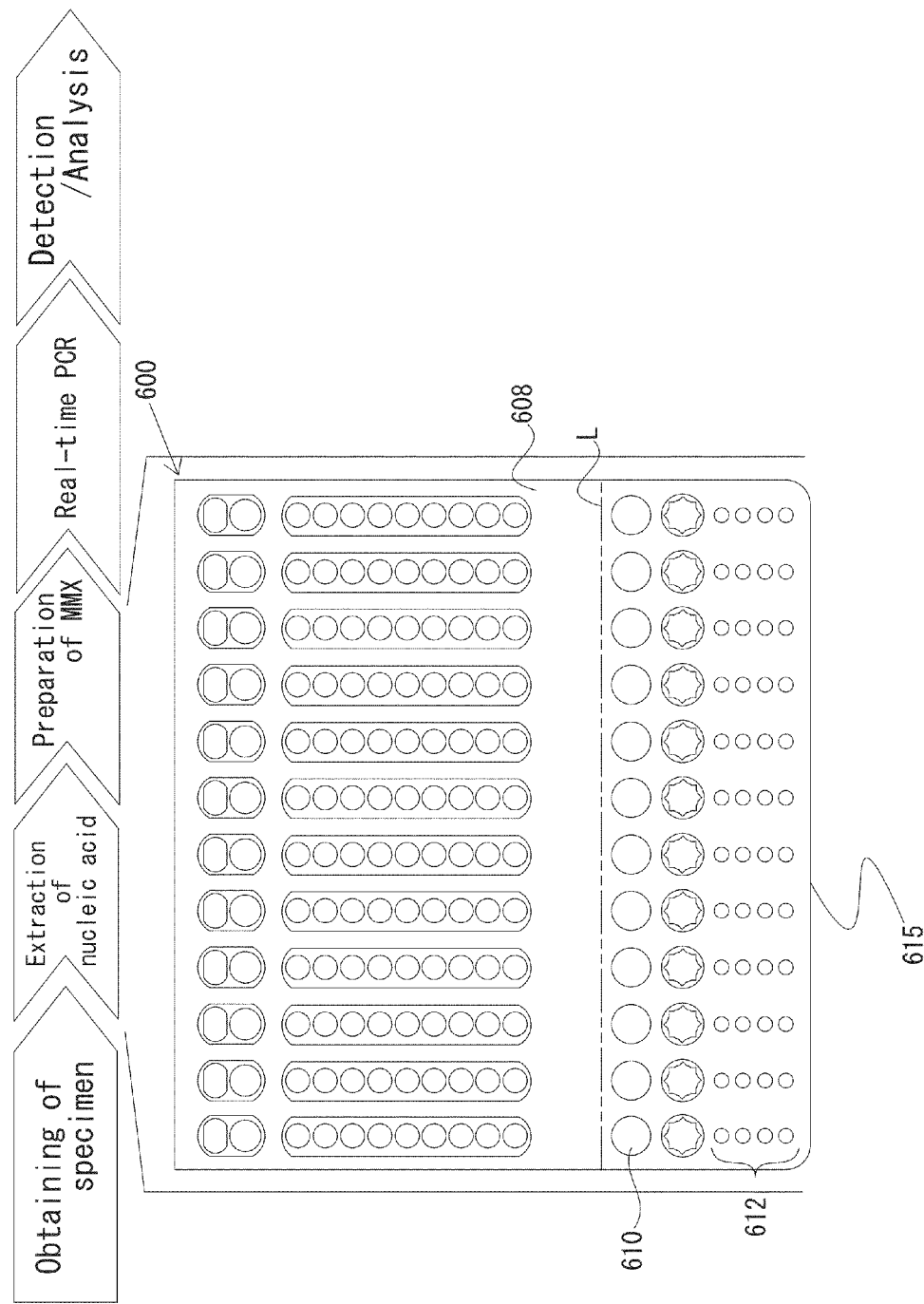
FIG. 36 is an explanatory drawing for explaining an embodiment in which wells holding an assay sample and wells holding a master mixture are separated from a cartridge body.

Further, in the explanation above, the steps from the step of extracting the target nucleic acid from the specimen to prepare the assay sample to the step of detecting the target nucleic acid based on the prepared assay sample are consistently carried out, but it is also possible to independently carry out the step of extracting the target nucleic acid from the specimen to prepare the assay sample and the assay step of assaying the target nucleic acid based on the assay sample using different apparatuses. As one example of such a system, an assay system, which has: a sample preparation apparatus, wherein the specimen is held, the target nucleic acid is extracted and the assay sample is obtained; and a detection apparatus, wherein the obtained assay sample is amplified using the nucleic acid amplification method and detection is carried out, is exemplified. When using such a system, as shown in FIG. 36, in a well cartridge 600, a separation unit 615 into which a well 610 for holding the assay sample and the wells 612 for holding the master mixture are integrated can be split and separated from a cartridge body 608, for example, along the splitting line L, and the separation unit 615 is loaded on the detection apparatus, thereby carrying out the detection of the target nucleic acid.

When the obtained specimen is held in the well cartridge 600 and it is loaded on a sample preparation apparatus, the treatment of the specimen is started, and the assay sample is held in the well 610 for holding the assay sample. When the separation unit 615 is separated from the cartridge body 608 and loaded on the detection apparatus, the assay sample held in the well 610 is poured into the 4 continuous wells 612 holding the master mixture. After the assay sample is mixed with the master mixture, the target nucleic acid is amplified according to the PCR method and then detected.

Thus, since the separation unit 615 into which the well 610 for holding the assay sample and the wells 612 for holding the master mixture are integrated can be separated from the cartridge body 608, the step until obtaining the assay sample and the step of detecting the target nucleic acid from the obtained assay sample can be respectively carried out in different apparatuses.

Therefore, the drive schedule of the sample preparation apparatus is independent from the drive schedule of the detection apparatus. Accordingly, after preparation of a first assay sample, preparation of a second assay sample can be immediately started, and therefore, the assay sample can be prepared more freely without the necessity of waiting the detection of the target nucleic acid. In addition, it is possible to temporarily store the assay sample.

Figure 37:
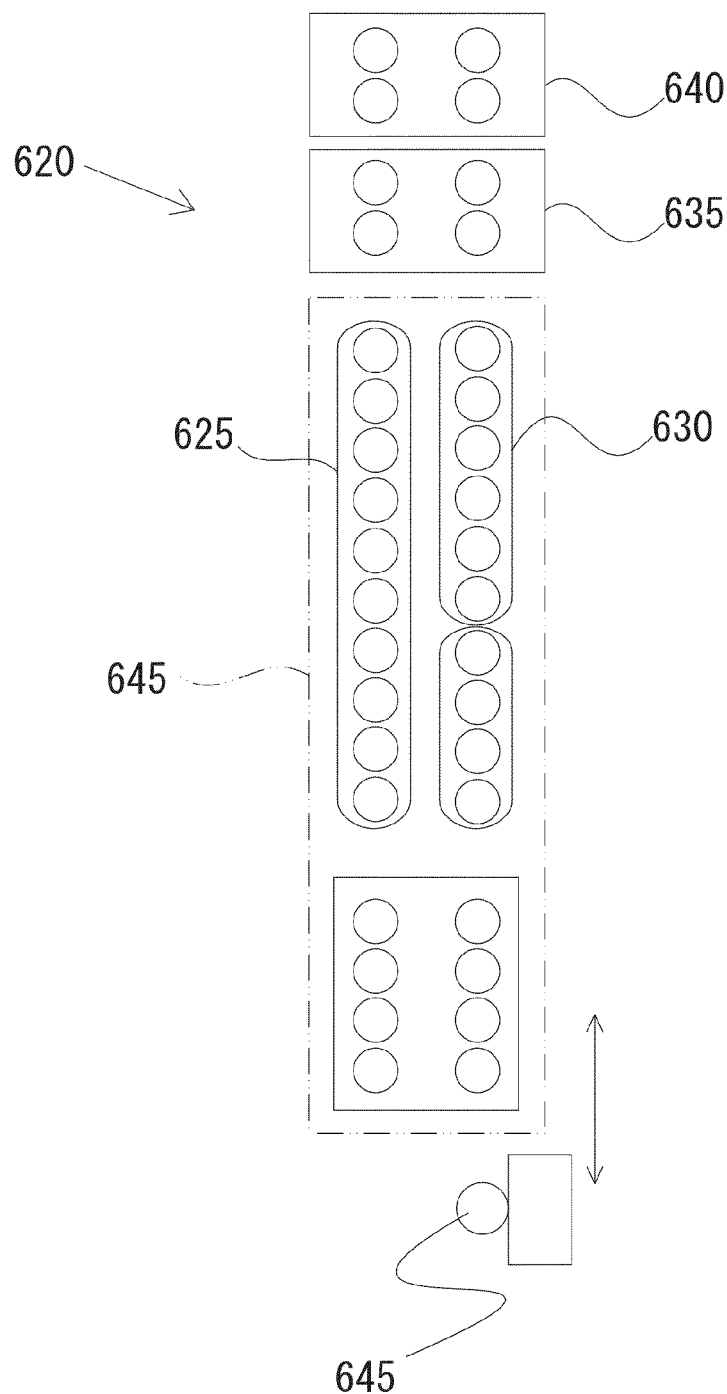
FIG. 37 is an explanatory drawing for explaining an embodiment in which detection of a nucleic acid is carried out using a plurality of wells arranged in a line.

Further, in the explanation above, one specimen corresponds to one line of the group of wells, but one specimen may also correspond to a plurality of lines of the group of wells. For example, as shown in FIG. 37, one specimen can correspond to two lines of wells. An assay system 620 has: a nucleic acid extraction portion 625 having wells to be used at the time of extraction of nucleic acid; a solid-phased reagent holding portion 630 having wells holding a solid-phased reagent for nucleic acid amplification; a temperature adjustment portion 635 which is combined with a thermal cycler; a detector 640 for sending a trigger light and detecting a nucleic acid; a nozzle unit 645; etc. The nozzle unit 645 is driven within a work area 645 and carries out sucking up and discharging the specimen. The nucleic acid may be assayed using the arrangement of wells in this way.

Further, in a preferred embodiment of the present invention, using the assay system described above, various viruses such as influenza viruses (e.g., H1N1, H3N2, H5N1, H7N7) can be detected. The detection of influenza virus is carried out in the following order: extraction of an influenza virus from a specimen collected (e.g., body fluid in the nasal cavity); preparation of a master mixture; performing real-time RT-PCR; and detection.

[Probe and Primer for Detection of Influenza Virus a (H1N1)]
Examples of probes and primers to be used include:
Forward primers (InfA, SW InfA, SW H1, RnaseP)
Reverse primers (InfA, SW InfA, SW H1, RnaseP)
Taq Man probes (InfA, SW InfA, SW H1, RnaseP)

Therefore, combinations of a primer and a probe are as follows:
InfA: influenza A primer set and Taq Man probe
SW InfA: SW InfA primer set and Taq Man probe
SW H1: SW H1 primer set and Taq Man probe
RnaseP: human RNaseP gene (internal positive control) primer set and Taq Man probe Mater mixtures, which contain the above-described 4 types of combinations of a primer and a probe, respectively, are prepared, and for example, they are put in the 4 continuous wells 314 of the cartridge 264 shown in FIG. 35 in advance, and the wells are sealed with an aluminum seal. In this way, it is possible to provide a system by which influenza virus A (H1N1) can be detected by simple operation, and a cartridge for this system.

In the above-described example, the cartridge 264 carries out from the step of extraction of nucleic acid to the step prior to the detection regarding one specimen, but it is also possible to arrange a plurality of cartridges 264 in parallel to allow simultaneous treatment of a plurality of specimens. By treating a plurality of specimens simultaneously, it is possible to improve treatment capacity and to provide a more convenient system.

In FIGS. 31-37 described above, the embodiment using the PCR method in which nucleic acid amplification is performed by increasing/decreasing the temperature of a mixing solution of the target nucleic acid and the reagent for PCR reaction is exemplified, but the present invention is not limited thereto, and it is also possible to use an isothermal amplification method in which the nucleic acid is isothermally amplified.

The nucleic acid amplification apparatus of the present invention is characterized in that it comprises:
(a) a specimen holding portion in which a specimen is held;
(b) a first holding portion in which trapping particles for trapping a target nucleic acid from the specimen are held;
(c) a second holding portion in which a reagent for detecting the target nucleic acid is held;
(d) a dispensing mechanism for dispensing the specimen into the specimen holding portion, a mechanism for mixing the specimen with the trapping particles to extract the target nucleic acid from the specimen, and a mechanism for mixing the extracted target nucleic acid with the reagent for detecting; and
(e) a mechanism selected from the group consisting of: a mechanism for pouring a hydrophobic fluid, which has a specific gravity smaller than that of a mixed fluid of the target nucleic acid and the reagent for detecting, into the second holding portion; a mechanism for removing or putting lids for covering the respective holding portions; a mechanism for irradiating an irradiating light for letting the target nucleic acid fluoresce; a mechanism for receiving a light from the target nucleic acid irradiated with the irradiating light to detect the target nucleic acid; and a mechanism in which the mechanisms are combined.

By changing the combination of the constitutions of (a) to (e) above, various types of apparatus can be realized.

Hereinafter, an apparatus having a mechanism of isothermally amplifying a target nucleic acid will be described. Regarding the same points as those for the above-described apparatus for amplifying a target nucleic acid using the PCR method, the outline thereof will be described, and detailed description thereof is omitted.

Figure 38:
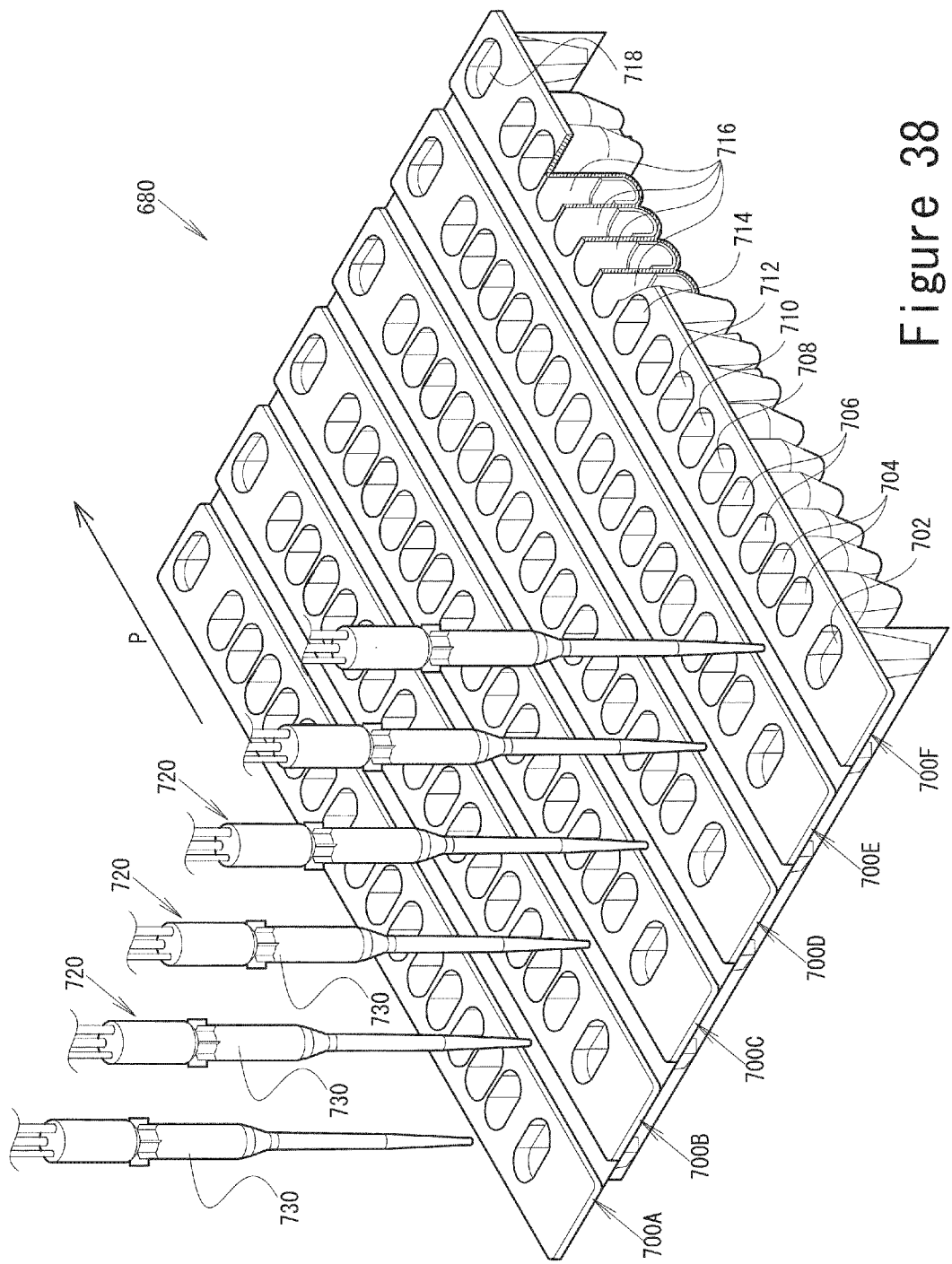
FIG. 38 is a perspective view showing a cartridge having a plurality of treatment lines in which wells are arranged and nozzle units which move on this cartridge along the treatment lines.

FIG. 38 is a perspective view showing a plurality of wells and nozzles for carrying out from extraction to detection of a target nucleic acid. As shown in FIG. 38, in each of treatment lines 700A to 700F integrated into a cartridge, for example, the following wells are arranged: a well 702 for holding a specimen; wells 704 for holding a dissolving solution; wells 706 for holding a buffer solution; a well 708 for holding magnetic particles as trapping particles; a well 710 for holding a washing solution for washing a nucleic acid extracted from the specimen or a washing solution for washing a pipette chip; a well 712 for holding an eluting solution containing a reagent for separating the target nucleic acid from the magnetic particles; a well 714 for temporality holding a target nucleic acid-containing solution obtained after extraction of nucleic acid from the specimen; wells 716 containing a dried reagent (e.g., freeze-dried reagent) for amplifying the target nucleic acid (reagent for detection); and a detection well 718 for detecting an amplified product obtained by amplifying the target nucleic acid in the target nucleic acid-containing solution.

Above the first to sixth treatment lines 700A to 700F, 6 nozzle units 720 corresponding to the respective treatment lines 700A to 700F are movably provided in the line direction P, and to each nozzle unit 720, a pipette chip 730 can be fitted. The number of treatment lines is not limited to 6 and can be suitably changed.

Figure 39:
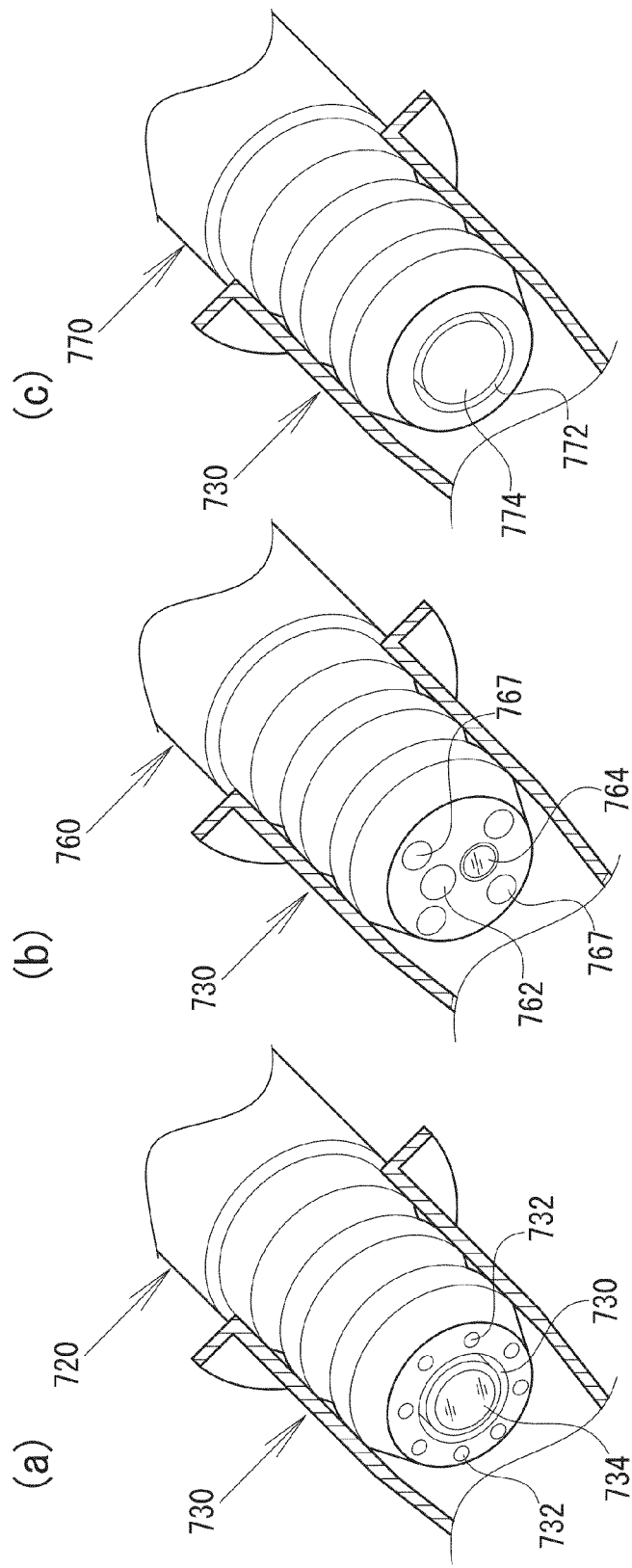
FIG. 39 is a perspective view of the tip portion of a nozzle unit having a pumping opening, an optical fiber for sending a trigger light and a lens for detection.

FIG. 39 is a partial perspective view showing the tip portion of the nozzle unit 720. As shown in FIG. 39(a), for example, the nozzle unit 720 has: a pumping opening 730 for sucking up/discharging a fluid such as a solution containing a specimen or target nucleic acid; a plastic optical fiber (hereinafter referred to as "POF") 732 for sending a trigger light for fluorescence reaction to an amplified product of the target nucleic acid; and a lens 734 for receiving a light from the target nucleic acid. The lens 734 is placed in the pumping opening 730, and around the pumping opening 730, for example, 8 POFs 732 are arranged at equally-spaced intervals. The form of the nozzle unit is not limited to the above-described one, and for example, nozzle units shown in FIGS. 39(b) and (c) may also be employed. As shown in FIG. 39(b), to the central portion of the tip of a nozzle unit 760, a pumping opening 762 for sucking up/discharging a fluid and a lens 764 are provided, and to the surrounding portion thereof, 4 POFs 767 for sending a trigger light are provided. Further, as shown in FIG. 39(c), it is also possible to employ a constitution in which a pumping opening 772 and a POF 774 for sending a trigger light are provided to the central portion of the tip portion of a nozzle unit 770.

Figure 40:
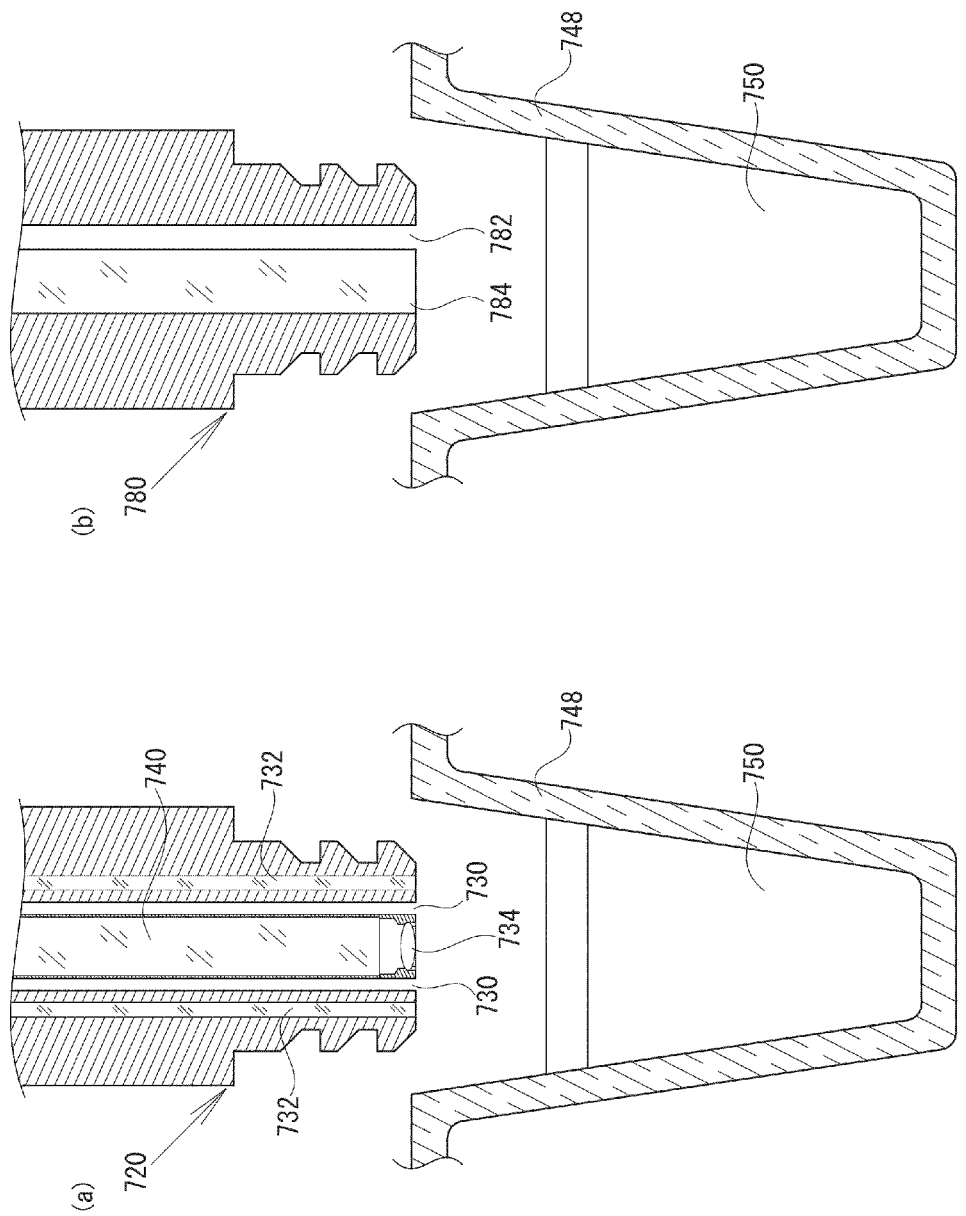
FIG. 40 is a cross portional view of the tip portion of a nozzle unit taken along a plane parallel to the drawing direction of an optical fiber.

FIG. 40 is a cross sectional view of a nozzle unit 720 taken along a plane parallel to the drawing direction of a pumping opening 730. As shown in FIG. 40, around the pumping opening 730, for example, 8 POFs are arranged, and in the center in the pumping opening 730, a lens 734 and a POF 740 for transmitting optical images are placed. The lens 740 is opposed to an amplified product-containing solution held in a well 748 for detection, and provides an optical image of the amplified product-containing solution to the POF 740 side. The optical image provided by the lens 740 is sent through the POF 740 and input to an image reproduction optical system described below (see FIG. 41). By arranging POFs 732 for sending a trigger light around the lens 734, shading in which the peripheral part of the image becomes dark is suppressed, and it is possible to obtain a high-quality image of an amplified product. Further, the structure of the tip portion of the nozzle unit is not limited to the above-described one, and it is also possible to employ the structure shown in FIG. 40(b). As shown in FIG. 40(b), a nozzle unit 780 has a pumping opening 782 and a POF 784 for sending a trigger light. When a nozzle unit into which a pumping opening, an optical fiber for sending a trigger light and/or an optical fiber for sending an optical image of the inside of a well for a specimen to an image sensor are integrated, and treatment lines linearly arranged are used in this way, by only linearly moving the nozzle unit that carries out both pumping of a specimen or the like and detection of an amplified product of a target nucleic acid along the treatment line, it is possible to carry out from extraction of the target nucleic acid from the specimen to detection of the amplified product, and size reduction in the apparatus can be expected. In particular, the diameter of the nozzle unit can be decreased by the pumping opening and the optical fibers, and therefore the distance between adjacent nozzle units and the distance between treatment lines can be decreased. As a result, it is possible to further reduce the size of the nucleic acid detection apparatus.

Figure 41:
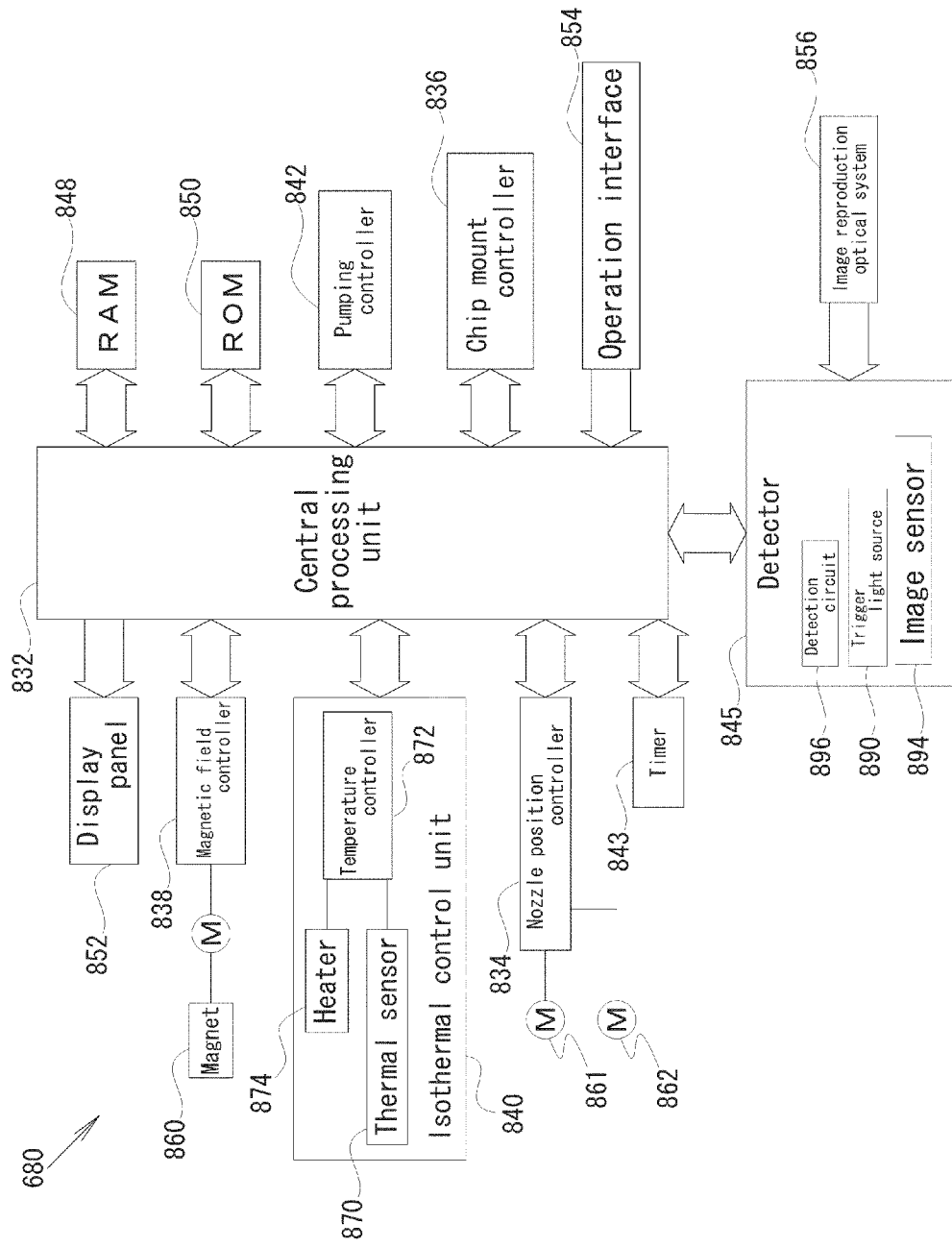
FIG. 41 is a functional block diagram showing the functions of a nucleic acid detection apparatus.

FIG. 41 is a functional block diagram of a target nucleic acid detection apparatus. As shown in FIG. 41, an assay system 680 has a central processing unit 832, a nozzle position controller 834, a chip mount controller 836, a magnetic field controller 838, an isothermal control unit 840, a pumping controller 842, a timer 843, a detector 845, a RAM 848, a ROM 850, a display panel 852, an operation interface 854, an image reproduction optical system 856, etc.

The nozzle position controller 834 has mutually orthogonal axes X and Z (2 axes), and the position of the nozzle unit 720 is controlled by 2 motors, i.e., first and second motors 861 and 862. Regarding the axes X and Z, for example, the axis X toward the direction P is approximately parallel to the arrangement direction of wells in each of the treatment lines 700A to 700F, and the axis Z is approximately perpendicular to the axis X and approximately parallel to the direction of the line between the proximal position and the distal position of wells. When the treatment of the specimen is started and each nozzle unit 720 is moved, for example, the nozzle 720 is driven in two steps, i.e., a movement on the axis X and a movement on the axis Z. In this way, treatments can be carried out along the respective treatment lines 700A to 700F without traversing the treatment lines. In this case, by simultaneously activating the nozzle units 720, it is possible to improve detection environments between the treatment lines 700A to 700F, and it is possible to carry out detection of an amplified product and subsequent analysis with higher accuracy.

Examples of treatment programs to be stored in the ROM 850 include: (1) a first program by which an RNA is extracted from a cell or virus and amplified to carry out detection of an amplified product; (2) a second program by which a DNA is extracted from a biological sample such as blood and amplified to carry out detection of an amplified product; and (3) a third program by which a plasmid DNA is extracted from a bacterium or the like. The program to be stored in the ROM may be suitably changed depending on purposes.

The timer 843 carries out timing according to a program read from the ROM 850. Timing is carried out, for example, when isothermal amplification of a target nucleic acid is performed based on a timing clock. By timing, a period of carrying out each step can be accurately managed.

The isothermal control unit 840 has a thermal sensor 870, a temperature controller 872 and a heater 874. The temperature controller 872 detects a temperature based on a temperature signal from the thermal sensor 870. The thermal sensor 870 is located, for example, adjacent to a well 716 holding a freeze-dried reagent for nucleic acid amplification, and transmits the temperature signal to the temperature controller 872 depending on the temperature of a target nucleic acid-containing solution held in the well 716. The temperature controller 872 controls energization of the heater 874 based on the temperature signal from the thermal sensor 870, thereby controlling the temperature of the fluid in the well 716 to become a predetermined temperature. In this way, isothermal amplification, which requires a constant temperature, or a PCR reaction, which requires temperature change, can be carried out.

The detector 845 has a trigger light source 890, an image sensor 894 for receiving a light from a POF 740, a detection circuit 896, etc. By guiding a trigger light from the trigger light source 890 through the POF 732, the trigger light can be sent to the inside of the well 718 for detection. For the image sensor 894, for example, image sensors such as CCD and CMOS can be used, and after receiving a light from an image reproduction optical system 856, an image signal is output to the detection circuit 896. The detection circuit 896 performs image processing based on a light receiving signal from the image sensor 894 to perform detection/determination of nucleic acid.

Next, the action of the nucleic acid detection system of the present invention will be described.

The treatment program selected by the user is read from the ROM 850, and based on the read treatment program, the action of each portion of the nucleic acid detection system 680 is started. By the user, the obtained specimen is manually put into the well 702 of each of treatment lines 700A to 700F, and by a shielding door or the like (not shown), the first to sixth treatment lines 700A to 700F are shielded from the outside. In the first to sixth treatment lines 700A to 700F, for example, 2 lines are used for extracting a target nucleic acid from a specimen, amplifying it and then detecting it, 2 lines are used for a negative/positive control, and 2 lines are used for producing a calibration curve. Such use may be suitably changed. After shielding of the first to sixth treatment lines 700A to 700F is detected, the treatment of the specimen is started, and the nozzle unit 720 is driven to mix the specimen with the dissolving solution. After stirring of the mixture, the magnetic particles are added to the mixture, followed by stirring.

After stirring the mixture to which the magnetic particles have been added, the magnetic particles are constrained to obtain magnetic particles to which the target nucleic acid is bound. The obtained magnetic particles are mixed with a separating solution for breaking the bond between the magnetic particles and the target nucleic acid. After mixing, the target nucleic acid is separated from the magnetic particles, thereby obtaining the target nucleic acid. The obtained target nucleic acid-containing solution is temporarily held in the well 714 to be provided to the amplification step. The target nucleic acid-containing solution held in the well 714 is dispensed into the well 716 in which a reagent for nucleic acid amplification is held in advance, and a mineral oil is further dispensed, thereby carrying out an isothermal amplification reaction.

In this regard, as the isothermal amplification reaction, for example, the LAMP (Loop-Mediated Isothermal Amplification) method is used. As well known, in the LAMP method, a strand displacement activity enzyme and two primer pairs (inner primer and outer primer) are used to obtain an amplified product. In the LAMP method, there is no need to perform thermal denaturation for changing the double strand to the single strand in a template nucleic acid, and therefore, the amplification step can be carried out isothermally. Moreover, when using the PCR method, the amplification cycle of about 5 minutes is repeated at least about 25 to 30 times, and in the isothermal nucleic acid amplification method such as the LAMP method, it is possible to obtain an amplified product sufficient for detection for about 30 minutes. Basic points regarding primer design are described, for example, in International Publication WO 2000/28082 pamphlet and International Publication WO 2002/24902 pamphlet.

For the isothermal amplification reaction step, in addition to the above-described LAMP method, for example, the following methods can be employed:

ICAN (Isothermal and Chimeric primer-initiated Amplification of Nucleic Acid) method using a chimeric primer;

RCA (Rolling Cycle Amplification) method in which an amplified product is obtained using open circle probes (OCP), DNA ligase, a primer pair and strand displacement type DNA polymerase;

SDA (Strand Displacement Amplification) method in which an amplified product is obtained using two primer pairs, a restriction enzyme, a strand displacement activity enzyme and a phosphorothioate analog substrate;

IVT (In Vitro Transcription) method;

TRC (Transcription Reverse transcription Concerted amplification) method in which an RNA is obtained as an amplified product by trimming the RNA using a reverse transcriptase or the like;

NASBA (Nucleic Acid Sequence-Based Amplification) method in which an RNA is amplified using 3 types of enzymes such as a reverse transcriptase and an RNA polymerase and a template-specific primer pair; and SPIA method in which an amplified product is obtained using a primer having a chimeric structure of an RNA and a DNA.

Any method, in which a target nucleic acid is amplified at a constant temperature, can be applied.

Thus, the isothermal amplification reaction step is preferably used instead of the PCR method, since there is no need to increase or decrease the temperature of the nucleic acid solution from room temperature to 94° C., 72° C. or 55° C. for amplification of the target nucleic acid, and therefore there is no need to use an apparatus for increasing a temperature to a relatively high temperature such as a thermal cycler. Further, in the isothermal amplification method, time required for obtaining a sufficient amount of amplified product for detection is about several tens of minutes, and therefore, reduction in time required for extraction to detection of the target nucleic acid can be expected.

After the extracted target nucleic acid-containing solution is mixed with the freeze-dried reagent for nucleic acid amplification, a hydrophobic fluid is put into the well 716 by the nozzle unit 720. As the hydrophobic fluid, for example, a chain saturated hydrocarbon represented by $C_nH_{2n+2}$ (n is an integer from 3 to 20), so-called mineral oil is exemplified, and preferably, liquid paraffin of $C_nH_{2n+2}$ (n is an integer from 16 to 20) is exemplified, and such a hydrophobic fluid is put into the well 716. By the mineral oil, invasion of contaminant from the outside into the well 716 for nucleic acid amplification can be prevented, and in addition, evaporation of a mixed solution of the target nucleic acid-containing solution and the reagent for isothermal amplification can be prevented. Further, instead of the mineral oil or in combination with the mineral oil, a sealant formed in the solid state for blocking the opening of the well 716 may be fitted to the opening of the well 716 using the nozzle unit 720.

After amplification of the target nucleic acid, an amplified production solution is moved to the well 718 for detection by the nozzle unit 720, and detection of the amplified product is carried out.

Figure 42:
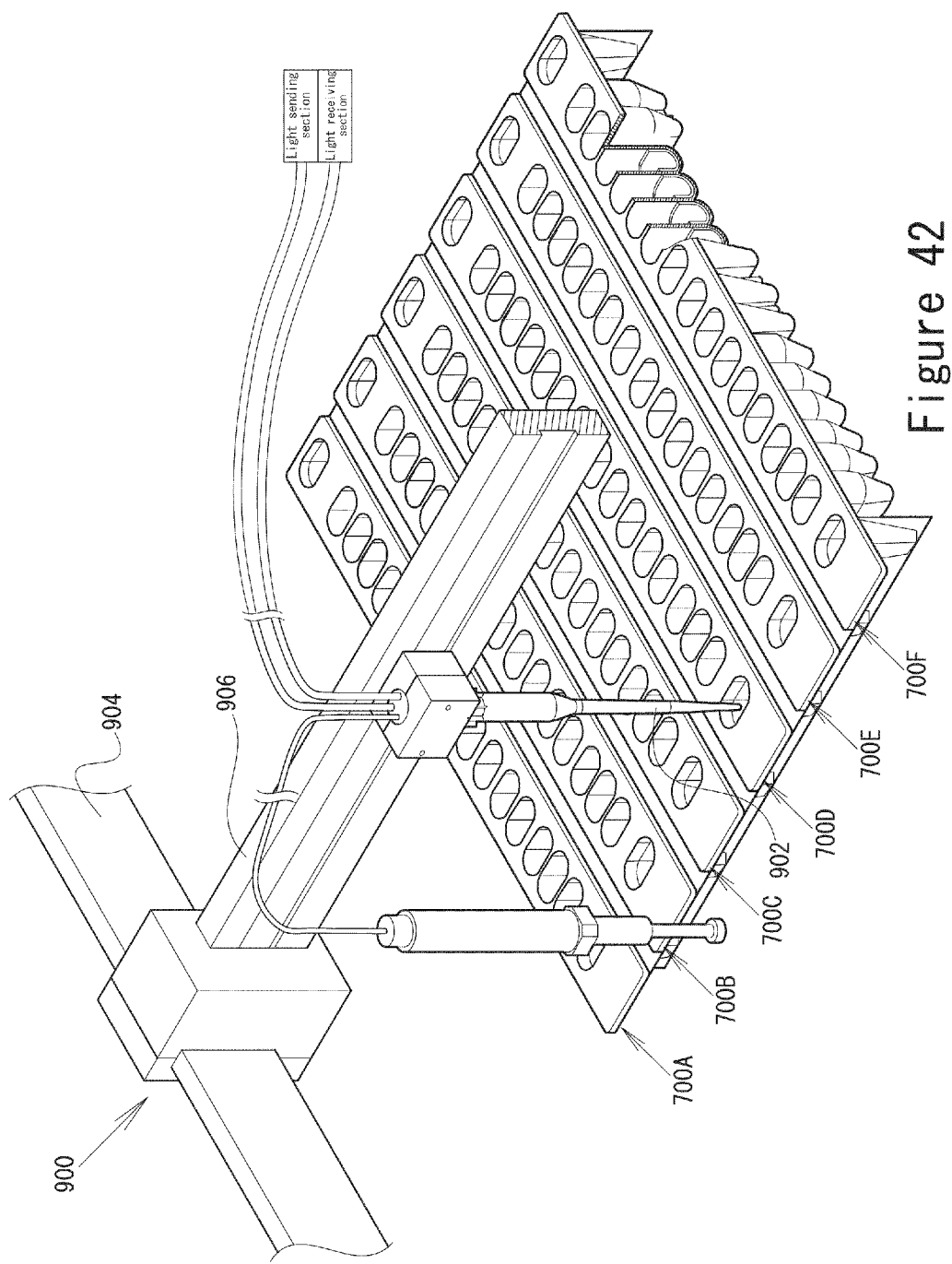
FIG. 42 is a perspective view schematically showing a nucleic acid detection apparatus having only one nozzle unit having a pumping opening, an optical fiber for sending a trigger light and a lens for detection.

Thus, by arranging the well 702 for holding a specimen, a well for holding magnetic particles for target nucleic acid extraction, a well for washing and a well for holding a freeze-dried reagent for isothermal amplification in order in a linear fashion, the nozzle unit 720 can be driven without loss, and further reduction in treatment time can be expected. Moreover, since the nozzle unit 720 and the pipette chip 730 are driven in a linear fashion, mixing of the specimen of another treatment line can be prevented, and contamination can be reduced. Furthermore, simultaneously at the 6 treatment lines Further, the embodiment of the detection apparatus for the target nucleic acid is not limited to the explanation described above, and various changes can be employed. For example, in FIG. 38 describe above, the system has the 6 treatment lines 700A to 700F and the 6 nozzle units 720 corresponding to the treatment lines 700A to 700F, but the number of nozzle units may be one. FIG. 42 is a perspective view schematically showing a target nucleic acid detection apparatus having one nozzle unit. As shown in FIG. 42, a nucleic acid detection apparatus 900 has one nozzle unit 902. The nozzle unit 902 can be moved along the well arrangement direction by a first guiding rail 904, and can be moved along the direction of traversing the first to sixth treatment lines 700A to 700F along a second guiding rail 906. By providing such a constitution of the apparatus, the number of nozzle units may be decreased, and an apparatus may be provided at low cost.

Further, in the above-described embodiment, the image sensor 894 and the trigger light source 890 are provided, but a nucleic acid detection apparatus into which a photomultiplier tube is integrated instead of the image sensor may also be employed.

Figure 43:
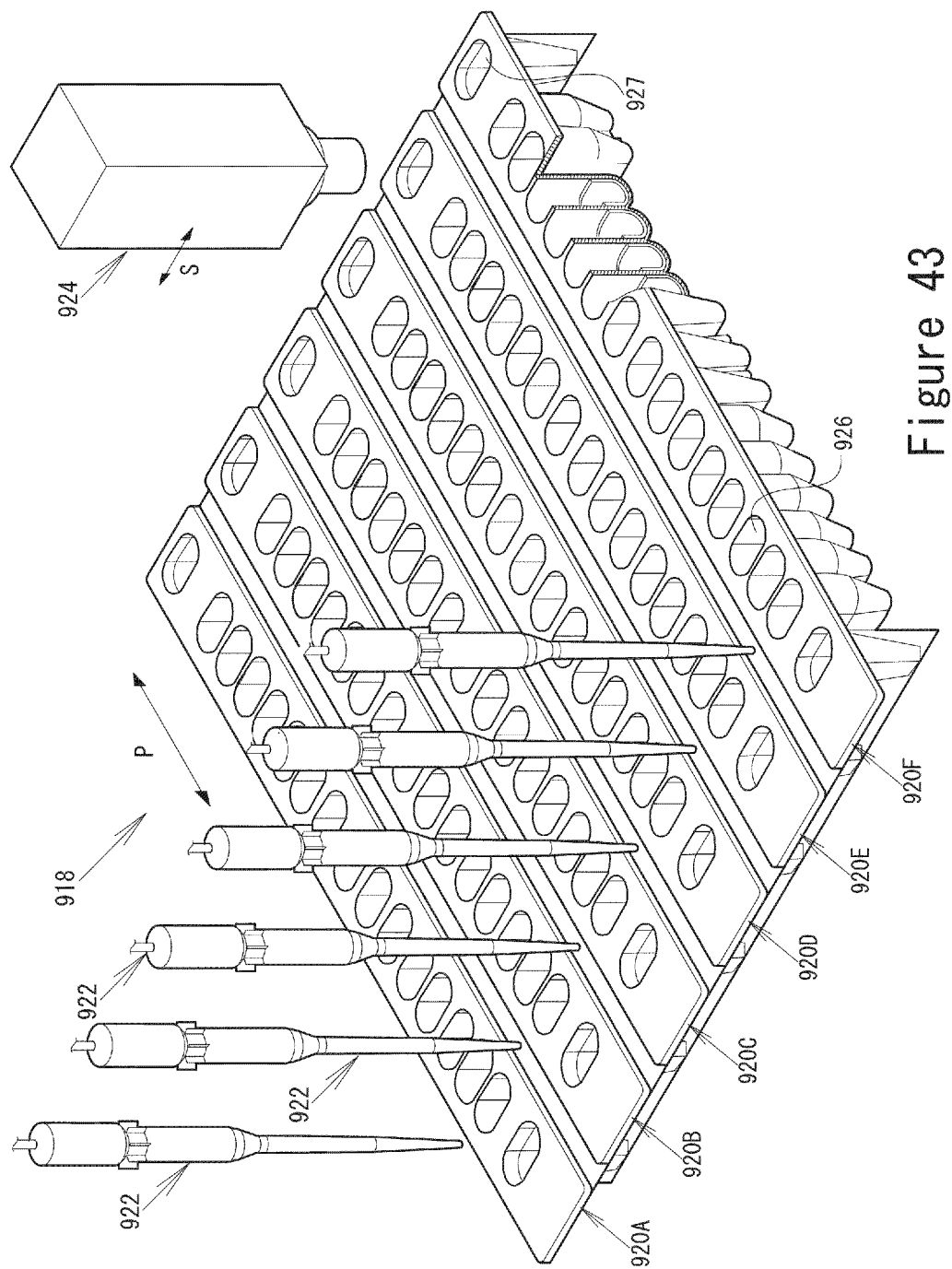
FIG. 43 is a perspective view showing the main portion of a nucleic acid detection apparatus having nozzles for dispensing provided to respective treatment lines and a single nucleic acid detector separately.

Further, a nozzle for dispensing and a detector for target nucleic acid may be provided independently. As shown in FIG. 43, a nucleic acid detection apparatus 918 has 6 dispensing nozzles 922 corresponding to first to sixth treatment lines 920A to 920F and one nucleic acid detector 924. The dispensing nozzles 922 are controlled to be moved in the arrangement direction of wells 926, and the detector 924 is provided above a well 927 for detection so as to be moved in the direction S traversing the first to sixth treatment lines 920A to 920F. By providing such a constitution of the apparatus, efficient treatments can be expected.

Figure 44:
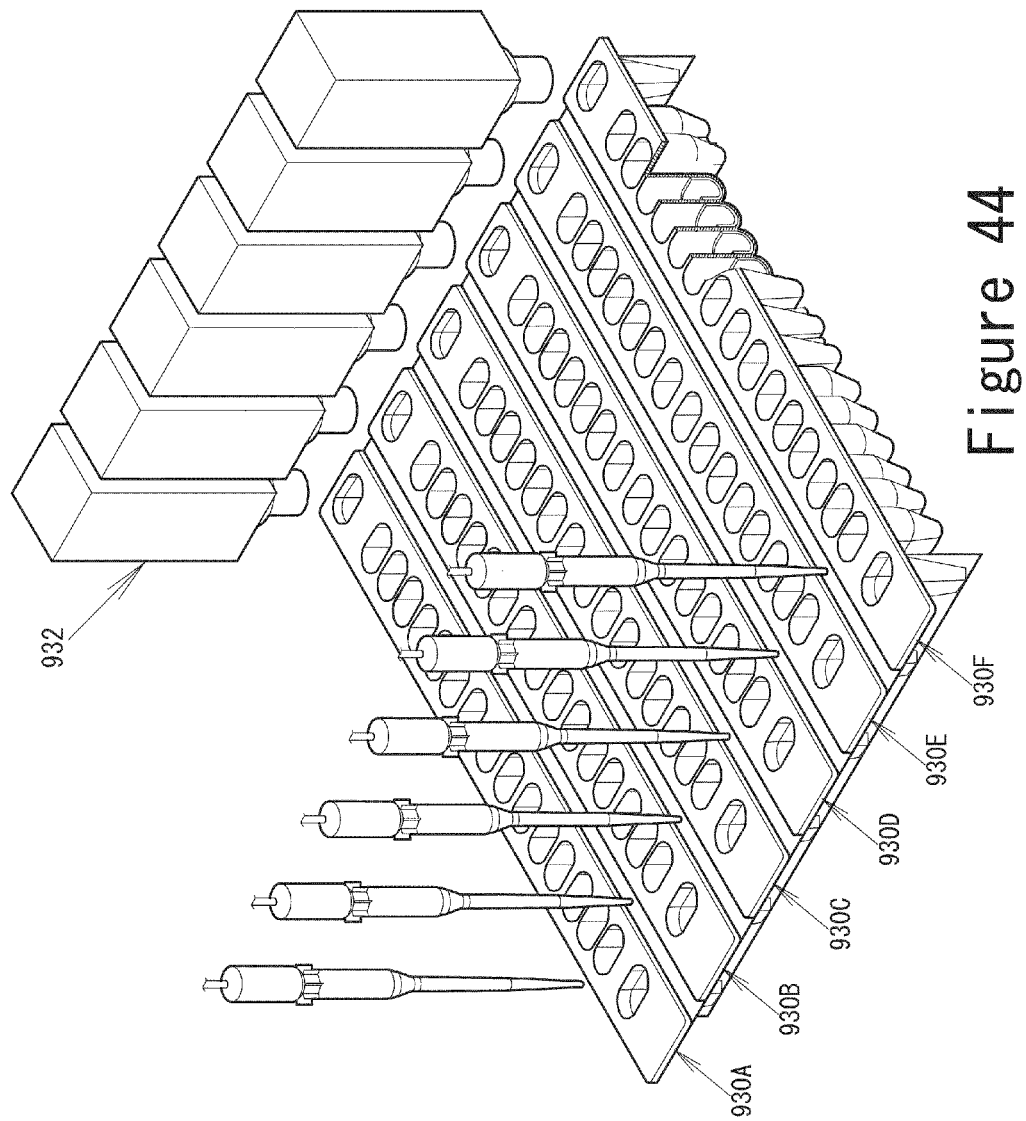
FIG. 44 is a perspective view of a nucleic acid detection apparatus having nucleic acid detectors corresponding to respective treatment lines.

Further, the number of the nucleic acid detector is not limited to one, and a plurality of nucleic acid detectors can be provided corresponding to respective treatment lines as shown in FIG. 44. As shown in FIG. 44, nucleic acid detectors 932 are provided corresponding to first to sixth treatment lines 930A to 930F. When providing such a constitution of the apparatus, the drive mechanism of the detectors 932 is not required, and therefore, further improvement of treatment efficiency can be expected.

When the isothermal amplification method is used for the step of amplifying a target nucleic acid in a nucleic acid amplification apparatus having a plurality of treatment lines, there is a case where nucleic acid amplification rates of respective lines are different from each other. In this case, reaction temperature may be corrected by a temperature controller. By correcting the temperature of amplification reaction, the balance between amplification rates of treatment lines can be expected, and more accurate quantitation of the target nucleic acid can be expected.

Figure 45:
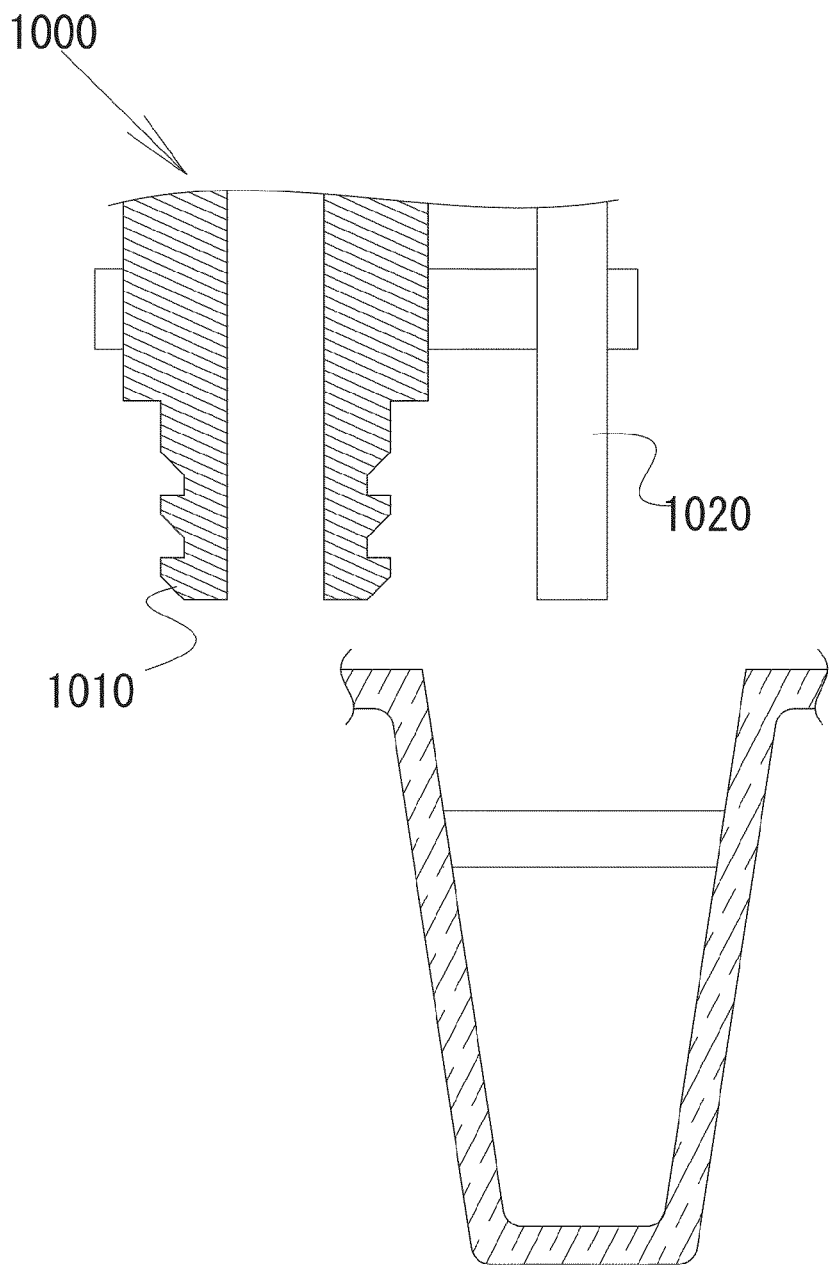
FIG. 45 is a cross portional view showing an embodiment in which an optical fiber is provided to the outside of a nozzle for dispensing.

In the explanation above, the pumping opening 730 and the plastic optical fiber 740 for transmitting an optical image of an amplified product to the image sensor 894 are provided in the nozzle unit 720, but an optical fiber for transmitting an optical image of an amplified product to the image sensor may be provided to the outside of the pumping opening. FIG. 45 is a cross sectional view of a unit, in which an optical fiber for transmitting an optical image of the inside of a well for detection to an image sensor is placed at the outside of a pumping opening, taken along a plane approximately parallel to the drawing direction of an optical fiber. An integrated unit 1000 has a nozzle portion 1010 and an optical fiber portion 1020, and the optical fiber portion 1020 is placed at the outside of the nozzle portion 1010. Thus, the unit in which the optical fiber is placed at the outside of the nozzle portion 1010 may also be employed.

Figure 46:
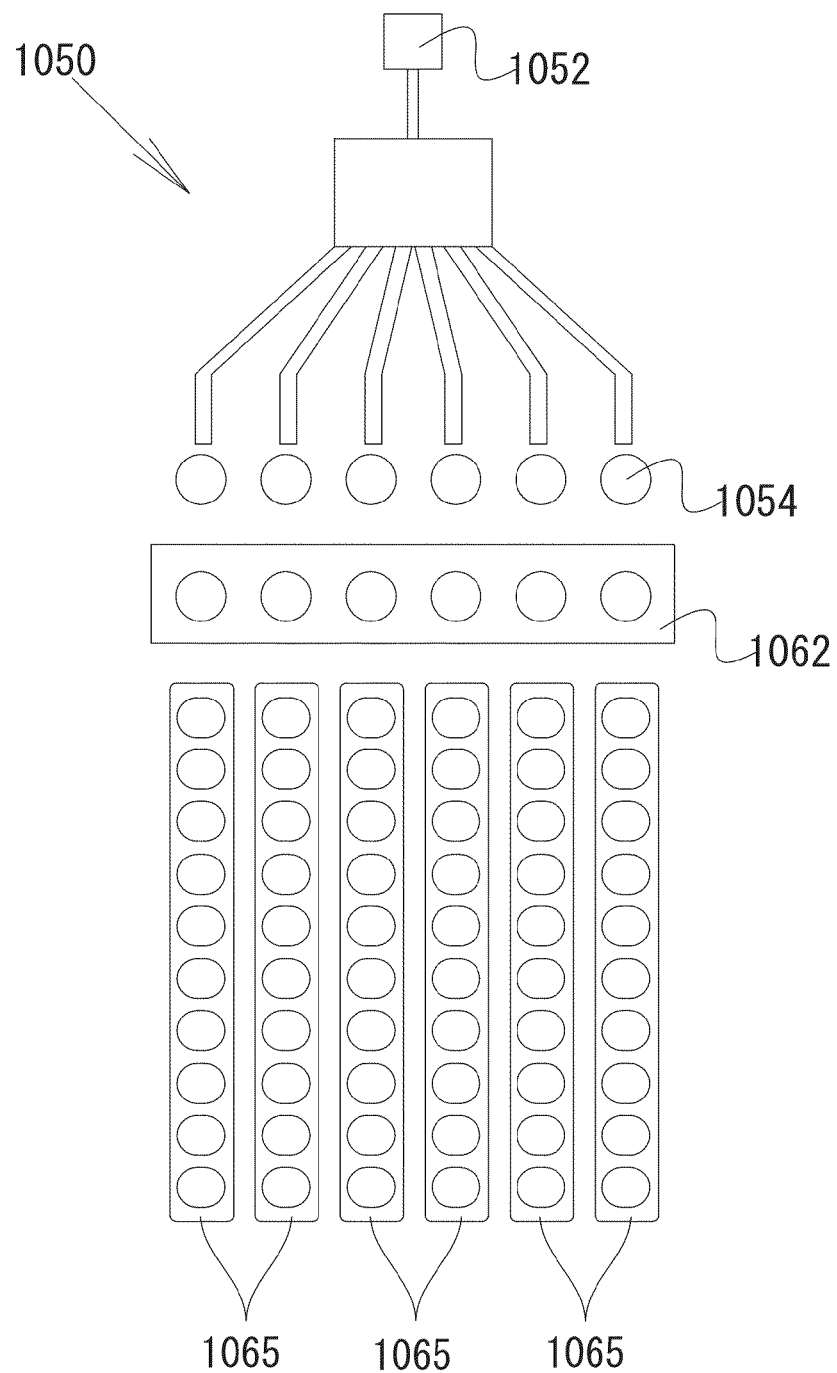
FIG. 46 is an explanatory drawing schematically showing a nucleic acid detection apparatus having a single detector and a switching apparatus for allowing the detector to selectively correspond to each of wells for detection.

Moreover, as shown in FIG. 46, in a nucleic acid detection apparatus having a plurality of wells for detection, it is also possible to provide an optical fiber to each of the wells for detection so that an amplified product in each of the wells for detection can be detected, and to selectively use these plurality of optical fibers to detect a target nucleic acid using a single detector. A nucleic acid detection apparatus 1050 has: a single image sensor 1052; a switching apparatus 1060 for selectively transmitting an optical image of the inside of a well 1054 for detection to the image sensor 1052; a nozzle 1062 for dispensing; treatment lines 1065 in which a plurality of wells for carrying out extraction to amplification of a target nucleic acid are arranged, etc. It is possible to employ such a constitution of the apparatus, in which an amplified product can be detected from each well 1054 for detection by switching of the switching apparatus.

EXAMPLES

Hereinafter, the present invention will be described in more detail based on Examples, but the present invention is not limited to the Examples.

Example 1

Treatment of AFP-Containing Specimen

[Purpose]
Regarding HAMA and human rheumatoid factor (IgM), contaminant thereof was treated and removed using Protein G magnetic particles or anti-Human IgM magnetic particles, and influence of the treatment on values of AFP (α-fetoprotein) was examined.
[Specimens and Apparatuses Used]
ELISA plate to which anti-AFP HYb-2051 is immobilized in advance (F96 MAXISORP
NUNC-IMMUNO PLATE (442404, Nunc.))
Serum control (Liquichek Immunoassay Plus Control Level 2, Bio-Rad)
HAMA (Human Anti Mouse Antibody) 1 mg/ml
Dynabeads Protein G (Dynal, Invitrogen) (magnetic particles)
BioMag anti-Human IgM (Bangs Laboratories, Inc.) (magnetic particles)
AFP antigen (Original conc. 4 mg/ml)
AFP-HRP labeling antibody (Original conc. 0.13 mg/ml)
Block Ace Powder (1 pack: 4 g for 100 ml, Cat. No. UK-B80, manufactured by Snow Brand Milk Products Co., Ltd.)
10×PBS
8 continuous pipettes
Disposable plate
SPECTRAMAX190 (Molecular Devices) & SoftMax Pro 4.8
Nunc-Immuno Wash 8
TMB Peroxidase Substrate & Peroxidase Solution B (H2O2) (KPL: Kirkegaard & Perry Laboratories)
ELISA reaction termination solution (1.0 N $H_2SO_4$)
Sucker
Kim Towel
[Content of Experiment]
Specimens shown in Sample Nos. 1 to 6 below were prepared, and AFP values were measured.
[Calculation of Binding Ability of Magnetic Particles]
For obtaining an AFP value of each specimen, binding ability of magnetic particles was calculated in advance.
The content of each immunoglobulin in serum is shown in Table 1 below.

In 5 μl of serum, about 0.04 to 0.10 mg of IgG is present, and for adsorption to Dynabeads protein G, 100 to 250 μl of beads is required.
Further, in 5 μl of serum, about 7.5 μg of IgM is present, and for adsorption to BioMag anti-Human IgM, 50 μl of beads is required.
[Preparation of Washing Solution]
Block Ace Powder was dissolved in about 90 ml of Milli-Q water. After confirmation of dissolution, the solution was subjected to filling up to 100 ml using a 100 ml measuring cylinder. 100 ml of 10×PBS was put into a 1 L measuring cylinder, Block Ace Powder was added thereto, and the mixture was subjected to filling up to 1000 ml by addition of Milli-Q water.
[Measurement of Absorbance of Each Specimen]
In this experiment, absorbance of each of 6 types of specimens (Sample Nos. 1 to 6) was measured. The amount of a reaction specimen on an ELISA plate was 50 μl. As the serum, Liquichek Immunoassay Plus Control Level 2 was used. Regarding the labeling antibody AFP-HRP, 1/800 and n=3 were employed.
[Sample No. 1]
As a control, PBS (Phosphate buffered salinel) buffer solution was used, and regarding a specimen treated with Dynabeads protein G, a specimen treated with BioMag anti-Human IgM and an untreated specimen, absorbance of each of them was measured.
[Sample No. 2]
As a serum control, a solution containing 5 μl of serum was used, and regarding a specimen treated with Dynabeads protein G, a specimen treated with BioMag anti-Human IgM and an untreated specimen, absorbance of each of them was measured.
[Sample No. 3]
A solution containing 5 μl of serum and 10% HAMA was prepared. Using this solution, regarding a specimen treated with Dynabeads protein G and an untreated specimen, absorbance of each of them was measured.
[Sample No. 4]
A solution containing 5 μl of serum and 10% rheumatoid factor was prepared. Using this solution, regarding a specimen treated with BioMag anti-Human IgM and an untreated specimen, absorbance of each of them was measured.
[Sample No. 5]
A solution containing 5 μl of serum, 10% HAMA and 80 ng/ml of AFP was prepared. Using this solution, regarding a specimen treated with Dynabeads protein G and an untreated specimen, absorbance of each of them was measured.
[Sample No. 6]
A solution containing 5 μl of serum, 10% rheumatoid factor and 80 ng/ml of AFP was prepared. Using this solution, regarding a specimen treated with BioMag anti-Human IgM and an untreated specimen, absorbance of each of them was measured.
[Results]
Measurement results as shown in Table 2 below were obtained.

TABLE 1

|  | IgM | IgD | IgG1 | IgG2 | IgG3 | IgG4 | IgA1 | IgA2 | IgE |
|---|---|---|---|---|---|---|---|---|---|
| Molucular weight (kDa) | 970 | 184 | 146 | 146 | 165 | 146 | 160 | 160 | 188 |
| Serum level (mg/ml) | 1.5 | 0.03 | 9 | 3 | 1 | 0.5 | 2.0 | 0.5 | $5 \times 10^{-5}$ |
| (%) |  | 8.6 | 0.2 | 51.3 | 17.1 | 5.7 | 2.9 | 11.4 | 2.9 |

Reference: The IMMUNE SYSTEM

TABLE 2

| Sample No. | Specimen | Treatment | Abs450TMB | Average | Standard deviation | Vriation coefficient |
|---|---|---|---|---|---|---|
| 1 | Control (PBS buffer solution) | ProteinG | 0.0653 0.0638 0.0634 | 0.0642 | 0.0008179 | 0.0127 |
| | | Bio Mag | 0.0651 0.0658 0.0692 | 0.0667 | 0.0017907 | 0.0268 |
| | | No beads | 0.0685 0.0653 0.0614 | 0.0651 | 0.0029033 | 0.0446 |
| 2 | Serum control | ProteinG | 0.2777 0.2713 0.2676 | 0.2722 | 0.0041721 | 0.0153 |
| | | Bio Mag | 0.2841 0.2862 0.2913 | 0.2872 | 0.0030232 | 0.0105 |
| | | No beads | 0.2959 0.2938 0.3110 | 0.3002 | 0.0076613 | 0.0255 |
| 3 | Serum + HAMA | ProteinG | 0.2631 0.2510 0.2488 | 0.2543 | 0.006287 | 0.0247 |
| | | No Beads | 1.2472 1.2698 1.2919 | 1.2696 | 0.0182491 | 0.0144 |
| 4 | Serum + rheumatoid factor | Bio Mag | 0.7160 0.6947 0.6645 | 0.6917 | 0.0211292 | 0.0305 |
| | | No Beads | 0.7215 0.7225 0.7253 | 0.7231 | 0.0016083 | 0.0022 |
| 5 | Serum + HAMA + AFP | ProteinG | 0.8900 0.8594 0.8596 | 0.8697 | 0.0143781 | 0.0165 |
| | | No Beads | 1.4009 1.4537 1.4631 | 1.4392 | 0.0273761 | 0.0190 |
| 6 | Serum + rheumatoid factor + AFP | Bio Mag | 1.3443 1.3345 1.3136 | 1.3308 | 0.0128034 | 0.0096 |
| | | No Beads | 1.3512 1.3732 1.3782 | 1.3675 | 0.0117284 | 0.0086 |

[Calculation of AFP]

Figure 47:
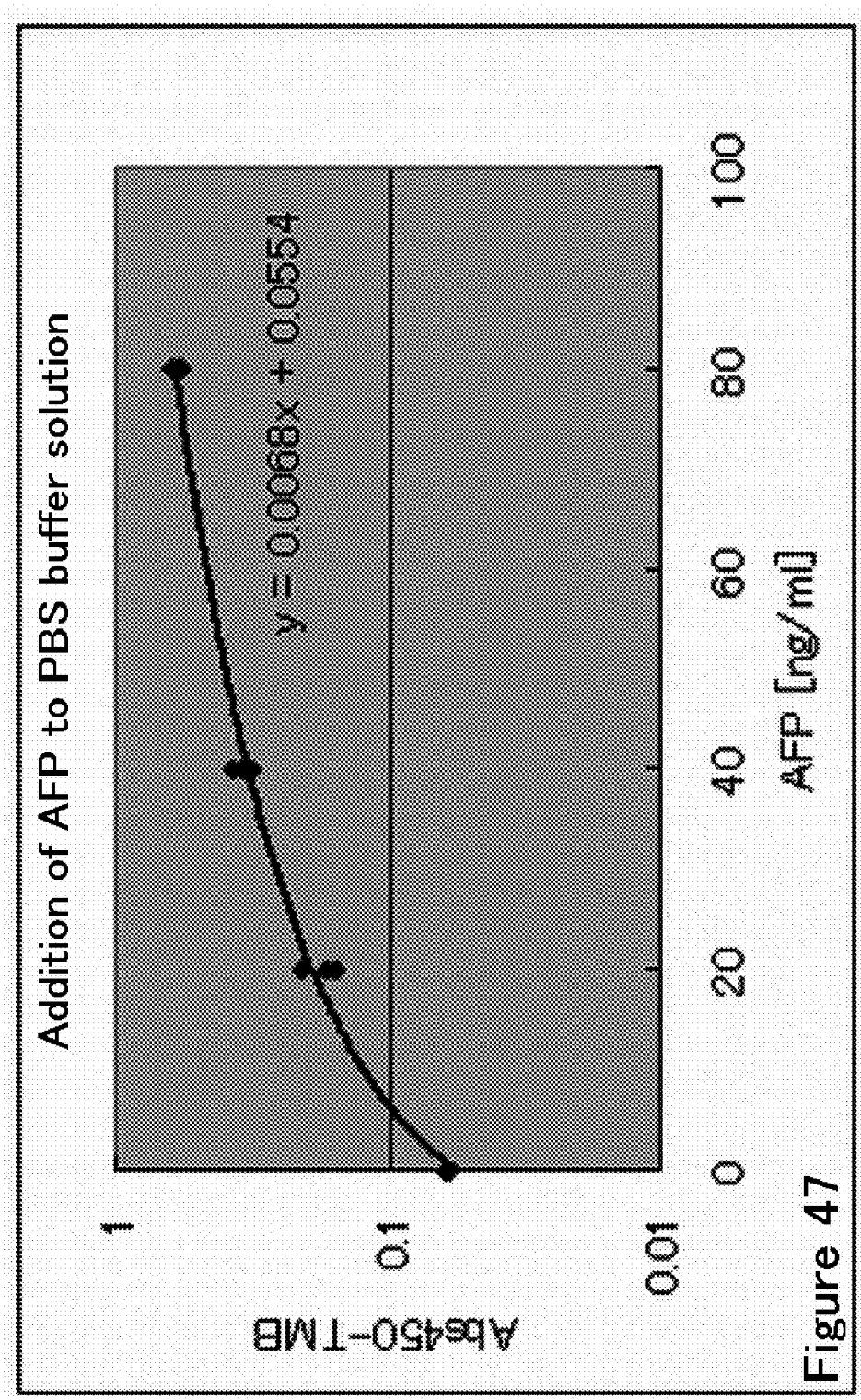
FIG. 47 is a graph showing a standard curve for obtaining an AFP value based on addition of AFP to serum.
Figure 48:
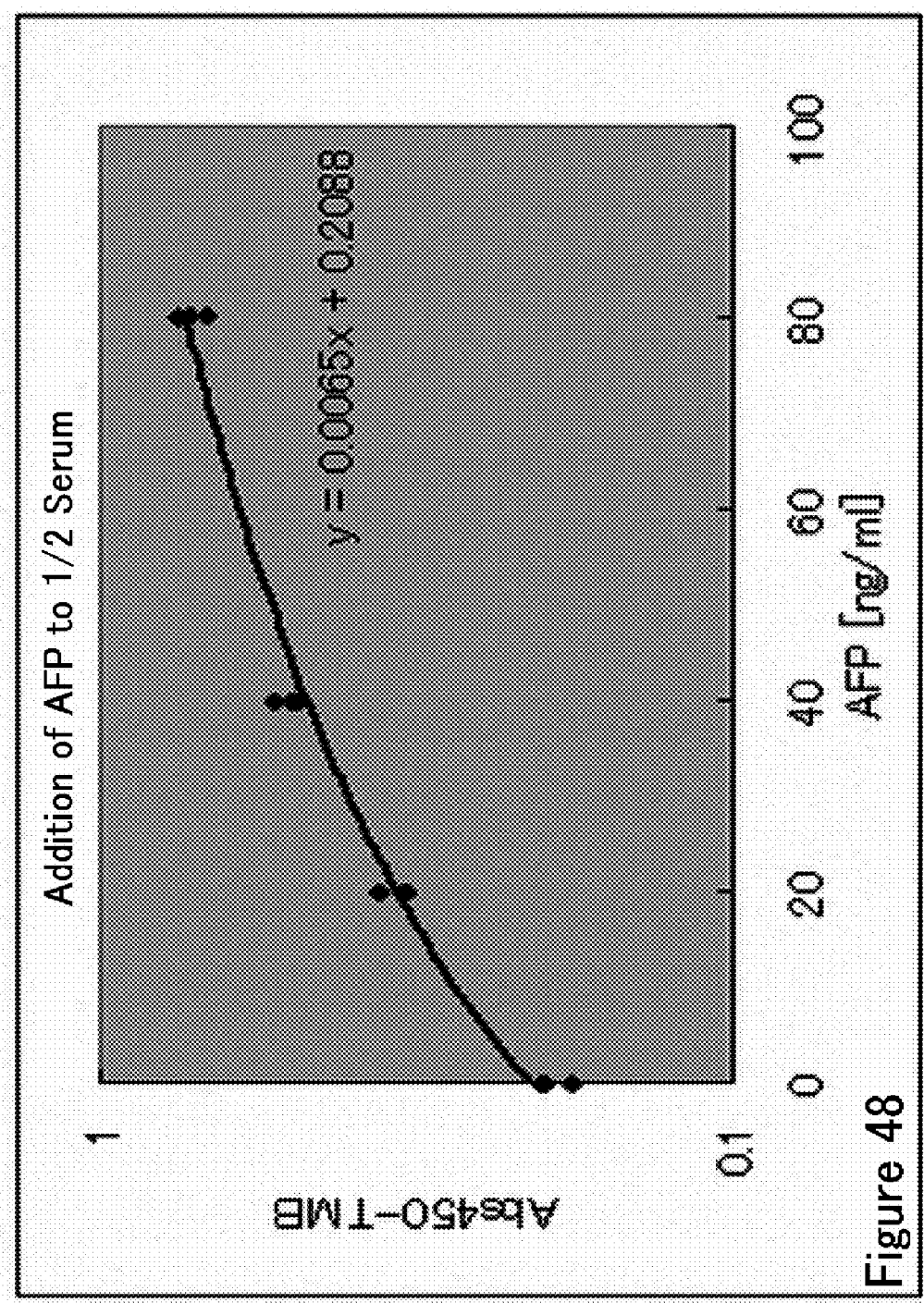
FIG. 48 is a graph showing a standard curve for obtaining an AFP value based on addition of AFP to PBS buffer solution.

AFP values were calculated based on values of Abs450TMB shown in Table 2 above. For calculation of AFP values, among the following mathematical formulae obtained from FIGS. 47 and 48:

$$y=0.0065x+0.2088 \quad \text{Formula (1)}$$

$$y=0.0068x+0.0554 \quad \text{Formula (2),}$$

Formula (1) was used.

The calculated AFP values are shown in Table 3 below.

TABLE 3

| Sample No. | Specimen | Treatment | Beads treatment | AFP value [ng/ml] |
|---|---|---|---|---|
| 1 | Control (PBS buffer solution) | ProteinG | Done | 1.29 |
| | | Bio Mag | Done | 1.66 |
| | | No beads | Not done | 1.43 |
| 2 | Serum control | ProteinG | Done | 9.75 |
| | | Bio Mag | Done | 12.06 |
| | | No beads | Not done | 14.06 |
| 3 | Serum + HAMA | ProteinG | Done | 7.00 |
| | | No Beads | Not done | 163.20 |
| 4 | Serum + rheumatoid factor | Bio Mag | Done | 74.30 |
| | | No Beads | Not done | 79.12 |
| 5 | Serum + HAMA + AFP | ProteinG | Done | 101.68 |
| | | No Beads | Not done | 189.29 |
| 6 | Serum + rheumatoid factor + AFP | Bio Mag | Done | ✕Substract 66.20 |
| | | No Beads | Not done | ✕Substract 67.02 |

✕shows difference from Sample 4.

[Consideration Regarding Experiment Results]

As shown by the AFP value in the case of no treatment ("no beads" treatment) of Sample No. 3, the AFP value was increased due to the presence of HAMA, and therefore, it is considered that there is a possibility that HAMA is a false-positive factor.

In order to confirm this consideration, HAMA was treated with Dynabeads protein G. As a result, the AFP value in the case of treatment of Sample No. 3 with Dynabeads protein G was 7.00, and the AFP value was decreased to a level similar to that of the AFP value shown for Sample No. 2.

Therefore, it was confirmed that HAMA is a factor causing false positive.

Regarding the AFP values of Sample No. 4, the AFP value in the case of treatment with BioMag was almost the same as the AFP value in the case of no treatment ("no beads" treatment).

CONCLUSION

By treating and removing the contaminant contained in the specimen using Protein G Dynabeads, IgM, which is thought to be the cause for false positive, can be removed from the specimen. Therefore, the amount of AFP existing in the specimen can be more accurately measured.

EXPLANATIONS OF LETTERS OR NUMERALS 10 pipette chip
12 well
20 column-containing pipette chip
30 membrane-containing pipette chip
40 gel-containing pipette chip
50 pipette chip (tubular chip)
70 antigen separation/immobilization tube
72 spacer beads
100 assay system
102 central processing unit
106 chip mount controller
108 magnetic field controller
112 pumping controller
130 magnet
140 pump
146 pressure sensor
150 assay system
151 magnet
152 dispensing apparatus
153 heat block
154 detection apparatus
162 nozzle
164 pipette chip
170 PMT
171 light source
180 cartridge
181 base panel
182 holding portion
260 assay system
262 system body
264 cartridge

The invention claimed is:

1. A biologically-relevant substance assay device, comprising:
   (a) a specimen holding portion in which a specimen is held;
   (b) a first holding portion in which magnetic particles for trapping a biologically-relevant substance from the specimen are held;
   (c) a second holding portion in which a reagent for detecting the biologically-relevant substance is held; and
   (d) a dispensing mechanism for dispensing the specimen into the specimen holding portion;
   wherein the specimen holding portion, the first holding portion, and the second holding portion are arranged in line and in the order according to the content of the treatment of the specimen and the biologically-relevant substance, and each of the first holding portion and the second holding portion includes a plurality of wells, each well being separated from adjacent wells by a well wall,
   wherein the device further comprises a dispensing position controller configured for controlling the position of the dispensing mechanism, a magnet configured for constraining the magnetic particles in a nozzle of the dispensing mechanism, and a magnetic field controller configured for managing the placement of the magnet to control the strength of the magnetic field provided to the nozzle of the dispensing mechanism, the dispensing position controller moves the dispensing mechanism in a perpendicular direction with respect to the line and in a horizontal direction parallel to the line, and the magnetic field controller moves the magnet in the horizontal direction parallel to the line, and
   wherein a tip portion of the nozzle has a pumping opening, at least one optical fiber configured for sending a trigger light and a lens for receiving light from the biologically-relevant substance.

2. The device according to claim 1, wherein the magnetic particles are held in a dispensing chip.

3. The device according to claim 1, further having a mechanism for sliding upper portions of the holding portions.

4. The device according to claim 1, wherein the specimen holding portion, the first holding portion and the second holding portion are arranged in an approximate straight line.

5. The device according to claim 1, wherein the reagent for detecting is freeze-dried in advance.

6. The device according to claim 1, wherein the first and second holding portions are formed into a cartridge.

7. The device according to claim 6, wherein the specimen holding portion, the first holding portion, and the second holding portion are integrated into the cartridge.

8. The device according to claim 1, wherein the biologically relevant substance is a nucleic acid.

9. The device according to claim 8, wherein the reagent for detecting comprises a reagent for nucleic acid amplification using a PCR method or an isothermal amplification method and a reagent for detecting an amplified product.

10. The device according to claim 1, wherein the reagent for detecting is a freeze-dried reagent, and the device further includes a well containing the freeze dried reagent, and the biologically-relevant substance is detected by using the freeze-dried reagent.

11. The device according to claim 1, further comprising one or more of treatment lines including the specimen holding portion, the first holding portion, and the second holding portion.

12. The device according to claim 11, further comprising one or more of nozzle units linearly moved along the one or more of treatment lines.

13. The device according to claim 1, further comprising (e) a mechanism selected from the group consisting of: a mechanism for removing or putting lids for covering the respective holding portions; a mechanism for receiving a light from the biologically-relevant substance irradiated with the irradiating light to detect the biologically relevant substance; and a mechanism in which the mechanisms are combined.

14. The device according to claim 13, wherein the mechanisms in (d) and the mechanism in (e) or a mechanism in which the mechanisms in (d) and the mechanism in (e) are combined are installed in a single nozzle.

15. The device according to claim 1, wherein the lens is placed in the pumping opening.

16. The device according to claim 1, wherein a plurality of the at least one optical fiber are arranged around the pumping opening.

17. The device according to claim 1, wherein the pumping opening and the lens are disposed in the central portion of the tip portion of the nozzle.

18. A method for assaying a nucleic acid, wherein the nucleic acid is extracted and detected using the device according to claim 1.

* * * * *